(12) United States Patent
Vadivelu et al.

(10) Patent No.: US 11,319,326 B2
(45) Date of Patent: May 3, 2022

(54) TRICYCLIC FUSED DERIVATIVES OF 1-(CYCLO)ALKYL PYRTDIN-2-ONE USEFUL FOR THE TREATMENT OF CANCER

(71) Applicant: JUBILANT BIOSYS LIMITED, Karnataka (IN)

(72) Inventors: Saravanan Vadivelu, Bangalore (IN); Sridharan Rajagopal, Bangalore (IN); Murugan Chinnapattu, Bangalore (IN); Pavan Kumar Gondrala, Bangalore (IN); Dhanalakshmi Sivanandhan, Bangalore (IN); Chandrika Mulakala, Bangalore (IN)

(73) Assignee: JUBILANT BIOSYS LIMITED, Karnataka (IN)

( * ) Notice: Subject to any disclaimer, the term of this patent is extended or adjusted under 35 U.S.C. 154(b) by 0 days.

(21) Appl. No.: 16/869,517

(22) Filed: May 7, 2020

(65) Prior Publication Data
US 2020/0331926 A1    Oct. 22, 2020

Related U.S. Application Data

(62) Division of application No. 15/562,381, filed as application No. PCT/IN2016/050098 on Mar. 30, 2016, now Pat. No. 10,689,390.

(30) Foreign Application Priority Data

Mar. 30, 2015    (IN) ............................ 1636/CHE/2015

(51) Int. Cl.
C07D 491/04    (2006.01)
C07D 471/04    (2006.01)
A61P 35/00    (2006.01)
A61K 45/06    (2006.01)

(52) U.S. Cl.
CPC ............ *C07D 491/04* (2013.01); *A61P 35/00* (2018.01); *C07D 471/04* (2013.01); *A61K 45/06* (2013.01); *A61K 2300/00* (2013.01)

(58) Field of Classification Search
CPC .................................................. C07D 491/04
See application file for complete search history.

(56) References Cited

U.S. PATENT DOCUMENTS

2015/0087636 A1    3/2015    Sverdrup

FOREIGN PATENT DOCUMENTS

| GB | 1545767 A | 5/1979 |
|---|---|---|
| JP | 2013-529611 A | 7/2013 |
| JP | 2013-544847 A | 12/2013 |
| RU | 2506267 C2 | 2/2014 |
| WO | WO 2008/133288 A1 | 11/2008 |
| WO | WO 2012/075383 A2 | 6/2012 |
| WO | WO 2014/128067 A1 | 8/2014 |
| WO | WO-2014/139324 A1 | 9/2014 |
| WO | WO 2015/018520 A1 | 2/2015 |

OTHER PUBLICATIONS

Bae, Cancer Targeted Drug Delivery, Springer: New York, 2013, p. v.*
Hayat, M.A. Autophagy Cancer, Other Pathologies, Inflammation, Immunity, Infection, and Aging vol. 5 Academic Press: Sand Diego, 2015, p. xxi.*
Carlo C. Maley and Mel Greaves Frontiers in Cancer Research Springer: 2016, pp. 18-19.*
Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e419S.*
Sanz-Garcia, "Current and advancing treatments for metastatic colorectal cancer" Expert Opinion on Biological Therapy, 16:1, 2016, 93-110.*

(Continued)

*Primary Examiner* — David K O'Dell
(74) *Attorney, Agent, or Firm* — Foley & Lardner LLP

(57) ABSTRACT

The present disclosure described heterocyclic compounds of Formula I or, its stereoisomers, pharmaceutically acceptable salts, complexes, hydrates, solvates, tautomers, polymorphs, racemic mixtures, optically active forms and pharmaceutically active derivative thereof and pharmaceutical compositions containing them as the active ingredient. The present disclosure also describes the synthesis and characterization of aforementioned compounds to exhibit high anticancer activity. The compounds of the present disclosure are useful as medicaments and their use in the manufacture of medicaments for treatment, prevention or suppression of diseases, and conditions mediated by one or more BET family of bromodomains.

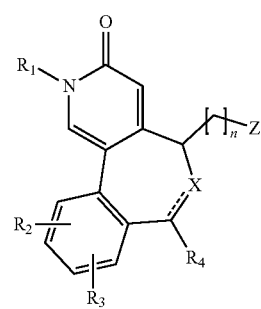

Formula I

16 Claims, No Drawings

(56) References Cited

OTHER PUBLICATIONS

Garson "Models of ovarian cancer—Are we there yet?" Molecular and Cellular Endocrinology 239 (2005) 15-26.*
Sale "Models of ovarian cancer metastasis: Murine models" Drug Discovery Today: Disease Models 2006, 3, 150-154.*
Schober "New Advances in the Treatment of Metastatic Pancreatic Cancer" Digestion 2015;92:175-184.*
Boniface "Multidisciplinary management for esophageal and gastric cancer" Cancer Management and Research 2016:8 39-44.*
Gerratana "Do platinum salts fit all triple negative breast cancers?" Cancer Treatment Reviews 48 (2016) 34-41.*
Yoo "New drugs in prostate cancer" Prostate Int 4 (2016) 37-42.*
Vardiman "The World Health Organization (WHO) classification of the myeloid neoplasms" Blood (2002), 100(7), 2292-2302.*
Pui "Treatment of Acute Lymphoblastic Leukemia" New England Journal of Medicine 2006, 354, 166-78.*
Krishnan "Multiple myeloma and persistence of drug resistance in the age of novel drugs (Review)" International Journal of Oncology 49: 33-50, 2016.*
Stewart "Novel therapeutics in multiple myeloma" Hematology 2012, 17(S1), s105-s108.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et al. "Relationships between drug activity in NCI preclinical in vitro and in vivo models and early clinical trials." British Journal of Cancer 2001, 84, 1424-1431.*
Belkina "BET domain co-regulators in obesity, inflammation and cancer" Nature Reviews Cancer 2012.*
Lockwood "Sensitivity of human lung adenocarcinoma cell lines to targeted inhibition of BET epigenetic signaling proteinsis functionally distinct." PNAS Nov. 20, 2012, vol. 109, No. 47, 19408-19413.*
Cain, C. SciBX 4(31); "Bromodomain brake on AML" Published online Aug. 11, 2011, 1-2.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*
Argollo "Novel therapeutic targets for inflammatory bowel disease" Journal of Autoimmunity (2017), 85, 103-116.*
De Angelis "Pharmacotherapy in Secondary Progressive Multiple Sclerosis: An Overview" CNS Drugs (2018) 32:499-526.*
Chaichian "Targeted Therapies in Systemic Lupus Erythematosus: A State-of-the-Art Review" J Clin Cell Immunol 2013, S6, 1-8.*
Mahieu "A critical review of clinical trials in systemic lupus erythematosus" Lupus (2016) 25, 1122-1140.*
Skog "Revisiting the notion of type 1 diabetes being a T-cell-mediated autoimmune disease" Curr Opin Endocrinol Diabetes Obes 2013, 20:118-123.*

Bai, Xue "Small PARP inhibitor PJ-34 induces cell cycle arrest and apoptosis of adult T-cell leukemia cells." Journal of Hematology & Oncology, 2015, 8, 117/1-117/12.*
Zhang, "Clinical efficacy and safety of huperzine A in treatment of mild to moderate Alzheimer disease, a placebo-controlled, double-blind, randomized trial."Zhonghua Yixue Zazhi, 2002, 82(14), 941-944.*
Chen "Selective cellular uptake and retention of SN 28049, a new DNA-binding topoisomerase II-directed antitumor agent" Cancer Chemother Pharmacol (2014) 74:25-35.*
Su et al., "Multiplex Imaging and Cellular Target Identification of Kinase Inhibitors via an Affinity-Based Proteome Profiling Approach," *Scientific Reports*, No. 5, 10 pages (Jan. 2015).
Brand, et al., "Small Molecule Inhibitors of Bromodomain-Acetyl-lysine Interactions," *ACS Chemical Biology*, vol. 10, 22-39 (2015).
Filippakopoulos et al., "Targeting Bromodomains: Epigenetic Readers of Lysine Acetylation," *Nat. Rev. Drug Discovery*, vol. 13, No. 5, pp. 337-356 (2014) [Abstract].
French et al., "BRD4-NUT Fusion Oncogene: A Novel Mechanism in Aggressive Carcinoma," *Cancer Research*, vol. 63, pp. 304-307 (Jan. 2003).
French et al., "BRD-NUT oncoproteins: a family of closely related nuclear proteins that block epithelial differentiation and maintain the growth of carcinoma cells," *Oncogene*, vol. 27, pp. 2237-2242 (2008).
French et al., "Midline Carcinoma of Children and Young Adults with NUT Rearrangement," *Journ. Of Clinical Oncology*, vol. 22, pp. 4135-4139 (2004).
Griebenow, et al., "Identification of 4H,6H-[2]benzoxepino[4,5-c][1 2]oxazoles as novel squalene synthase inhibitors," *Bioorg. Med. Chem. Lett.*, vol. 21, pp. 3648-3653 (2011) [Abstract].
Hargreaves, et al., "Control of Inducible Gene Expression by Signal-Dependent Transcriptional Elongation," *Cell*, vol. 138, No. 1, pp. 129-145 (Jul. 2009).
Ichikawa et al., "Discovery of DF-461, a Potent Squalene Synthase Inhibitor," *ACS Medicinal Chemistry Letters*, vol. 4, pp. 932-936 (2013).
LeRoy et al., "The double bromodomain proteins Brd2 and Brd3 couple histone acetylation to transcription," *Mol. Cell.*, vol. 30, No. 1, pp. 51-60 (Apr. 2008).
Foreign Action other than Search Reporton JP 2017-551712 dated Nov. 19, 2019.
Office Action issued in co-pending Russian Patent Application No. 2017135205, dated Jun. 28, 2019.
Wolf, "Burger's Medicinal Chemistry, 5ed, Part 1," John Wiley & Sons, 1995, pp. 975-977.
Banker, et al., Modern Pharmaceutics, 3ed, Marcel Dekker, New York, 1996, pp. 451 and 596.
Rautio, et al., "Prodrugs: Design and Clinical Applications," Nature Reviews Drug Discovery 2008, 7, pp. 255-270.
Beaumont, "Design of Ester Prodrugs to Enhance Oral Absorption of Poorly Permeable Compounds: Challenges to the Discovery Scientist," Current Drug Metabolism, 2003, 4, pp. 461-485.
Bernard Testa, "Predicting Drug Metabolism: Concepts and Challenges," Pure and Applied Chemistry 2004, vol. 76, No. 5, pp. 907-914.
Kirchmair, "Predicting Drug Metabolism: Experiment and/or Computationn?", Nat. Rev. Drug. Discov., Jun. 2015; 14(6), pp. 387-404.
Shi, et al., "The Mechanisms Behind the Therapeutic Activity of BET Bromodomain Inhibition," *Molecular Cell*, vol. 54, pp. 728-736, Table S1 (Jun. 2014).
Baratta, et al., "An In-Tumor Genetic Screen Reveals that the BET Bromodomain Protein, BRD4, is a Potential Therapeutic Target in Ovarian Carcinoma," *PNAS*, vol. 112, No. 1, pp. 232-237 (Jan. 2015).

* cited by examiner

TRICYCLIC FUSED DERIVATIVES OF 1-(CYCLO)ALKYL PYRTDIN-2-ONE USEFUL FOR THE TREATMENT OF CANCER

CROSS-REFERENCE TO RELATED APPLICATIONS

This application is a division of U.S. patent application Ser. No. 15/562,381, filed Sep. 27, 2017 (now U.S. Pat. No. 10,689,390), which is the National Stage of International Patent Application No. PCT/IN2016/050098, filed Mar. 30, 2016, which claims priority from India Provisional Patent Application No. 1636/CHE/2015, filed Mar. 30, 2015. The contents of these applications are incorporated herein by reference in their entirety.

TECHNICAL FIELD

The present disclosure relates to the field of medicinal chemistry and more particularly to the development of compounds as inhibitors of one or more BET family of bromodomians. The present disclosure relates to heterocyclic compounds of the Formula (I), its stereoisomers, pharmaceutically acceptable salts, complexes, hydrates, solvates, tautomers, polymorphs, racemic mixtures, optically active forms and pharmaceutically active derivative thereof and pharmaceutical compositions containing them as the active ingredient.

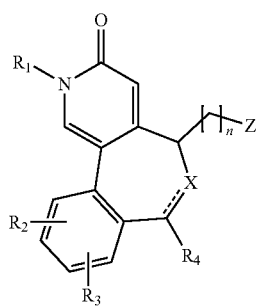

(I)

The present disclosure further relates to the synthesis and characterization of aforementioned compounds to exhibit anticancer activity. The compounds of the present disclosure are useful as medicaments and their use in the manufacture of medicaments for treatment, prevention or suppression of diseases, and conditions mediated by one or more BET family of bromodomains.

BACKGROUND

Transcriptional regulation is a major event in cell differentiation, proliferation and apoptosis. Transcriptional activation of a set of genes determines cellular function and is tightly regulated by a variety of factors. One of the regulatory mechanisms involved in this process is an alteration in the tertiary structure of DNA, which affects transcription factors to their target DNA regiments. Nucleosomal integrity is regulated by the acetylation status of the core histone, with the result being permissiveness to transcription. The regulations of transcription factor are thought to involve changes in the structure of chromatin. Changing the affinity of histone proteins for coiled DNA in the nucleosome alters the structure of chromatin. Hypoacetylated histones are believed to have greater affinity to the DNA and form a tightly bound DNA-histone complex and render the DNA inaccessible to transcriptional regulation. The acetylating status of the histone is governed by the balanced activities of the histone acetyl transferase (HAT) and histone deacetylase (HDAC). The bromodomain and extraterminal family of proteins called as BET proteins are readers of the acetyl status of histone and changes the chromatin structure and gene expression.

The BET family of bromodomain containing proteins comprises four proteins, namely BRD2, BRD3, BRD4 and BRDT, which are widely expressed in various tissues, except BRDT which is localized in the testes. Each of the BRD proteins contains tandem bromodomains capable of binding to acetylated lysine residues in histones H3 and H4. It has been reported that BRD2 and BRD3 are associated with histones along actively transcribed genes and involved in facilitating transcriptional elongation (Leroy et al, Mol. Cell. 2008 30(1):51-60), while BRD4 appears to be involved in the recruitment of the pTEF-[beta] complex to nucleosomes, which results in phosphorylation of RNA polymerase 11 and increases the transcriptional elongation of neighboring genes. (Hargreaves et al, Cell, 2009 138(1): 129-145).

BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). A BET protein which includes BRD4 have been shown to be important regulators of gene expression profiles in numerous diseases such as cancer, diabetes, obesity, cardiovascular and renal disorders. Currently several BRD4 inhibitors is in various stages of clinical trial for cancer such as IBET-762, JQ1, OTX-015 and RVX-2135 (P. Filippakopoulos, et. al., Nature Review Drug Discovery, 13, 2014, 337-356, M. Brand, et. al., ACS Chem. Biol, 10, 2015, 22-39).

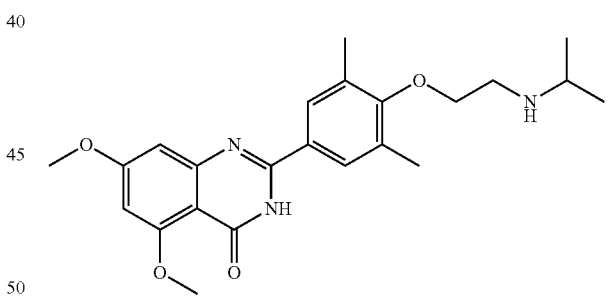

RVX-2135, Phase 1

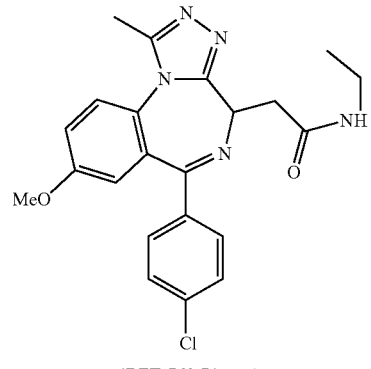

iBET-762-Phase 1

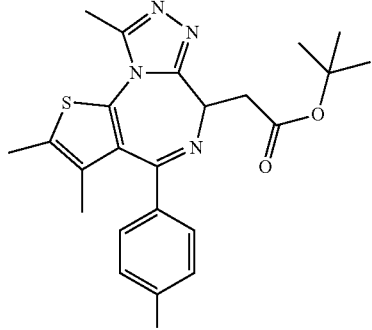

JQ-1-Phase 1

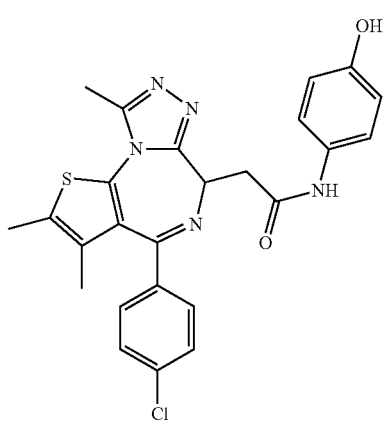

OTX-015-Phase 1

A tricyclic aryl compound as squalene synthase inhibitors has been disclosed in WO2008133288 for the treatment of hypercholesterolemia, hypertriglyceridemia and hypo-HDL cholesterolemia and/or arteriosclerosis.

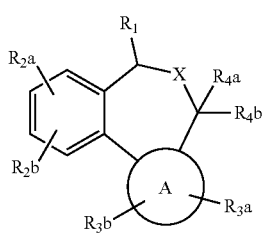

Masanori Ichikawa et. al published a paper (*ACS Med. Chem. Lett.*, 2013, 932-936) describing the squalene synthase inhibitors DF4611 (B) and also Nils Griebenow, et. al. published a paper (*Bioorg. Med. Chem. Lett.* 21, 2011, 3648-3653) on the synthesis of novel 4H,6H-[2]benzoxepino[4,5-c][1,2]oxazoles (C) as squalene synthase inhibitors.

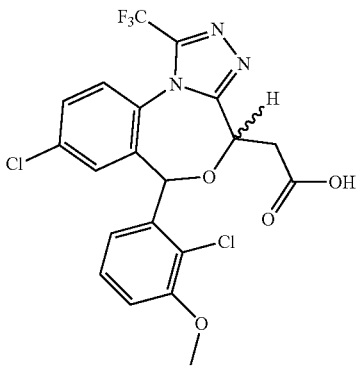

B

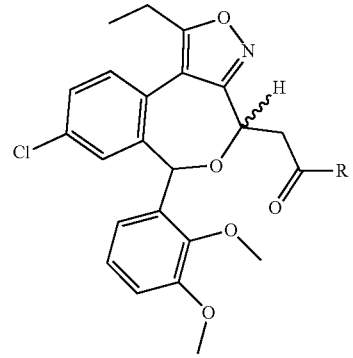

C

Although, there are several chemotherapies and target therapies based drugs for cancer, an effective cure for cancer still remains elusive. Further, development of acquired resistance and disease relapse are major issues that still need to be addressed. Even though several bromodomain inhibitors are known in the clinic as well as in the preclinic, still remains a need for finding potent bromodomain inhibitors having desirable drug like properties.

Therefore, the present invention provides novel and drug like molecules having good potency as BRD4 inhibitors which can inhibit the binding of acetylated lysine residue of histone for controlling gene expressions in various diseases.

SUMMARY

The present disclosure is based on the development of compounds of Formula I (see below) exhibiting advantageous anti-cancer properties. Thus, the present disclosure provides a compound of Formula I Formula I

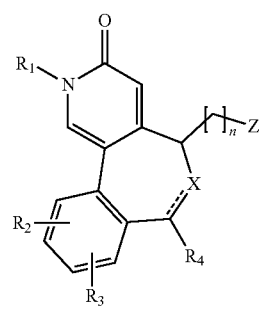

or its stereoisomers, pharmaceutically acceptable salts, complexes, hydrates, solvates, tautomers, polymorphs, racemic mixtures, optically active forms and pharmaceutically active derivative thereof, wherein ----- is a single bond or a double bond; X is selected from —O— or —N—; n is 0-6; $R_1$ is selected from alkyl or cycloalkyl; $R_2$ and $R_3$ are independently selected from hydrogen, halogen, hydroxy, nitro, cyano, azido, nitroso, oxo (=O), thioxo (=S), —SO$_2$—, amino, hydrazino, formyl, alkyl, haloalkyl, alkoxy, haloalkoxy; arylalkoxy; cycloalkyl, cycloalkyloxy, aryl, heterocyclyl, heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogenalkyl, cycloalkyl, aryl, arylalkyl, heterocyclyl, heteroarylorhetroarylalkyl; $R_4$ is selected from hydrogen, alkyl, cycloalkyl, cyloalkenyl, cycloalkylalkyl, aryl, arylalkyl, heterocyclyl, heterocyclylalkyl, heteroaryl, heteroarylalkyl or haloalkyl; Z is selected from hydrogen, —CH$_2$OR$_5$, —COOR$_5$, —CONR$_5$R$_6$, —NHCOOR$_5$, —NHCOR$_5$ or —NHSO$_2$R$_5$; and $R_5$ and $R_6$ are independently selected from hydrogen, hydroxyl, aryl, heteroaryl, cycloalkyl or alkyl.

The present disclosure relates to a composition comprising a compound of Formula (I) or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

The present disclosure further relates to a method of preventing or treating proliferative diseases by administering a therapeutic effective amount of novel compound of the Formula (I) or a pharmaceutically acceptable salt and/or prodrug.

The present disclosure relates to a process of preparation of compound of Formula (I) or its stereoisomers, pharmaceutically acceptable salts, complexes, hydrates, solvates, tautomers, polymorphs, racemic mixtures, optically active forms and pharmaceutically active derivative thereof.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

The term "alkyl" refers to straight or branched aliphatic hydrocarbon chain having the 1-8 carbon atoms. This term is exemplified by groups such as n-butyl, iso-butyl, t-butyl, n-hexyl and the like. The groups may be optionally substituted.

The term "aryl" refers to aromatic radicals having 5 to 18 carbon atoms having a single ring (e.g. phenyl) or multiple rings (e.g. biphenyl), or multiple condensed (fused) rings (e.g. naphthyl or anthranyl), which may be optionally substituted by one or more substituents. Preferred aryl groups, without limitation, include phenyl, naphthyl, indanyl, biphenyl and the like.

The term "arylalkyl" refers to an aryl group directly bonded to an alkyl group, which may be optionally substituted by one or more substituents. Preferred arylalkyl groups, without limitation, include —CH$_2$C$_6$H$_5$, —C$_2$H$_4$C$_6$H$_5$ and the like.

The term "heterocyclyl" refers to a heterocyclic ring radical which may be optionally substituted by one or more substituents. The heterocyclyl ring radical may be attached to the main structure at any heteroatom or carbon atom that results in the creation of a stable structure.

Furthermore the term "heterocyclyl" refers to a stable 2 to 18 membered rings radical, which consists of carbon atoms and from one to five heteroatom's selected from nitrogen, phosphorus, oxygen and sulfur. For purposes of this invention the heterocyclic ring radical may be monocyclic, bicyclic or tricyclic ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated. Preferred heterocyclyl groups, without limitation, include azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyrazolyl, pyridyl, pteridinyl, purinyl, quinazolinyl, qunioxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl and isochromanyl.

The term "heteroaryl" refers to a heteroaromatic carbocyclic group of 2 to 18 carbon atoms having a single ring (e.g. pyridine) or multiple rings (e.g. isoquinoline), or multiple condensed (fused) rings. Preferred heteroaryls include thiophene, pyrazole, thiazole, pyridine and the like. The groups may be optionally substituted.

The term "heteroarylalkyl" refers to a heteroaryl group directly bonded to an alkyl group, which may be optionally substituted by one or more substituents. Preferred heteroarylalkyl groups, without limitation, include-CH$_2$-pyridinyl, —C$_2$H$_4$-furyl and the like.

The term "cycloalkyl" refers to non-aromatic mono or polycyclic ring system of about 3 to 12 carbon atoms, which may be optionally substituted by one or more substituent's. The polycyclic ring denotes hydrocarbon systems containing two or more ring systems with one or more ring carbon atoms in common, i.e., a spiro, fused or bridged structures. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g. spiro [4.4] non-2-yl and the like.

The term "alkoxy" refers to an alkyl group attached via an oxygen linkage to the rest of the molecule, which may be optionally substituted by one or more substituents. Preferred alkoxy groups, without limitation, include —OCH$_3$, —OC$_2$H$_5$ and the like.

The term "alkylthio" refers to an alkyl group attached via a sulfur linkage to the rest of the molecule, which may be optionally substituted by one or more substituents. Preferred alkylthio groups, without limitation, include —SCH$_3$, —SC$_2$H$_5$ and the like.

The term "alkylamino" refers to an alkyl group as defined above attached via amino linkage to the rest of the molecule, which may be optionally substituted by one or more substituent's. Preferred alkylamino groups, without limitation include-NHCH$_3$, —N(CH$_3$)$_2$, and the like.

The term "alkenyl" refers to an aliphatic hydrocarbon group containing a carbon-carbon double bond and which may be straight or branched chain having about 2 to 10 carbon atoms, which may be optionally substituted by one or more substituent's. Preferred alkenyl groups, without limitation, include ethenyl, 1-propenyl, 2-propenyl, iso-propenyl, 2-methyl-1-propenyl, 1-butenyl, 2-butenyl and the like.

The term "alkynyl" refers to a straight or branched hydrocarbyl radicals having at least one carbon-carbon triple bond and having in the range of 2-12 carbon atoms, which may be optionally substituted by one or more substituent's. Preferred alkynyl groups include, without limitation, ethynyl, propynyl, butynyl and the like.

"Halo" or "Halogen", alone or in combination with any other term means halogens such as chloro (Cl), fluoro (F), bromo (Br) and iodo (I).

Furthermore, the compound of formula (I) can be its derivatives, analogs, tautomeric forms, stereoisomer's, diastereomers, geometrical isomers, polymorphs, solvates, intermediates, metabolites, prodrugs or pharmaceutically acceptable salts and compositions.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds. It is also understood that some isomeric form such as diastereomers, enantiomers and geometrical isomers can be separated by physical and/or chemical methods and by those skilled in the art. Pharmaceutically acceptable solvates may be hydrates or comprising of other solvents of crystallization such as alcohols, ether, and the like.

The term "solvate", as used herein, refers to a crystal form of a substance which contains solvent.

The term "hydrate" refers to a solvate wherein the solvent is water.

The phrase "pharmaceutical acceptable" refers to compounds or compositions that are physiologically tolerable and do not typically produce allergic or similar untoward reaction, including but not limited to gastric upset or dizziness when administered to mammal.

Pharmaceutically acceptable salts forming part of this invention include salts derived from inorganic bases such as like Li, Na, K, Ca, Mg, Fe, Cu, Zn and Mn; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, ammonium, substituted ammonium salts, aluminum salts and the like. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents, for example, include those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician The compounds described herein can also be prepared in any solid or liquid physical form, for example the compound can be in a crystalline form, in amorphous form and have any particle size. Furthermore, the compound particles may be micronized or nanoized, or may be agglomerated, particulate granules, powders, oils, oily suspensions or any other form of solid or liquid physical forms.

The compounds described herein may also exhibit polymorphism. This invention further includes different polymorphs of the compounds of the present invention.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "prodrugs" refers to the precursor of the compound of formula (I), which on administration undergoes chemical conversion by metabolic processes before becoming active pharmacological substances. In general, such prodrugs will be functional derivatives of a compound of the invention, which are readily convertible in vivo into a compound of the invention.

The present disclosure relates to a compound of Formula I

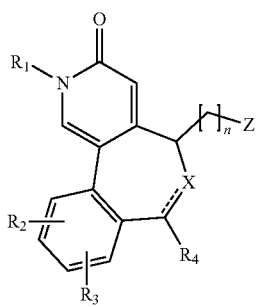

Formula I or its stereoisomers, pharmaceutically acceptable salts, complexes, hydrates, solvates, tautomers, polymorphs, racemic mixtures, optically active forms and pharmaceutically active derivative thereof, wherein ---- ---- is a single bond or a double bond; X is selected from —O— or —N—; n is 0-6; $R_1$ is selected from alkyl or cycloalkyl; $R_2$ and $R_3$ are independently selected from hydrogen, halogen, hydroxy, nitro, cyano, azido, nitroso, oxo (=O), thioxo (=S), —$SO_2$—, amino, hydrazino, formyl, alkyl, haloalkyl, alkoxy, haloalkoxy; arylalkoxy; cycloalkyl, cycloalkyloxy, aryl, heterocyclyl, heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ or —$SO_2R_a$, wherein $R_a$, $R_b$ and $R_c$ are independently selected from hydrogenalkyl, cycloalkyl, aryl, arylalkyl, heterocyclyl, heteroarylorhetroarylalkyl; $R_4$ is selected from hydrogen, alkyl, cycloalkyl, cyloalkenyl, cycloalkylalkyl, aryl, arylalkyl, heterocyclyl, heterocyclylalkyl, heteroaryl, heteroarylalkyl or haloalkyl; Z is selected from hydrogen, —$CH_2OR_5$, —$COOR_5$, —$CONR_5R_6$, —$NHCOOR_5$, —$NHCOR_5$ or —$NHSO_2R_5$ and $R_5$ and $R_6$ are independently selected from hydrogen, hydroxyl, aryl, heteroaryl, cycloalkyl or alkyl.

According to an embodiment, the present disclosure relates to a compound of the Formula (I) or its stereoisomers, pharmaceutically acceptable salts, complexes, hydrates, solvates, tautomers, polymorphs, racemic mixtures, optically active forms and pharmaceutically active derivative thereof, wherein ---- is a single bond or a double bond; X is selected from —O— or —N—; n is 0-1; $R_1$ is selected from $C_1$-$C_8$ alkyl or $C_3$-$C_8$cycloalkyl; $R_2$ and $R_3$ are independently selected from hydrogen, fluoro, chloro, bromo, iodo, hydroxy, nitro, cyano, azido, nitroso, oxo (=O), thioxo (=S), —$SO_2$—, amino, hydrazino, formyl, $C_1$-$C_8$alkyl, $C_1$-$C_8$haloalkyl independently substituted with upto three halogen selected from fluoro, chloro, bromo, or iodo, $C_1$-$C_8$alkoxy, $C_1$-$C_8$haloalkoxy; $C_5$-$C_{18}$arylalkoxy; $C_3$-$C_8$cycloalkyl, $C_3$-$C_8$cycloalkyloxy, $C_5$-$C_{18}$aryl, $C_2$-$C_{18}$heterocyclyl, $C_2$-$C_{18}$heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ or —$SO_2R_a$, wherein $R_a$, $R_b$ and $R_c$ are independently selected from hydrogen, $C_1$-$C_8$alkyl, $C_3$-$C_8$cycloalkyl, $C_5$-$C_{18}$aryl, $C_5$-$C_{18}$arylalkyl, $C_2$-$C_{18}$heterocyclyl, $C_2$-$C_{18}$heteroaryl and $C_2$-$C_{18}$hetroarylalkyl; $R_4$ is selected from hydrogen, $C_1$-$C_8$alkyl, $C_2$-$C_8$alkynyl, $C_3$-$C_8$cycloalkyl, $C_3$-$C_8$cyloalkenyl, $C_3$-$C_8$cycloalkylalkyl, $C_5$-$C_{18}$aryl, $C_5$-$C_{18}$arylalkyl, $C_2$-$C_{18}$heterocyclyl, $C_2$-$C_{18}$heterocyclylalkyl, $C_2$-$C_{18}$heteroaryl, $C_2$-$C_{18}$heteroarylalkyl or $C_1$-$C_8$haloalkyl, wherein alkyl, cycloalkyl, cycloalkenyl, cycloalkylalkyl, aryl, arylalkyl, heterocyclyl, heterocyclylalkyl, heteroaryl and heteroarylalkyl are independently unsubstituted or substituted with upto three substituents independently selected from halogen, alkyl, alkenyl, alkynyl, alkoxy, acyl, acyloxy, amino, hydroxy, keto, nitro, azido, cyano, amide, sulfonamide and carbamate, wherein the heterocyclyl, heterocyclylalkyl, heteroaryl and heteroarylalkyl contains upto three heteroatoms selected from O, N or S; Z is selected from hydrogen, —$CH_2OR_5$, —$COOR_5$, —$CONR_5R_6$, —$NHCOOR_5$, —$NHCOR_5$ or —$NHSO_2R_5$, wherein $R_5$ and $R_6$ are independently selected from hydrogen, hydroxyl, $C_5$-$C_{18}$aryl, $C_2$-$C_{18}$heteroaryl, $C_3$-$C_8$cycloalkyl or $C_1$-$C_8$alkyl; wherein $R_5$ and $R_6$ are optionally substituted with one or more substituents selected from fluorine, chlorine, bromine, iodine, hydroxy, nitro, cyano, azido, nitroso, oxo (=O), thioxo (=S), —$SO_2$, amino, hydrazino, formyl, $C_1$-$C_8$alkyl, $C_1$-$C_8$haloalkylalkoxy, $C_1$-$C_8$haloalkoxy;

$C_5$-$C_{18}$arylalkoxy; $C_3$-$C_8$cycloalkyl, $C_3$-$C_8$cycloalkyloxy, $C_5$-$C_{18}$aryl, $C_2$-$C_{18}$heterocyclyl, $C_2$-$C_{18}$heteroaryl, alkylamino, —COOR$^a$, —C(O)R$^b$, —C(S)R$^a$, —C(O)NR$^a$R$^b$, —C(S)NR$^a$R$^b$, —NR$^a$C(O)NR$^b$R$^c$, NR$^a$C(S)NR$^b$R$^c$, —N(R$^a$)SOR$^b$, —N(R$^a$)SO$_2$R$_b$, —NR$^a$C(O)OR$^b$, —NR$^a$R$^b$, —NR$^a$C(O)R$^b$—, NR$^a$C(S)R$^b$—, —SONR$^a$R$^b$—, —SO$_2$NR$^a$R$^h$—, —OR$^a$, —OR$^a$C(O)OR$^b$—, —OC(O)NR$^a$R$^b$, OC(O)R$^a$, —OC(O)NR$^a$R$^b$—, —R$^a$NR$^b$R$^c$, —R$^a$-OR$^b$—, —SR$^a$, —SOR$^a$ for —SO$_2$R$^a$, wherein R$^a$, R$^b$ and R$^c$ are independently selected from hydrogen, or optionally substituted groups selected from alkyl, cycloalkyl, aryl, arylalkyl, heterocyclyl, heteroarylorhetroarylalkyl.

According to another embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein ---- is a single bond or a double bond; X is selected from —O— or —N—; n is 0-1; R is selected from hydrogen, methyl, ethyl, n-propyl, ispopropyl, n-butyl, isobutyl, t-butyl, pentyl, hexyl, heptyl, octyl, cyclopropyl, cyclobutyl, cyclopentylorcyclohexyl; $R_2$ and $R_3$ are independently selected from hydrogen, fluorine, chlorine, bromine, iodine; hydroxy, nitro, cyano, azido, nitroso, oxo (=O), thioxo (=S), —SO$_2$—, amino, hydrazino, formyl, alkyl, haloalkyl group such as trifluoromethyl, tribromomethyl, trichloromethyl and the like; alkoxy, haloalkoxy such as —OCH$_2$C and the like; arylalkoxy such as benzyloxy, phenylethoxy and the like; cycloalkyl, cycloalkyloxy, aryl, heterocyclyl, heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SO$_2$NR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogen, alkyl, cycloalkyl, aryl, arylalkyl, heterocyclyl, heteroaryl and hetroarylalkyl. $R_4$ is selected from hydrogen and a substituted or unsubstituted aryl comprising of phenyl, naphthyl, biphenyl and indanyl; heteroaryl comprising of pyridinyl, pyridazinyl, pyrimidyl, triazinyl, pyrrolyl, indolyl, pyrazolyl, imidazolyl, pyrazinyl, pyrimidinyl, tetrazolyl, furyl, thienyl, thiazolyl, isoxazolyl, oxazolyl and quinolinyl; cycloalkyl group comprising of cyclopropyl, cyclobutyl, cyclopentyl, cyclohexyl and cyclooctyl; an alkyl group comprising of methyl, ethyl, n-propyl, isopropyl, butyl, isobutyl, t-butyl, pentyl, hexyl, heptyl and octyl; haloalkyl group comprising of trichloromethyl, trifluoromethyl, difluoromethyl, trifluoroethyl, trichloroethyl, monofluoromethyl or monochloromethyl; Z is selected from hydrogen, —CH$_2$OR$_5$, —COOR$_5$, —CONR$_5$R$_6$, —NHCOOR$_5$, —NHCOR$_5$, or —NHSO$_2$R$_5$, wherein R$_5$ and R$_6$ are selected from hydrogen or substituted or unsubstituted aryl comprising phenyl, naphthyl, biphenyl and indanyl: heteroaryl comprising of pyridinyl, pyridazinyl, pyrimidyl, triazinyl, pyrrolyl, indolyl, pyrazolyl, imidazolyl, pyrazinyl, pyrimidinyl, tetrazolyl, furyl, thienyl, thiazolyl, isoxazolyl, oxazolyl and quinolinyl; cycloalkyl group comprising of cyclopropyl, cyclobutyl, cyclopentyl, cyclohexyl and cyclooctyl; an alkyl group comprising of methyl, ethyl, n-propyl, isopropyl, butyl, isobutyl, t-butyl, pentyl, hexyl, heptyl and octyl; R$_5$ and R$_6$ are optionally substituted with one or more selected from but not limited to halogens such as fluorine, chlorine, bromine, iodine; hydroxy, nitro, cyano, azido, nitroso, oxo (=O), thioxo (=S), —SO$_2$—, amino, hydrazino, formyl, alkyl, haloalkyl group such as trifluoromethyl, tribromomethyl, trichloromethyl and the like; alkoxy, haloalkoxy such as —OCH$_2$Cl and the like; arylalkoxy such as benzyloxy, phenylethoxy and the like; cycloalkyl, cycloalkyloxy, aryl, heterocyclyl, heteroaryl, alkylamino, —COOR$^a$, —C(O)R$^b$, —C(S)R$^a$, —C(O)NR$^a$R$^b$, —C(S)NR$^a$R$^b$, —NR$^a$C(O)NR$^b$R$^c$, NR$^a$C(S)NR$^b$R$^c$, —N(R$^a$)SOR$^b$, —N(R$^a$)SO$_2$R$_b$, —NR$^a$C(O)OR$^b$, —NR$^a$R$^b$, —NR$^a$C(O)R$_b$—, NR$^a$C(S)R$_b$—, —SONR$^a$R$^b$—, —SO$_2$NR$^a$R$^b$—, —OR$^a$, —OR$^a$C(O)OR$^b$—, —OC(O)NR$^a$R$^b$, OC(O)R$^a$, —OC(O)NR$^a$R$^b$—, —R$^a$NR$^b$R$^c$, —R$^a$-OR$^b$—, —SR$^a$, —SOR$^a$ or —SO$_2$R$^a$, wherein R$^a$, R$^b$ and R$^c$ are independently selected from hydrogen, or optionally substituted groups selected from alkyl, cycloalkyl, aryl, arylalkyl, heterocyclyl, heteroarylorhetroarylalkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is a single bond; X is —O—; n is 0-1; $R_1$ is selected from $C_1$-$C_8$alkyl or $C_3$-$C_8$cycloalkyl; $R_2$ is hydrogen; $R_3$ is selected from halogen, $C_1$-$C_8$ alkyl, $C_1$-$C_8$haloalkyl substituted upto 3 halogen selected from fluoro, chloro, bromo, oriodo, $C_1$-$C_8$alkoxy, $C_1$-$C_8$haloalkoxy; $C_5$-$C_{18}$arylalkoxy; $C_3$-$C_8$cycloalkyl, $C_3$-$C_8$cycloalkyloxy, $C_5$-$C_{18}$ aryl, $C_2$-$C_{18}$heterocyclyl or $C_2$-$C_{18}$heteroaryl; $R_4$ is selected from hydrogen, $C_1$-$C_8$ alkyl, $C_3$-$C_8$cycloalkyl, $C_3$-$C_8$cyloalkenyl, $C_3$-$C_8$cycloalkylalkyl, $C_5$-$C_{18}$aryl, $C_5$-$C_{18}$arylalkyl, $C_2$-$C_{18}$heterocyclyl, $C_2$-$C_{18}$heterocyclylalkyl, $C_2$-$C_{18}$heteroaryl, $C_2$-$C_{18}$ heteroarylalkyl or $C_1$-$C_8$haloalkyl, wherein alkyl, cycloalkyl, cycloalkenyl, cycloalkylalkyl, aryl, arylalkyl, heterocyclyl, heterocyclylalkyl, heteroaryl and heteroarylalkyl are independently unsubstituted or substituted with upto three substituents independently selected from halogen, alkyl, alkenyl, alkynyl, alkoxy, acyl, acyloxy, amino, hydroxy, keto, nitro, azido, cyano, amide, sulfonamide and carbamate; wherein the heterocyclyl, heterocyclylalkyl, heteroaryl and heteroarylalkyl contains upto three heteroatoms selected from O, N or S; Z is selected from the group consisting of hydrogen, —CH$_2$OR$_5$, —COOR$_5$, —CONR$_5$R$_6$, —NHCOOR$_5$, —NHCOR$_5$ or —NHSO$_2$R$_5$; wherein R$_5$ and R$_6$ are independently selected from hydrogen, hydroxyl, $C_5$-$C_{18}$aryl, $C_2$-$C_{18}$heteroaryl, $C_3$-$C_8$cycloalkyl or $C_1$-$C_8$ alkyl; wherein R$_5$ and R$_6$ are optionally substituted with one or more substituents selected fluorine, chlorine, bromine, iodine; hydroxy, nitro, cyano, azido, nitroso, oxo (=O), thioxo (=S), —SO$_2$—, amino, hydrazino, formyl, $C_1$-$C_8$ alkyl, $C_1$-$C_8$haloalkylalkoxy, $C_1$-$C_8$haloalkoxy; $C_5$-$C_{18}$arylalkoxy; $C_3$-$C_8$cycloalkyl, $C_3$-$C_8$cycloalkyloxy, $C_6$-$C_{18}$ aryl, $C_2$-$C_{18}$ heterocyclyl or $C_2$-$C_{18}$heteroaryl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is a single bond or a double bond; X is selected from —O— or —N—; n is 0-1; $R_1$ is selected from $C_1$-$C_2$ alkyl; $R_2$ and $R_3$ are independently selected from hydrogen, halogen, $C_1$-$C_8$ haloalkyl, $C_1$-$C_8$ alkoxy, and $C_1$-$C_8$ haloalkoxy; $R_4$ is selected from hydrogen, $C_1$-$C_8$alkyl, $C_2$-$C_8$alkynyl, $C_3$-$C_8$cycloalkyl, $C_3$-$C_8$cycloalkylalkyl, $C_5$-$C_{18}$aryl, $C_2$-$C_{18}$heteroaryl, or $C_1$-$C_8$haloalkyl, wherein alkyl, cycloalkyl, cycloalkylalkyl, aryl, heteroaryl and heteroarylalkyl are independently unsubstituted or substituted with upto three substituents independently selected from halogen, alkyl, and cyano, wherein the heteroaryl contains upto three heteroatoms selected from 0 or N; Z is selected from hydrogen, —$CH_2OR_5$, —$COOR_5$, —$CONR_5R_6$, —$NHCOOR_5$, — or $NHCOR_5$, wherein $R_5$ and $R_6$ are independently selected from hydrogen, $C_5$-$C_{18}$aryl, or $C_1$-$C_8$alkyl; wherein $R_5$ and $R_6$ are optionally substituted with one or more substituents selected from fluorine, chlorine, bromine, iodine, hydroxy, and cyano.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ┄┄ is a sine bond or a double bond; X is selected from —O— or —N—; n is 0-1; $R_1$ is selected from methyl and isopropyl; $R_2$ is hydrogen; $R_3$ is selected from, halogen, $C_1$-$C_2$ haloalkyl, $C_1$-$C_2$ alkoxy, and $C_1$-$C_2$ haloalkoxy; wherein haloalkyl and haloalkoxy are substituted with one or more substituents selected from fluorine and chlorine; $R_4$ is selected from hydrogen, $C_1$-$C_2$alkyl, $C_3$-$C_5$cycloalkyl, $C_3$-$C_5$cycloalkylalkyl, $C_5$-$C_6$ aryl, $C_5$-$C_6$heteroaryl, or $C_1$-$C_2$haloalkyl, wherein alkyl, cycloalkylalkyl, aryl, heteroaryl and heteroarylalkyl are independently unsubstituted or substituted with upto three substituents independently selected from halogen, alkyl, cyano amide, sulfonamide and carbamate, wherein the heteroaryl contains one heteroatom as N; Z is selected from hydrogen, —$CH_2OR_5$, —$COOR_5$, —$CONR_5R_6$, —$NHCOOR_5$, — or $NHCOR_5$, wherein $R_5$ and $R_6$ are independently selected from hydrogen, $C_6$ aryl, or $C_1$-$C_3$alkyl; wherein $C_6$ aryl is substituted with hydroxyl.

According to another embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ┄┄ is a single bond; X is —O—; n is 0-1; $R_1$ is selected from $C_1$-$C_8$ alkyl or $C_3$-$C_8$cycloalkyl; $R_2$ is hydrogen; $R_3$ is selected from halogen, $C_1$-$C_8$alkyl, $C_1$-$C_8$haloalkyl substituted upto 3 halogen selected from fluoro, chloro, bromo, oriodo, $C_1$-$C_8$alkoxy, $C_1$-$C_8$haloalkoxy; $C_5$-$C_{18}$arylalkoxy; $C_3$-$C_8$cycloalkyl, $C_3$-$C_8$cycloalkyloxy, $C_5$-$C_{18}$ aryl, $C_2$-$C_{18}$heterocyclyl or $C_2$-$C_{18}$heteroaryl; $R_4$ is selected from hydrogen, $C_1$-$C_8$ alkyl, $C_3$-$C_8$cycloalkyl, $C_5$-$C_{18}$ aryl, $C_5$-$C_{18}$arylalkyl, $C_2$-$C_{18}$heterocyclyl, $C_2$-$C_{18}$heteroaryl, $C_2$-$C_{18}$heteroarylalkyl or $C_1$-$C_8$haloalkyl, wherein alkyl, cycloalkyl, aryl, arylalkyl, heterocyclyl, heteroaryl and heteroarylalkyl are independently unsubstituted or substituted with upto three substituents independently selected from halogen, alkyl, alkenyl, alkynyl, alkoxy, acyl, acyloxy, amino, hydroxy, keto, nitro, azido, cyano; wherein the heterocyclyl, heteroaryl and heteroarylalkyl contains upto three heteroatoms selected from O, N or S; Z is selected from the group consisting of hydrogen, —$CH_2OR_5$,— $COOR_5$, —$CONR_5R_6$, —$NHCOOR_5$, —$NHCOR_5$ or —$NHSO_2R_5$; $R_5$ and $R_6$ are independently selected from hydrogen, hydroxyl, $C_5$-$C_{18}$ aryl, $C_2$-$C_{18}$heteroaryl, $C_3$-$C_8$cycloalkyl or $C_1$-$C_8$ alkyl; wherein $R_5$ and $R_6$ are optionally substituted with one or more substituents selected from fluorine, chlorine, bromine, iodine; hydroxy, nitro, cyano, azido, nitroso, oxo (=O), thioxo (=S), —$SO_2$—, amino, hydrazino, formyl, $C_1$-$C_8$ alkyl, $C_1$-$C_8$haloalkylalkoxy, $C_1$-$C_8$haloalkoxy; $C_5$-$C_{18}$arylalkoxy; $C_3$-$C_8$cycloalkyl, $C_3$-$C_8$cycloalkyloxy, $C_6$-$C_{18}$ aryl, $C_2$-$C_{18}$heterocyclyl or $C_2$-$C_{18}$heteroaryl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ┄┄ is a double bond; X is —N—; n is 0-1; $R_1$ is selected from $C_1$-$C_8$ alkyl or $C_3$-$C_8$ cycloalkyl; $R_2$ is hydrogen; $R_3$ is selected from halogen, $C_1$-$C_8$ alkyl, $C_1$-$C_8$haloalkyl substituted upto three halogen selected from fluoro, chloro, bromo, or iodo, $C_1$-$C_8$alkoxy, $C_1$-$C_8$haloalkoxy; $C_5$-$C_{18}$arylalkoxy; $C_3$-$C_8$cycloalkyl, $C_3$-$C_8$cycloalkyloxy, $C_5$-$C_{18}$ aryl, $C_2$-$C_{18}$heterocyclyl or $C_2$-$C_{18}$heteroaryl; $R_4$ is selected from hydrogen, $C_1$-$C_8$alkyl, $C_3$-$C_8$cycloalkyl, $C_3$-$C_8$cyloalkenyl, $C_3$-$C_8$ cycloalkylalkyl, $C_5$-$C_{18}$ aryl, $C_5$-$C_{18}$arylalkyl, $C_2$-$C_{18}$heterocyclyl, $C_2$-$C_{18}$heterocyclylalkyl, $C_2$-$C_{18}$heteroaryl, $C_2$-$C_{18}$heteroarylalkyl or $C_1$-$C_8$haloalkyl; wherein alkyl, cycloalkyl, cycloalkenyl, cycloalkylalkyl, aryl, arylalkyl, heterocyclyl, heterocyclylalkyl, heteroaryl and heteroarylalkyl are independently unsubstituted or substituted with upto three substituents independently selected from halogen, alkyl, alkenyl, alkynyl, alkoxy, acyl, acyloxy, amino, hydroxy, keto, nitro, azido, cyano; wherein the heterocyclyl, heterocyclylalkyl, heteroaryl and heteroarylalkyl contains upto three heteroatoms selected from O, N or S; Z is selected from the group consisting of hydrogen, —$CH_2OR_5$, —$COOR_5$, —$CONR_5R_6$, —$NHCOOR_5$, —$NHCOR_5$ or —$NHSO_2R_5$; $R_5$ and $R_6$ are independently selected from hydrogen, hydroxyl, $C_5$-$C_{18}$ aryl, $C_2$-$C_{18}$heteroaryl, $C_3$-$C_8$cycloalkyl or $C_1$-$C_8$ alkyl; wherein $R_5$ and $R_6$ are optionally substituted with, the one or more substituents are selected from but not limited to halogens such as fluorine, chlorine, bromine, iodine; hydroxy, nitro, cyano, azido, nitroso, oxo (=O), thioxo (=S), —$SO_2$—, amino, hydrazino, formyl, $C_1$-$C_8$ alkyl, $C_1$-$C_8$ haloalkylalkoxy, $C_1$-$C_8$ haloalkoxy; $C_5$-$C_{18}$ arylalkoxy; $C_3$-$C_8$ cycloalkyl, $C_3$-$C_8$ cycloalkyloxy, $C_6$-$C_{18}$ aryl, $C_2$-$C_{18}$ heterocyclyl or $C_2$-$C_{18}$ heteroaryl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ┄┄ is a double bond; X is —N—; n is 0-1; $R_1$ is selected from $C_1$-$C_8$ alkyl or $C_3$-$C_8$ cycloalkyl; $R^2$ is hydrogen; $R^3$ is selected from halogen, $C_1$-$C_8$ alkyl, $C_1$-$C_8$ haloalkyl substituted upto 3 halogen selected from fluoro, bromo, iodo, $C_1$-$C_8$ alkoxy, $C_1$-$C_8$ haloalkoxy; $C_5$-$C_{18}$ arylalkoxy; $C_3$-$C_8$ cycloalkyl, $C_3$-$C_8$ cycloalkyloxy, $C_6$-$C_{18}$ aryl, $C_2$-$C_{18}$ heterocyclyl or $C_5$-$C_{18}$ heteroaryl; $R_4$ is selected from hydrogen, $C_1$-$C_8$ alkyl, $C_3$-$C_8$ cycloalkyl, $C_5$-$C_{18}$ aryl, $C_5$-$C_{18}$ arylalkyl, $C_2$-$C_{18}$ heterocyclyl, $C_2$-$C_{18}$ heteroaryl, $C_2$-$C_{18}$heteroarylalkyl or $C_1$-$C_8$ haloalkyl; wherein alkyl, cycloalkyl, aryl, arylalkyl, heterocyclyl, heteroaryl and heteroarylalkyl are independently unsubstituted or substituted with upto three substituents independently selected from halogen, alkyl, alkenyl, alkynyl, alkoxy, acyl, acyloxy, amino, hydroxy, keto, nitro, azido, cyano; wherein the heterocyclyl, heteroaryl and heteroarylalkyl contains upto three heteroatoms selected from O, N or S; Z is selected from the group consisting of hydrogen, —$CH_2OR_5$, —$COOR_5$, —$CONR_5R_6$, —$NHCOOR_5$, or —$NHCOR_5$ wherein; $R_5$ and $R_6$ are independently selected from hydrogen, hydroxyl, $C_6$-$C_{18}$ aryl, $C_2$-$C_{18}$ heteroaryl, $C_3$-$C_8$ cycloalkyl or $C_1$-$C_8$ alkyl wherein; $R_5$ and $R_6$ are optionally substituted, with one or more substituents selected from fluorine, chlorine, bromine, iodine; hydroxy, nitro, cyano, azido, nitroso, oxo (=O), thioxo (=S), —$SO_2$—, amino, hydrazino, formyl, $C_1$-$C_8$ alkyl, $C_1$-$C_8$haloalkylalkoxy, $C_1$-$C_8$ haloalkoxy; $C_5$-$C_{18}$ arylalkoxy; $C_3$-$C_8$ cycloalkyl, $C_3$-$C_8$ cycloalkyloxy, $C_5$-$C_{18}$ aryl, $C_1$-$C_8$ heterocyclyl or $C_2$-$C_{18}$ heteroaryl.

According to another embodiment, the present disclosure relates to the compound of the Formula (Ia),

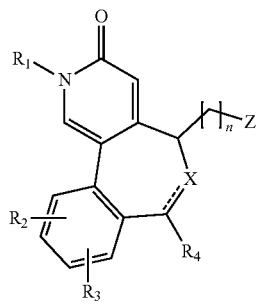

or its stereoisomers, pharmaceutically acceptable salts, complexes, hydrates, solvates, tautomers, polymorphs, racemic mixtures, optically active forms and pharmaceutically active derivative thereof, wherein X is selected from —O— or —N—; n is 0-1; R1 is selected from C1-C8 alkyl or C3-C8 cycloalkyl; R2 and R3 are independently selected from hydrogen, fluoro, chloro, bromo, iodo, hydroxy, nitro, cyano, azido, nitroso, oxo (=O), thioxo (=S), —SO2-, amino, hydrazino, formyl, C1-C8 alkyl, C1-C8haloalkyl independently substituted with upto 3 halogen selected from fluoro, chloro, bromo, or iodo, C1-C8alkoxy, C1-C8haloalkoxy; C5-C18arylalkoxy; C3-C8cycloalkyl, C3-C8cycloalkyloxy, C5-C18 aryl, C2-C18heterocyclyl, C2-C18heteroaryl, alkylamino, —COORa, —C(O)Rb, —C(S)Ra, —C(O)NRaRb, —C(S)NRaRb, —NRaC(O)NRbRc, NRaC(S)NRbRc, —N(Ra)SORb, —N(Ra)SO2Rb, —NRaC(O)ORb, —NRaRb, —NRaC(O)Rb—, NRaC(S)Rb—, —SONRaRb—, —SO2NRaRb—, —ORa, —ORaC(O)ORb—, —OC(O)NRaRb, OC(O)Ra, —OC(O)NRaRb—, —RaNRbRc, —RaORb—, —SRa, —SORa or —SO2Ra, wherein Ra, Rb and Rc are independently selected from hydrogen, C1-C8 alkyl, C3-C8cycloalkyl, C5-C18aryl, C5-C18arylalkyl, C2-C18heterocyclyl, C2-C18heteroaryl and C2-C18hetroarylalkyl. R4 is selected from hydrogen, C1-C8 alkyl, C3-C8 cycloalkyl, C6-C18aryl or C2-C18heteroaryl; wherein alkyl, cycloalkyl, aryl, and heteroaryl are independently unsubstituted or substituted with upto three substituents independently selected from halogen, alkyl, alkenyl, alkynyl, alkoxy, acyl, acyloxy, amino, hydroxy, keto, nitro, azido, cyano; wherein the heteroaryl contains upto three heteroatoms selected from O, N or S; Z is selected from —CH2OR5, —COOR5, —CONR5R6, or —CONHR7; R5 and R6 are independently selected from hydrogen, hydroxyl, C5-C18 aryl, C2-C18heteroaryl, C3-C8cycloalkyl or C1-C8 alkyl; wherein R5 and R6 are optionally substituted, with one or more substituents selected from fluorine, chlorine, bromine, iodine; hydroxy, nitro, cyano, azido, nitroso, oxo (=O), thioxo (=S), —SO2-, amino, hydrazino, formyl, C1-C8 alkyl, C1-C8 haloalkylalkoxy, C1-C8 haloalkoxy; C5-C18 arylalkoxy; C3-C8 cycloalkyl, C3-C8 cycloalkyloxy, C5-C18 aryl, C2-C18 heterocyclyl, C2-C18 heteroaryl, alkylamino, —COORa, —C(O)Rb, —C(S)Ra, —C(O)NRaRb, —C(S)NRaRb, —NRaC(O)NRbRc, NRaC(S)NRbRc, —N(Ra)SORb, —N(Ra)SO2Rb, —NRaC(O)ORb, —NRaRb, —NRaC(O)Rb—, NRaC(S)Rb—, —SONRaRb—, —SO2NRaRb—, —ORa, —ORaC(O)ORb—, —OC(O)NRaRb, OC(O)Ra, —OC(O)NRaRb—, —RaNRbRc, —RaORb—,—SRa, —SORa or —SO2Ra, wherein Ra, Rb and Rc are independently selected from hydrogen, or optionally substituted groups selected from alkyl, cycloalkyl, aryl, arylalkyl, heterocyclyl, heteroarylorhetroarylalkyl. R7 represents —OR8, ortho substituted aniline, amino aryl and amino heteroaryl, which may be further substituted, wherein R8 is selected from hydrogen, optionally substituted groups selected from alkyl, aryl, heterocyclyl and —COR9, wherein R9 is selected from alkyl, aryl, heteroaryl, cycloalkyl or heterocyclyl.

According to an embodiment, the present disclosure relates to a compound of Formula Ia

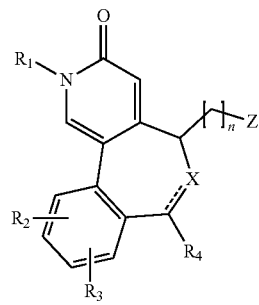

(Ia)

their analogs, tautomeric forms, stereoisomers, polymorphs, solvates, intermediates, pharmaceutically acceptable salts, pharmaceutical compositions, metabolites and prodrugs thereof which can be used for the treatment of proliferative diseases; wherein, $R_1$ represents substituted or unsubstituted alkyl or cycloalkyl; X represents —O— or —N—; $R_4$ represent hydrogen or substituted or unsubstituted aryl, heteroaryl, cycloalkyl and alkyl; Z represents —$CH_2OR_5$, —$COOR_5$ or —$CONR_5R_6$, —$CONHR_7$; $R_5$ and $R_6$ represent hydrogen or substituted or unsubstituted aryl, heteroaryl, cycloalkyl and alkyl; $R_7$ represents —$OR_8$, ortho substituted aniline, amino aryl and amino heteroaryl, which may be further substituted, wherein R represents hydrogen, optionally substituted groups selected from alkyl, aryl, heterocyclyl and —$COR_9$, wherein $R_9$ represents optionally substituted groups selected from alkyl, aryl, heteroaryl, cycloalkyl and heterocyclyl; n represents an integer from 0-6; $R_2$ and $R_3$ represent substitution which are independently selected from hydrogen, be one or more are selected from but not limited to halogens such as fluorine, chlorine, bromine, iodine; hydroxy, nitro, cyano, azido, nitroso, oxo (=O), thioxo (=S), —$SO_2$—, amino, hydrazino, formyl, alkyl, haloalkyl group such as trifluoromethyl, tribromomethyl, trichloromethyl and the like; alkoxy, haloalkoxy such as —$OCH_2Cl$ and the like; arylalkoxy such as benzyloxy, phenylethoxy and the like; cycloalkyl, cycloalkyloxy, aryl, heterocyclyl, heteroaryl, alkylamino, —$COOR_a$, —$C(O)R_b$, —$C(S)R_a$, —$C(O)NR^aR_b$, —$C(S)NR_aR_b$, —$NR_aC(O)NR_bR_c$, $NR_a$ $C(S)NR_bR_c$, —$N(R_a)SOR_b$, —$N(R_a)SO_2R_b$, —$NR_aC(O)$ $OR_b$, —$NR_aR_b$, —$NR_aC(O)R_b$—, $NR_aC(S)R_b$—, —$SON$-$R_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ in each of the above groups can be hydrogen, optionally substituted groups selected from alkyl, cycloalkyl, aryl, arylalkyl, heterocyclyl, heteroaryl and hetroarylalkyl. The substituents are optionally further substituted by one or more substituents as defined above.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_1$ is methyl or iso-propyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_2$ is hydrogen.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_3$ is selected from $C_1$-$C_8$alkoxy, $C_1$-$C_8$haloalkyl, halogen or $C_1$-$C_8$ haloalkoxy.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_3$ is selected from methoxy, trifluoromethyl, fluorine, or difluoromethoxy.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, R is selected from C1 alkyl, $C_3$cycloalkyl, $C_6$ cycloalkyl $C_3$cycloalkylalkyl, $C_6$ aryl, $C_5$heteroaryl, or $C_1$ haloalkyl, wherein alkyl, cycloalkylalkyl, aryl, heteroaryl and heteroarylalkyl are independently unsubstituted or substituted with upto three substituents independently selected from fluorine, chlorine, methyl and cyano, wherein the heteroaryl contains one heteroatom as N.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, X is —N—.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, X is —O—.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, n is 1.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, which is selected from a group consisting of:

1) ±Ethyl-2-(-7-(4-chlorophenyl)-9-methoxy-2-methyl-3-oxo-2,3,5,7-tetrahydrobenzo[5,6]oxepino[4,3-c]pyridin-5-yl)acetate
1A) Ethyl 2-((5S,7R)-(4-chlorophenyl)-9-methoxy-2-methyl-3-oxo-2,3,5,7-tetrahydrobenzo[5,6]oxepino[4,3-c]pyridin-5-yl)acetate
1B) Ethyl 2-((5S,7S)-(4-chlorophenyl)-9-methoxy-2-methyl-3-oxo-2,3,5,7-tetrahydrobenzo[5,6]oxepino[4,3-c]pyridin-5-yl)acetate
1C) Ethyl 2-((5R,7S)-(4-chlorophenyl)-9-methoxy-2-methyl-3-oxo-2,3,5,7-tetrahydrobenzo[5,6]oxepino[4,3-c]pyridin-5-yl)acetate
1D) Ethyl 2-((5R,7R)-(4-chlorophenyl)-9-methoxy-2-methyl-3-oxo-2,3,5,7-tetrahydrobenzo[5,6]oxepino[4,3-c]pyridin-5-yl)acetate
2) ±Ethyl-2-(7-cyclohexyl-9-methoxy-2-methyl-3-oxo-2,3,5,7-tetrahydrobenzo[5,6]oxepino[4,3-c]pyridin-5-yl)acetate
3) ±Ethyl-2-(7-(cyclopropylmethyl)-9-methoxy-2-methyl-3-oxo-2,3,5,7-tetrahydrobenzo[5,6]oxepino[4,3-c]pyridin-5-yl)acetate
4) ±Ethyl-2-(9-methoxy-2-methyl-7-(5-methylpyridin-2-yl)-3-oxo-2,3,5,7-tetrahydrobenzo[5,6]oxepino[4,3-c]pyridin-5-yl)acetate
5) ±Ethyl-2-(7-(4-chlorophenyl)-9-fluoro-2-methyl-3-oxo-2,3,5,7-tetrahydrobenzo[5,6]oxepino[4,3-c]pyridin-5-yl)acetate
6) ±Ethyl-2-(7-(4-chlorophenyl)-2-methyl-3-oxo-9-(trifluoromethyl)-2,3,5,7-tetrahydrobenzo[5,6]oxepino[4,3-c]pyridin-5-yl)acetate
7) ±7-(4-chlorophenyl)-5-(2-hydroxyethyl)-9-methoxy-2-methyl-5,7-dihydrobenzo[5,6]oxepino[4,3-c]pyridin-3(2H)-one
8) ±2-(-7-(4-chlorophenyl)-9-methoxy-2-methyl-3-oxo-2,3,5,7-tetrahydrobenzo[5,6]oxepino[4,3-c]pyridin-5-yl)-N-ethylacetamide
8A) ±2-((5S,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide
8B) ±2-((5S,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide
8C) 2-((5S,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide
8D) 2-((5S,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide
8E) 2-((5R,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide
8F) 2-((5R,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide
9) ±2-(7-cyclohexyl-9-methoxy-2-methyl-3-oxo-2,3,5,7-tetrahydrobenzo[5,6]oxepino[4,3-c]pyridin-5-yl)-N-ethylacetamide
9A) ±2-((5S,7R)-7-cyclohexyl-9-methoxy-2-methyl-3-oxo-2,3,5,7-tetrahydrobenzo[5,6]oxepino[4,3-c]pyridin-5-yl)-N-ethylacetamide
9B) ±2-((5S,7S)-7-cyclohexyl-9-methoxy-2-methyl-3-oxo-2,3,5,7-tetrahydrobenzo[5,6]oxepino[4,3-c]pyridin-5-yl)-N-ethylacetamide
10) ±2-(7-(cyclopropylmethyl)-9-methoxy-2-methyl-3-oxo-2,3,5,7-tetrahydrobenzo[5,6]oxepino[4,3-c]pyridin-5-yl)-N-ethylacetamide
10A) ±2-((5S,7R)-7-(cyclopropylmethyl)-9-methoxy-2-methyl-3-oxo-2,3,5,7-tetrahydrobenzo[5,6]oxepino[4,3-c]pyridin-5-yl)-N-ethylacetamide 10B) ±2-((5S,7S)-7-(cyclopropylmethyl)-9-methoxy-2-methyl-3-oxo-2,3,5,7-tetrahydrobenzo[5,6]oxepino[4,3-c]pyridin-5-yl)-N-ethylacetamide
11) ±2-(9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide
11A) ±2-((5S,7S)-9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide
11B) ±2-((5S,7R)-9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide
12) ±2-(7-(4-chlorophenyl)-9-fluoro-2-methyl-3-oxo-2,3,5,7-tetrahydrobenzo[5,6]oxepino[4,3-c]pyridin-5-yl)-N-ethylacetamide
12A) ±2-((5S,7R)-9-fluoro-2-methyl-3-oxo-7-phenyl-2,3,5,7-tetrahydrobenzo[5,6]oxepino[4,3-c]pyridin-5-yl)-N-ethylacetamide
12B) ±2-((5S,7S)-9-fluoro-2-methyl-3-oxo-7-phenyl-2,3,5,7-tetrahydrobenzo[5,6]oxepino[4,3-c]pyridin-5-yl)-N-ethylacetamide
13) ±2-(7-(4-chlorophenyl)-2-methyl-3-oxo-9-(trifluoromethyl)-2,3,5,7-tetrahydrobenzo[5,6]oxepino[4,3-c]pyridin-5-yl)-N-ethylacetamide
13A) ±2-((5S,7R)-2-methyl-3-oxo-7-phenyl-9-(trifluoromethyl)-2,3,5,7-tetrahydrobenzo[5,6]oxepino[4,3-c]pyridin-5-yl)-N-ethylacetamide
13B) ±2-((5S,7S)-2-methyl-3-oxo-7-phenyl-9-(trifluoromethyl)-2,3,5,7-tetrahydrobenzo[5,6]oxepino[4,3-c]pyridin-5-yl)-N-ethylacetamide
14) ±Ethyl-2-(7-(4-chlorophenyl)-9-methoxy-2-methyl-3-oxo-3,5-dihydro-2H-benzo[c]pyrido[3,4-e]azepin-5-yl)acetate
15) ±Ethyl 2-(7-cyclohexyl-9-methoxy-2-methyl-3-oxo-3,5-dihydro-2H-benzo[c]pyrido[3,4-e]azepin-5-yl)acetate
16) ±Ethyl-2-(9-methoxy-2-methyl-3-oxo-7-(pyridin-2-yl)-3,5-dihydro-2H-benzo[c]pyrido[3,4-e]azepin-5-yl)acetate
17) ±Ethyl-2-(7-(cyclopropylmethyl)-9-methoxy-2-methyl-3-oxo-3,5-dihydro-2H-benzo[c]pyrido[3,4-e]azepin-5-yl)acetate
18) ±Ethyl-2-(9-methoxy-2-methyl-3-oxo-7-(trifluoromethyl)-3,5-dihydro-2H-benzo[c]pyrido[3,4-e]azepin-5-yl)acetate
19) ±Ethyl-2-(9-methoxy-2,7-dimethyl-3-oxo-3,5-dihydro-2H-benzo[c]pyrido[3,4-e]azepin-5-yl)acetate
20) ±Ethyl-2-(9-methoxy-2-methyl-7-(5-methylpyridin-2-yl)-3-oxo-3,5-dihydro-2H-benzo[c]pyrido[3,4-e]azepin-5-yl)acetate
21) ±Ethyl-2-(7-(4-chlorophenyl)-2-isopropyl-9-methoxy-3-oxo-3,5-dihydro-2H-benzo[c]pyrido[3,4-e]azepin-5-yl)acetate
22) ±Ethyl-2-(7-(4-chlorophenyl)-9-fluoro-2-methyl-3-oxo-3,5-dihydro-2H-benzo[c]pyrido[3,4-e]azepin-5-yl)acetate
23) ±Ethyl-2-(7-(2,6-difluorophenyl)-9-methoxy-2-methyl-3-oxo-3,5-dihydro-2H-benzo[c]pyrido[3,4-e]azepin-5-yl)acetate
24) ±Ethyl-2-(7-(4-chloro-2-methylphenyl)-9-methoxy-2-methyl-3-oxo-3,5-dihydro-2H-benzo[c]pyrido[3,4-e]azepin-5-yl)acetate
25) ±2-(7-(4-chlorophenyl)-9-methoxy-2-methyl-3-oxo-3,5-dihydro-2H-benzo[c]pyrido[3,4-e]azepin-5-yl)-N-ethylacetamide
25A) (S)-2-(7-(4-chlorophenyl)-9-methoxy-2-methyl-3-oxo-3,5-dihydro-2H-benzo[c]pyrido[3,4-e]azepin-5-yl)-N-ethylacetamide.
25B) (R)-2-(7-(4-chlorophenyl)-9-methoxy-2-methyl-3-oxo-3,5-dihydro-2H-benzo[c]pyrido[3,4-e]azepin-5-yl)-N-ethylacetamide.
26) ±2-(7-cyclohexyl-9-methoxy-2-methyl-3-oxo-3,5-dihydro-2H-benzo[c]pyrido[3,4-e]azepin-5-yl)-N-ethylacetamide
26A) (S)-2-(7-cyclohexyl-9-methoxy-2-methyl-3-oxo-3,5-dihydro-2H-benzo[c]pyrido[3,4-e]azepin-5-yl)-N-ethylacetamide
26B) (R)-2-(7-cyclohexyl-9-methoxy-2-methyl-3-oxo-3,5-dihydro-2H-benzo[c]pyrido[3,4-e]azepin-5-yl)-N-ethylacetamide
27) ±2-(9-methoxy-2-methyl-3-oxo-7-(pyridin-2-yl)-3,5-dihydro-2H-benzo[c]pyrido[3,4-e]azepin-5-yl)-N-ethylacetamide
27A) (S)-2-(9-methoxy-2-methyl-3-oxo-7-(pyridin-2-yl)-3,5-dihydro-2H-benzo[c]pyrido[3,4-e]azepin-5-yl)-N-ethylacetamide
27B) (R)-2-(9-methoxy-2-methyl-3-oxo-7-(pyridin-2-yl)-3,5-dihydro-2H-benzo[c]pyrido[3,4-e]azepin-5-yl)-N-ethylacetamide
28) ±2-(7-(4-chlorophenyl)-9-methoxy-2-methyl-3-oxo-3,5-dihydro-2H-benzo[c]pyrido[3,4-e]azepin-5-yl)acetamide
29) ±2-(7-(4-chlorophenyl)-9-hydroxy-2-methyl-3-oxo-3,5-dihydro-2H-benzo[c]pyrido[3,4-e]azepin-5-yl)-N-ethylacetamide
30) ±2-(7-(cyclopropylmethyl)-9-methoxy-2-methyl-3-oxo-3,5-dihydro-2H-benzo[c]pyrido[3,4-e]azepin-5-yl)-N-ethylacetamide
30A) (S)-2-(7-(cyclopropylmethyl)-9-methoxy-2-methyl-3-oxo-3,5-dihydro-2H-benzo[c]pyrido[3,4-e]azepin-5-yl)-N-ethylacetamide
30B) (R)-2-(7-(cyclopropylmethyl)-9-methoxy-2-methyl-3-oxo-3,5-dihydro-2H-benzo[c]pyrido[3,4-e]azepin-5-yl)-N-ethylacetamide
31) ±2-(7-(4-chlorophenyl)-9-(difluoromethoxy)-2-methyl-3-oxo-3,5-dihydro-2H-benzo[c]pyrido[3,4-e]azepin-5-yl)-N-ethylacetamide
32) ±2-(9-methoxy-2-methyl-3-oxo-7-(trifluoromethyl)-3,5-dihydro-2H-benzo[c]pyrido[3,4-e]azepin-5-yl)-N-ethylacetamide
32A) (S)-2-(9-methoxy-2-methyl-3-oxo-7-(trifluoromethyl)-3,5-dihydro-2H-benzo[c]pyrido[3,4-e]azepin-5-yl)-N-ethylacetamide
32B) (R)-2-(9-methoxy-2-methyl-3-oxo-7-(trifluoromethyl)-3,5-dihydro-2H-benzo[c]pyrido[3,4-e]azepin-5-yl)-N-ethylacetamide
33) ±2-(7-(4-cyanophenyl)-9-methoxy-2-methyl-3-oxo-3,5-dihydro-2H-benzo[c]pyrido[3,4-e]azepin-5-yl)-N-ethylacetamide
34) ±2-(9-methoxy-2-methyl-7-(5-methylpyridin-2-yl)-3-oxo-3,5-dihydro-2H-benzo[c]pyrido[3,4-e]azepin-5-yl)-N-ethylacetamide
35) ±2-(7-(4-chlorophenyl)-2-methyl-3-oxo-9-(trifluoromethyl)-3,5-dihydro-2H-benzo[c]pyrido[3,4-e]azepin-5-yl)-N-ethylacetamide
36) ±2-(7-(4-chlorophenyl)-2-isopropyl-9-methoxy-3-oxo-3,5-dihydro-2H-benzo[c]pyrido[3,4-e]azepin-5-yl)-N-ethylacetamide
37) ±2-(7-(4-chlorophenyl)-9-fluoro-2-methyl-3-oxo-3,5-dihydro-2H-benzo[c]pyrido[3,4-e]azepin-5-yl)-N-ethylacetamide
38) ±2-(7-(2,6-difluorophenyl)-9-methoxy-2-methyl-3-oxo-3,5-dihydro-2H-benzo[c]pyrido[3,4-e]azepin-5-yl)-N-ethylacetamide 39) ±2-(7-(4-chloro,2-methylphenyl)-9-methoxy-2-methyl-3-oxo-3,5-dihydro-2H-benzo[c]pyrido[3,4-e]azepin-5-yl)-N-ethylacetamide
40) ±2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide
40A) (S)-2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide
40B) (R)-2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide
41) ±7-(4-chlorophenyl)-9-methoxy-2,5-dimethyl-2H-benzo[c]pyrido[3,4-e]azepin-3(5H)-one
41A) (S)-7-(4-chlorophenyl)-9-methoxy-2,5-dimethyl-2H-benzo[c]pyrido[3,4-e]azepin-3(5H)-one
41B) (R)-7-(4-chlorophenyl)-9-methoxy-2,5-dimethyl-2H-benzo[c]pyrido[3,4-e]azepin-3(5H)-one
42) ±7-(4-chlorophenyl)-9-methoxy-2-methyl-2H-benzo[c]pyrido[3,4-e]azepin-3(5H)-one
43) ±2-(7-(4-chlorophenyl)-2-methyl-3-oxo-9-(trifluoromethyl)-3,5-dihydro-2H-benzo[c]pyrido[3,4-e]azepin-5-yl)acetic acid
44) ±2-(7-(4-chlorophenyl)-9-methoxy-2-methyl-3-oxo-3,5-dihydro-2H-benzo[c]pyrido[3,4-e]azepin-5-yl)acetic acid
45) ±tert-butyl((7-(4-chlorophenyl)-9-methoxy-2-methyl-3-oxo-3,5-dihydro-2H-benzo[c]pyrido[3,4-e]azepin-5-yl))methyl)carbamate
46) ±N-((7-(4-chlorophenyl)-9-methoxy-2-methyl-3-oxo-3,5-dihydro-2H-benzo[c]pyrido[3,4-e]azepin-5-yl)methyl)acetamide According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a pharmaceutical composition including a compound of Formula (I), or its stereoisomers, pharmaceutically acceptable salts, complexes, hydrates, solvates, tautomers, polymorphs, racemic mixtures, optically active forms and pharmaceutically active derivative thereof, and at least one pharmaceutically acceptable carrier, diluent, or excipient.

According to an embodiment, the present disclosure relates to the use of a compound of Formula (I) or (Ia) and pharmaceutical composition including a compound of Formula (I) or (Ia), or its stereoisomers, pharmaceutically acceptable salts, complexes, hydrates, solvates, tautomers, polymorphs, racemic mixtures, optically active forms and pharmaceutically active derivative thereof, in the manufacture of a medicament for the treatment and/or prevention of diseases and/or disorders in which aberrant, abnormal or deregulated activity of BET family of bromodomain containing proteins; in particular BRD2, BRD3, BRD4 and BRDT proteins.

According to an embodiment, the present disclosure relates to the use of a compound of Formula (I) or (Ia) and pharmaceutical composition including a compound of Formula (I) or (Ia) or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an anti-cancer effect in a warm-blooded animal such as man.

According to an embodiment, the present disclosure relates to a method for treating a variety of diseases or conditions related to systemic or tissue inflammation, inflammatory responses to infection or hypoxia, cellular activation and proliferation, lipid metabolism, fibrosis and in the prevention and treatment of viral infections.

According to an embodiment, the present disclosure relates to a method for treating cancer in patients including administration of a therapeutically effective amount of a compound of Formula (I).

According to an embodiment, the present disclosure relates to a method for treating proliferative conditions or cancer, comprising administering to a subject suffering from proliferative conditions or cancer, a therapeutically effective amount of a compound of Formula (I), in the presence or absence of other clinically relevant cytotoxic agents or non-cytotoxic agents to a mammal in need thereof.

According to an embodiment, the present disclosure relates to a method for treating a disorder caused by, associated with or accompanied by disruptions of cell proliferation and/or angiogenesis and the subsequent metastasis including administration of a therapeutically effective amount of a compound of Formula (I).

According to an embodiment, the present disclosure relates to a method for treating cancer in patient including administration of effective amount of compounds of formula (I). The cancer can be either a hematologic malignancy or solid tumor. Hematological malignancy is selected from the group consisting of B-cell lymphoma, T-cell lymphoma and leukemia. In the case of solid tumors, the tumors are selected from the group consisting of breast cancer, lung cancer, ovarian cancer, prostate cancer, head cancer, neck cancer, renal cancer, gastric cancer, colon cancer, pancreatic cancer and brain cancer.

According to an embodiment, the present disclosure relates to a method for treating and/or preventing a neurodegenerative disease or disorder comprising administering, to a patient in need of treatment, a therapeutically effectively amount of a composition comprising a compound of Formula I and a pharmaceutically acceptable carrier.

In one aspect of this embodiment, the invention provides a compound of Formula I for use in treating and/or preventing a neurodegenerative disorder or condition. In a related aspect, the invention provides for the use of a compound of Formula I for the manufacture of a medicament for treating and/or preventing a neurodegenerative disorder or condition.

According to an embodiment, the present disclosure relates to the compounds of Formula (I) useful for treating proliferative diseases. A proliferative disease includes, for example, a tumor disease and/or metastates.

According to an embodiment, the compounds of the present disclosure are useful for treating a proliferative disease that is refractory to the treatment with other chemotherapeutics; or a tumor that is refractory to treatment with other therapeutics due to multidrug resistance.

According to an embodiment, the present disclosure relates to a method of treatment of cancer, said method comprising administering a combination of the compound or the pharmaceutical composition with other clinically relevant immune modulators agents to a mammal in need of thereof.

According to an embodiment, the compounds of the present invention are able to slow tumor growth, stop tumor growth or bring about the regression of tumors and to prevent the formation of tumor metastasis (including micrometastatis) and the growth of metastates (including micrometastatis). In addition they can be used in epidermal hyper proliferation.

The compound of formula I of the present invention can be used as a prophylactic or therapeutic agent for cancer. Examples of the cancer not restricted include breast cancer, prostate cancer, pancreatic cancer, gastric cancer, lung cancer, colon cancer, rectal cancer, esophagus cancer, duodenal cancer, tongue cancer, pharyngeal cancer, brain tumor, neurinoma, non-small cell lung cancer, small cell lung cancer, liver cancer, kidney cancer, bile duct cancer, uterine body cancer, cervical cancer, ovarian cancer, urinary bladder, skin cancer, hemangioma, malignant lymphoma, malignant melanoma, thyroid cancer, bone tumor, vascular fibroma, retinoblastoma, penile cancer, pediatric solid cancer, lymphoma, myeloma and leukemia (including, for example acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL) or hairy cell leukemia).

The compound of formula I of the present invention can be used as a prophylactic or therapeutic agent for various chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

In one embodiment, the invention provides a method of inhibiting bromodomain activity comprising administering, to a patient in need of treatment, an amount of a composition comprising a compound of Formula I and a pharmaceutically acceptable carrier sufficient to inhibit bromodomain activity.

In one aspect of this embodiment, the invention provides a compound of Formula I for use in inhibiting bromodomain. In a related aspect, the invention provides for the use of a compound of Formula I for the manufacture of a medicament for inhibiting bromodomain.

In one embodiment, the invention provides a method of treating and/or preventing a neurodegenerative disease or disorder comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing a neurodegenerative disorder or condition. In a related aspect, the invention provides for the use of a compound of Formula I for the manufacture of a medicament for treating and/or preventing a neurodegenerative disorder or condition.

In another aspect, the compound may be administered in combination therapy by combining the compound of formula (I) with one or more separate agents, not limited to targets such as DNA methyltransferase, heat shock proteins (e.g. HSP90) kinases and other matrix metalloproteinases.

"Combination therapy" includes the administration of the subject compounds in further combination with other biologically active ingredients (such as vinblastine, afatinib, nilotinib, vemarafinib, aflibercept, axitinib, dasatinib, sorafenib, bosutinib, crizotinib, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of the invention. The compounds can be administered simultaneously or sequentially to the other drug therapy.

In another aspect, the subject compounds may be combined with the antineoplastic agents (e.g. small molecules, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In another aspect, the subject compounds may be combined with immunoncology drugs not restricting to PDL-1 inhibitor, IDO, TDO, CTLA4 or any other drugs which is involved in the immune modulation.

A term once described, the same meaning applies for it, throughout the patent.

Scheme:

According to an embodiment, the present disclosure relates to a process as shown in the following scheme-, for the preparation of compounds of the Formula (I), wherein all the groups are as defined earlier.

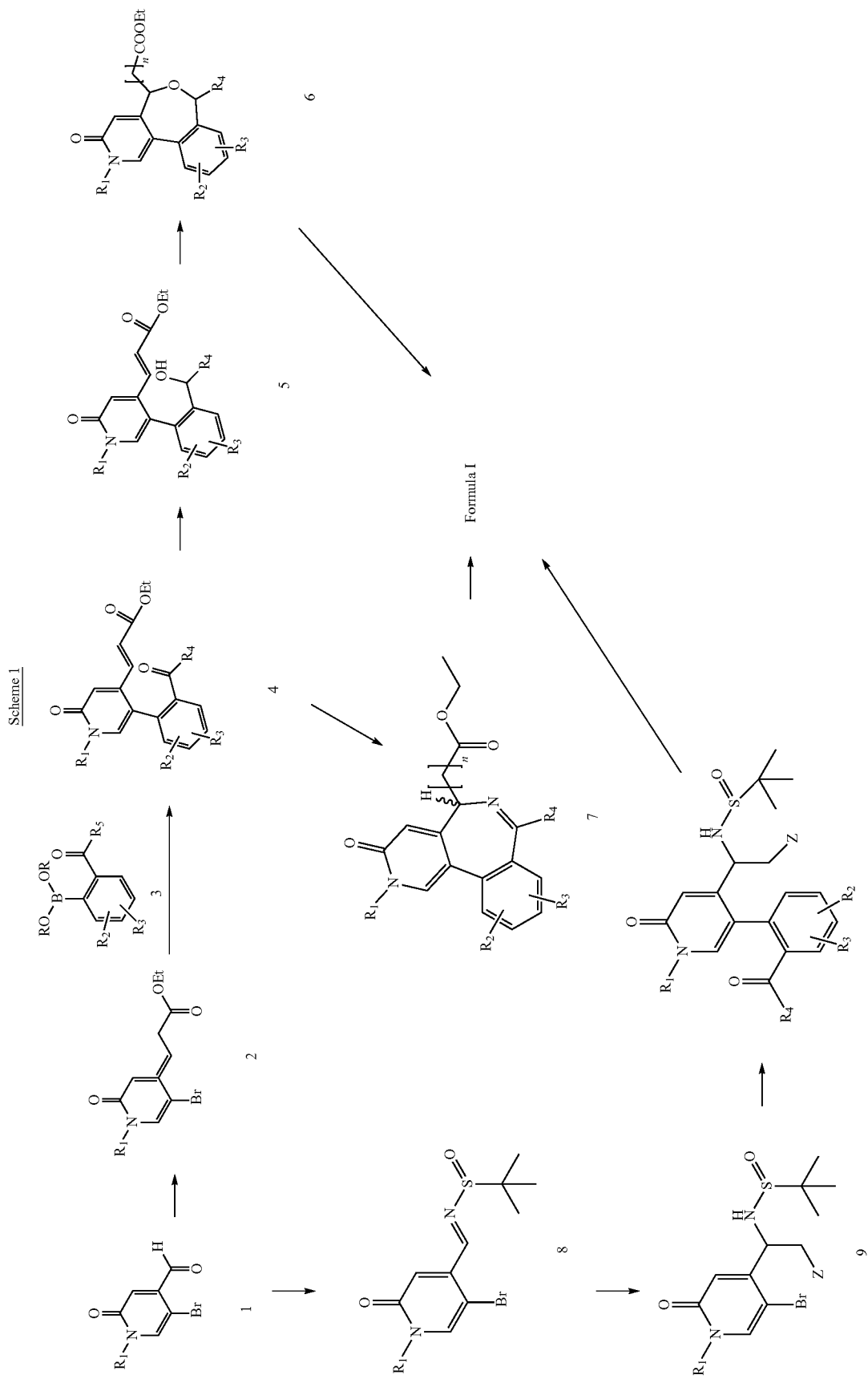

The Said Process for the Preparation of the Compounds of Formula (I) Comprises of the Following:

The compound 1 was converted to compound 2 under standard conditions either using malonic acid or witting reagent. Compound 2 was treated with intermediate 3 in the presence of Pd catalyst C—C bond formation under standard conditions to obtained 4. Compound 4 under standard carbonyl reductions using sodium borohydride or sodium cyanoborohydride or like to give the corresponding alcohol 5. Intramolecular cyclization of 5 using bases such as inorganic or organic bases gives 6. Further exploration of 6 gives compound of formula 1. Treating compound 4 with ammonium formate or ammonium acetate or the like in polar protic solvent such as methanol, ethanol or the like gives 7. Further exploration of 7 gives compound of formula 1. Compound 1 can be converted to compound 8 by treating corresponding sulfoximine. Compound 8 when treated with appropriately substituted Grignard reagent in the presence of suitable solvents such as tetrahydrofuran or dioxane or diethylether gave compound 9. Compound 9 on treatment with acids such as HCl, $H_2SO_4$ and the like gave compound of formula 1. Where in $R^1$, $R^2$, $R^3$, $R^4$ and Z are described above. The examples given below are provided by the way of illustration only and therefore should not be construed to limit the scope of the invention.

EXAMPLES

The following examples provide the details about the synthesis, activities, and applications of the compounds of the present disclosure. It should be understood the following is representative only, and that the invention is not limited by the details set forth in these examples.

Example 1

±Ethyl 2-(-7-(4-chlorophenyl)-9-methoxy-2-methyl-3-oxo-2,3, 5,7-tetrahydrobenzo[5,6]oxepino[4,3-c]pyridin-5-yl) acetate

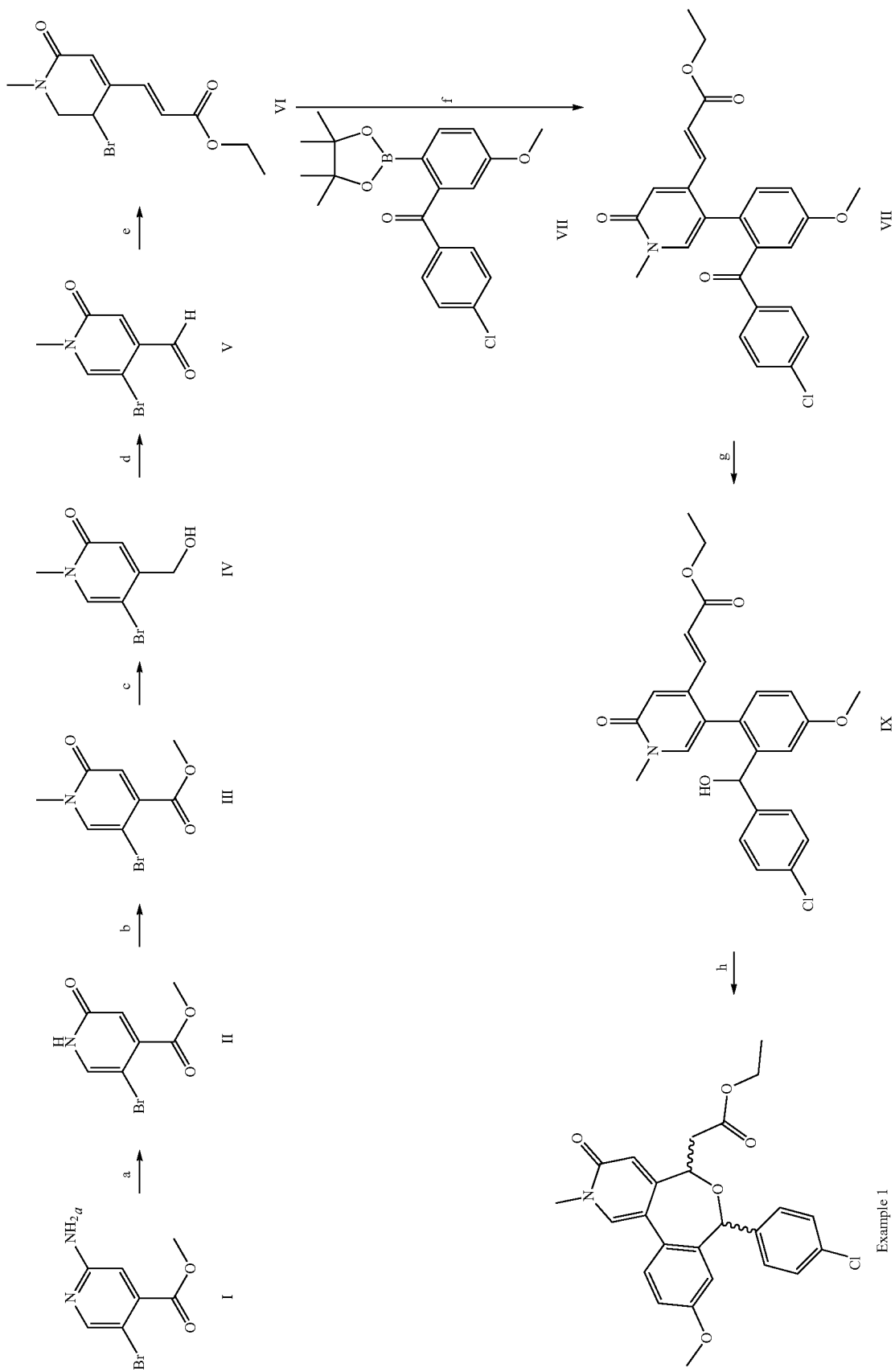

Step A: methyl 5-bromo-2-oxo-1,2-dihydropyridine-4-carboxylate-II

To a stirred solution of Conc. $H_2SO_4$ (50 mL, 0.668 mol) in water (500 mL) was added methyl 2-amino-5-bromoisonicotinate (I, 50 g, 0.226 mol). The resulting clear brown solution was cooled to 0° C. To the mixture was added $NaNO_2$ (50 g, 0.668 mmol) in water (150 mL) drop wise using addition funnel at 0° C. Vigorous effervescence with evolution of $N_2$ gas was observed. The reaction mixture was warmed to room temperature. The reaction mixture was stirred for additional 30 min at room temperature. The solid was filtered, washed with water (3×150 mL) followed by n-hexane (2×100 mL) to yield as a yellow solid. (48.0 g, 93% yield). $^1H$ NMR (DMSO-$d_6$, 400 MHz), δ (ppm): 7.62 (s, 1H), 6.90 (s, 1H), 5.0 (br, 1H), 3.98 (s, 3H). MS (ESI): mass calcd. for $C_7H_7BrN_2O_2$, 232.01; m/z found, 234[M+2H]$^+$.

Step B: methyl 5-bromo-1-methyl-2-oxo-1,2-dihydropyridine-4-carboxylate-III

To a stirred solution of methyl 5-bromo-2-oxo-1,2-dihydropyridine-4-carboxylate (II, 25.0 g, 0.107 mol) in acetonitrile (500 mL) was added cesium carbonate (42 g, 0.129 mol) at 5-10° C. To this mixture was added methyl iodide (7.4 mL, 0.118 mol). The reaction mixture was warmed to room temperature and stirred for 4 h. The reaction mixture was filtered and concentrated to get the product as a brown solid. (25 g, 95% yield), $^1H$ NMR (DMSO-$d_6$, 400 MHz): δ (ppm): 8.18 (s, 1H), 6.70 (s, 1H), 3.83 (s, 3H), 3.42 (s, 3H). MS (ESI): mass calcd. for $C_8H_8BrNO_3$, 246.01; m/z found, 248[M+2H]$^+$.

Step C: 5-bromo-4-(hydroxymethyl)-1-methylpyridin-2(1H)-one-IV

To the 5-bromo-4-(hydroxymethyl)-1-methylpyridin-2(1H)-one (III, 24.0 g, 0.096 mol) was added THF (250 mL), DME (250 mL) and $NaBH_4$ (10 g, 0.213 mol) at room temperature. The reaction mixture was heated to 75-80° C. To the reaction mixture was added slowly MeOH (250 mL) using additional funnel. The reaction mixture was stirred at 70-75° C. for 1 h. The reaction mixture was concentrated under reduced pressure. The concentrate was triturated with 50 mL of water and filtered to yield as a pale yellowish solid. (15.0 g, 71% yield), $^1H$ NMR (DMSO-$d_6$, 400 MHz): δ (ppm): 7.98 (s, 1H), 6.44 (s, 1H), 5.56 (br, 1H), 4.29 (s, 2H), 3.38 (s, 3H). MS (ESI): mass calcd. for $C_7H_8BrNO_2$, 218.05; m/z found, 220 [M+2H]$^+$.

Step D: 5-bromo-1-methyl-2-oxo-1,2-dihydropyridine-4-carbaldehyde-V

To the 5-bromo-4-(hydroxymethyl)-1-methylpyridin-2(1H)-one. (IV, 20.0 g, 0.091 mol) was added acetonitrile (2 L) and stirred at room temperature for 30 mins to get a slightly turbid mixture. To this mixture, Dess-martin-periodinane reagent (60 g, 0.137 mol) was added at room temperature. The resulting turbid milky suspension was stirred at room temperature for 3 h. To the reaction mixture was added saturated sodiumbicarbonate aqueous solution (50 mL) and stirred for 15 min. The reaction mixture was filtered over celite bed. The celite bed was washed with 100 mL of acetonitrile. The acetonitrile organic layer was concentrated 1/3$^{rd}$ portion to get a turbid mixture again. The turbid mixture was filtered over celite bed once again and washed with 100 mL of acetonitrile. The acetonitrile organic layer was concentrated to dryness. The residue was dissolved in 5% MeOH in DCM (250 mL) and washed with 50 mL of water. The organic layer was concentrated to get the title compound 5-bromo-1-methyl-2-oxo-1,2-dihydropyridine-4-carbaldehyde as a semi solid (12.3 g, 62% yield), $^1H$ NMR (DMSO-$d_6$, 400 MHz): δ (ppm): 9.94 (s, 1H), 8.23 (s, 1H), 6.81 (s, 1H), 3.45 (s, 3H). MS (ESI): mass calcd. for $CH_6BrNO_2$, 216.03; m/z found, 218[M+2H]$^+$.

Step E: (E)-ethyl 3-(5-bromo-1-methyl-2-oxo-1,2-dihydropyridin-4-yl)acrylate-VI To a suspension of NaH (2.6 g, 0.064 mol) in dry THF (100 mL) at 0° C. was added portion wise triethylphosphonoacetate (12 mL, 0.06 mol) under nitrogen atmosphere. The reaction mixture was stirred for 30 min at 0° C. to get a clear solution. To the mixture, 5-bromo-1-methyl-2-oxo-1,2-dihydropyridine-4-carbaldehyde (V, 10 g, 0.046 mol) in DMSO (50 mL) was added under inert atmosphere. The reaction mixture was warmed to room temperature and stirred for 1 h. The reaction mixture was quenched with aq. $NH_4Cl$ solution (20 mL), extracted with EtOAc (100 mL×2 times). The combined organic layer was washed with ice cold water 100 mL. The organic layer was dried over anhydrous $Na_2SO_4$, filtered, and concentrated to get a semi solid. This semi solid was washed with 2×50 mL of n-pentane to yield as a yellow solid. (9 g, 68% yield), $^1H$ NMR (DMSO-$d_6$, 400 MHz): δ (ppm): 8.15 (s, 1H), 7.49-7.53 (d, J=16 Hz, 1H), 6.89 (s, 1H), 6.68-6.72 (d, J=16 Hz, 1H), 3.41 (s, 3H), 4.18-4.23 (q, J=7.2 Hz, 2H), 1.23-1.26 (t, J=6.8 Hz, 3H). MS (ESI): mass calcd. for $C_{11}H_{12}BrNO_3$, 286.12; m/z found, 288[M+2H]$^+$.

Synthesis of Intermediate VII

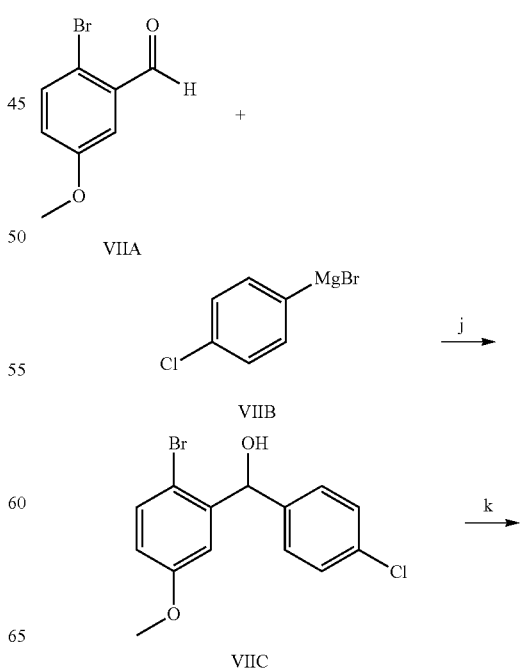

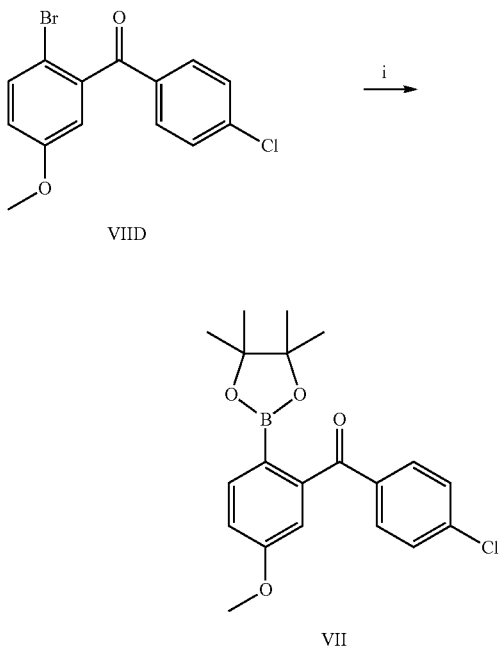

VIID

VII

Step J: 2-bromo-α-(4-chlorophenyl)-5-methoxy-benzenemethanol-VIIC

To a stirred solution of 2-bromo-5-methoxybenzaldehyde (VIIA, 25 g, 116 mmol) in dry tetrahydrofuran (350 mL) under $N_2$ atmosphere at 0° C., 4-chlorophenylmagnesium bromide 1.0 M solution in diethyl ether (140 mL, 140 mmol) was added drop wise. Then reaction mixture was left for stirring over 2 h. After the completion of reaction, reaction mixture was quenched by saturated ammonium chloride solution and diluted with ethyl acetate. Reaction mixture was filtered through celite bed. Organic layer was separated and washed with brine, dried over sodium sulphate, concentrated under reduced pressure. The Crude was washed with n-pentane to yield as a off white solid (38 g, 95% yield). MS (ESI): mass calcd for $C_{14}H_{12}BrClO_2$, 327.60; m/z found, 326[M−H]−.

Step I: (2-bromo-5-methoxyphenyl)(4-chlorophenyl)-Methanone-VIID

To a stirred solution of 2-bromo-α-(4-chlorophenyl)-5-methoxy-Benzenemethanol (VIIC, 20 g, 0.06 mol) in dry dichloromethane (350 mL), pyridinium chlorochromate (17 g, 0.078 mol) was added under $N_2$ atmosphere. The reaction mixture was stirred for 1.5 h. After the completion of reaction, mixture was filtered through silica gel (100-200 mesh) bed. Then dichloromethane layer was washed by saturated sodium bicarbonate solution, followed by brine, dried over sodium sulphate. Organic layer was concentrated and purified using silica gel column chromatography using 2-5% EtOAc/hexane as the eluent to yield as a white solid (13 g, 65% yield). MS (ESI): mass calcd for $C_{14}H_{10}BrClO_2$, 325.59; m/z found, 326[M+H]+.

Step K: (4-chlorophenyl)[5-methoxy-2-(4,4,5,5-tetramethyl-1,3,2-dioxaborolan-2-yl)phenyl]Methanone-VII To a stirred solution of (2-bromo-5-methoxyphenyl)(4-chlorophenyl)-Methanone (VIID, 14.8 g, 0.045 mol) in dioxane (350 mL), potassium acetate (26.7 g, 0.27 mol) and Bis(pinacolato)diborane (18 g, 0.0726 mol) were added. The mixture was purged with nitrogen gas for 30 min. Then Pd(dppf)Cl$_2$ (2.2 g, 0.0027 mol) was added. The reaction mixture was refluxed at 95° C. for 2.5 h. After the completion of reaction, reaction mixture was filtered through celite bed. Then dioxane was completely evaporated. Crude was dissolved in ethyl acetate, washed with brine, dried over sodium sulphate, concentrated. The crude was purified by Biotage purifier, eluted in 1%-3% EA/Hexane to yield as a white solid (10 g, 59% yield). MS (ESI): mass calcd for $C_{20}H_{22}BClO_4$, 372.65; m/z found, 373[M+H]+.

Step F: (E)-ethyl 3-(5-(2-(4-chlorobenzoyl)-4-methoxyphenyl)-1-methyl-2-oxo-1,2-dihydropyridin-4-yl)acrylate-VIII To a stirred solution of (E)-ethyl 3-(5-bromo-1-methyl-2-oxo-1,2-dihydropyridin-4-yl)acrylate (VI, 2.0 g, 6.99 mmol) in dimethoxy ethane/water (60:15 mL), (4-chlorophenyl)(5-methoxy-2-(4,4,5,5-tetramethyl-1,3,2-dioxaborolan-2 yl)phenyl)methanone (VII, 3.38 g, 9.08 mmol), sodium carbonate (2.2 mL, 20.97 mmol) was added at room temperature and purged with nitrogen gas for 15 min, followed by Pd(PPh$_3$)$_4$ (0.8 g, 0.699 mmol) was added under nitrogen atmosphere. The mixture was stirred for 28 h at 90° C. The reaction mixture was cooled to room temperature and concentrated the mixture under reduced pressure. The crude product was dissolved in ethyl acetate. The organic layer was washed with brine, dried over Na$_2$SO$_4$, concentrated under reduced pressure. The crude was purified by combi-flash (Silica gel, 5-80% EtOAc/hexane) to give yellow solid (1.25 g, 40% yield). $^1$H NMR (DMSO-d$_6$, 400 MHz): δ (ppm): 9.13 (s, 1H), 8.07 (s, 1H), 7.63-7.61 (d, J=8.0 Hz, 2H), 7.52-7.50 (d, J=8.0 Hz, 2H), 4.47 (m, 1H), 4.31 (m, 1H), 4.05 (m, 3H), 3.78 (m, 1H), 3.02 (m, 1H), 2.74 (m, 1H), 2.31 (m, 1H), 1.77-1.68 (m, 1H), 1.35 (t, J=4 Hz, 2H), 1.13 (s, 2H), 0.99 (t, J=8 Hz, 2H). MS (ESI): mass calcd. for $C_{25}H_{22}ClNO_5$, 451.9: m/z found, 452.1[M+H]+.

Step G: (E)-ethyl 3-(5-(2-((4-chlorophenyl)(hydroxy)methyl)-4-methoxyphenyl)-1-methyl-2-oxo-1,2-dihydropyridin-4-yl)acrylate-IX To a stirred solution of (E)-ethyl 3-(5-(2-(4-chlorobenzoyl)-4-methoxyphenyl)-1-methyl-2-oxo-1,2-dihydropyridin-4-yl)acrylate (1.25 g, 2.76 mmol) in methanol (30 mL), sodium borohydride (0.153 g, 4.14 mmol) was added at room temperature under nitrogen atmosphere. The reaction mixture was stirred for 1 h at room temperature. The reaction was monitored by TLC, after completion of the reaction; mixture was quenched with saturated ammonium chloride and concentrated under reduced pressure. The residue was partitioned with ethyl acetate and water. The organic layer was washed with brine, dried over Na$_2$SO$_4$, concentrated under reduced pressure to yield a yellow solid (1.25 g crude). MS (ESI): mass calcd. for $C_{25}H_{24}ClNO_5$, 453.91; m/z found, 454.1[M+H]+.

Step H: ±ethyl 2-((7-(4-chlorophenyl)-9-methoxy-2-methyl-3-oxo-2,3,5,7-tetrahydrobenzo[5,6]oxepino[4,3-c]pyridin-5-yl)acetate—Example 1

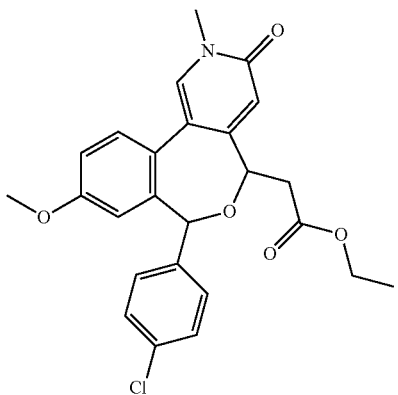 [SMILES: CCOC(=O)CC1OC(c2ccc(Cl)cc2)c2cc(OC)ccc2-c2cn(C)c(=O)cc21]

To a stirred solution of (E)-ethyl 3-(5-(2-((4-chlorophenyl)(hydroxy)methyl)-4-methoxyphenyl)-1-methyl-2-oxo-1,2-dihydropyridin-4-yl)acrylate (0.15 g, 0.33 mmol) in ethanol (10 mL), potassium carbonate (0.068 g, 0.495 mmol) was added at room temperature under nitrogen atmosphere. The mixture was stirred for 24 h at room temperature. After completion of the reaction, the mixture was quenched with water and concentrated under reduced pressure. The residue was partitioned with ethyl acetate and water. The organic layer was washed with brine, dried over $Na_2SO_4$, concentrated under reduced pressure. The crude was purified by HPLC using Inertsil ODS (250 mm×4.6 mm×5μ) column with 0.01% ammonia/water and acetonitrile as mobile phase to yield two diastereomers as white solid (0.05 g, 33.3% yield). MS (ESI): mass calcd. for $C_{25}H_{24}ClNO_5$, 453.91; m/z found, 454.2[M+H]$^+$.

Preparative Chiral HPLC Method for the Separation of Diastereomers 1
Column: CHIRALPAK IA (250 mm×4.6 mm×5 μm)
Wavelength: 254 nm UV
Injection Volume: 25.0 μl/min. 20 deg. C.
Eluent: 80:20:0.1 MTBE:MeOH:DEA Example 1A Ethyl-2-((5S,7R)-(4-chlorophenyl)-9-methoxy-2-methyl-3-oxo-2,3,5,7-tetrahydrobenzo[5,6]oxepino[4,3-c]pyridin-5-yl)acetate

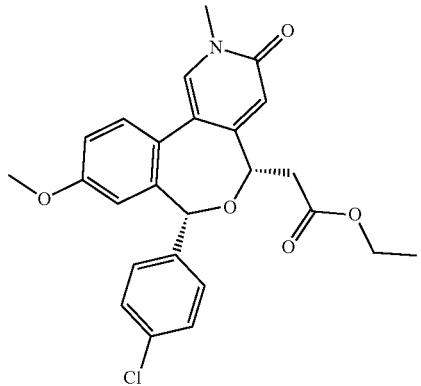 [SMILES: CCOC(=O)C[C@@H]1O[C@H](c2ccc(Cl)cc2)c2cc(OC)ccc2-c2cn(C)c(=O)cc21]

$^1$H NMR (DMSO-$d_6$, 400 MHz): δ (ppm) 7.8 (s, 1H), 7.38 (d, J=8.4 Hz, 1H), 7.25 (d, J=8.4 Hz, 2H), 7.08 (d, J=8.4 Hz, 2H), 7.03-7.00 (dd, J=14.0 Hz, J=2.0 Hz, 1H), 6.81 (bs, 1H), 6.35 (s, 1H), 5.95 (s, 1H), 4.88 (t, J=8.4 Hz, 1H), 4.09-4.04 (m, 2H), 3.75 (s, 3H), 3.4 (s, 3H), 2.80-2.78 (m, 2H), 1.16 (t, J=7.2 Hz, 3H). MS (ESI): mass calcd. for $C_{25}H_{24}ClNO_5$, 453.13; m/z found, 454.2[M+H]$^+$.

Example 1B

Ethyl-2-((5S,7S)-(4-chlorophenyl)-9-methoxy-2-methyl-3-oxo-2,3,5,7-tetrahydrobenzo[5,6]oxepino[4,3-c]pyridin-5-yl)acetate

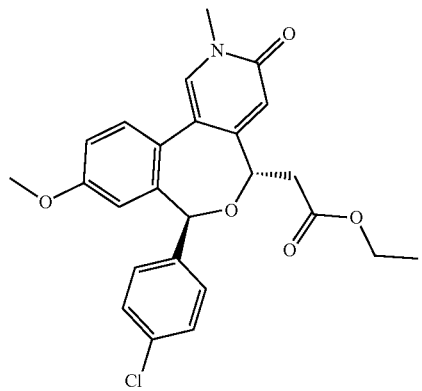 [SMILES: CCOC(=O)C[C@@H]1O[C@@H](c2ccc(Cl)cc2)c2cc(OC)ccc2-c2cn(C)c(=O)cc21]

$^1$H NMR (DMSO-$d_6$, 400 MHz): δ (ppm) 7.98 (s, 1H), 7.45 (d, J=8.4 Hz, 3H), 7.31 (d, J=8.0 Hz, 2H), 7.07-7.04 (dd, J=2.4 Hz, J=2.4 Hz, 1H), 6.43 (s, 1H), 5.96-5.96 (d, J=1.6 Hz, 1H), 5.48 (s, 1H), 4.51 (m, 1H), 4.09-4.07 (m, 2H), 3.63 (s, 3H), 3.53 (s, 3H), 2.95 (d, J=7.2 Hz, 2H), 1.16 (t, J=7.2 Hz, 3H). MS (ESI): mass calcd. for $C_{25}H_{24}ClNO_5$, 453.13; m/z found, 454.2[M+H]$^+$.

Example 1C

Ethyl-2-((5R,7S)-(4-chlorophenyl)-9-methoxy-2-methyl-3-oxo-2,3,5,7-tetrahydrobenzo[5,6]oxepino[4,3-c]pyridin-5-yl)acetate

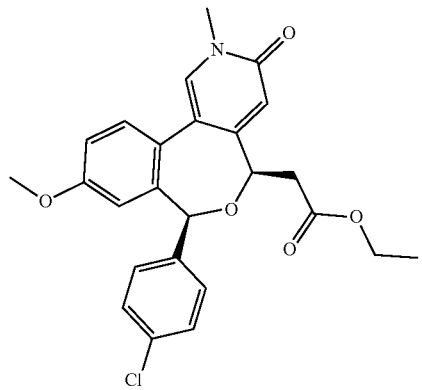 [SMILES: CCOC(=O)C[C@H]1O[C@@H](c2ccc(Cl)cc2)c2cc(OC)ccc2-c2cn(C)c(=O)cc21]

$^1$H NMR (DMSO-$d_6$, 400 MHz): δ (ppm) 7.8 (s, 1H), 7.38 (d, J=8.4 Hz, 1H), 7.25 (d, J=8.4 Hz, 2H), 7.08 (d, J=8.4 Hz, 2H), 7.03-7.00 (dd, J=14.0 Hz, J=2.0 Hz, 1H), 6.81 (bs, 1H), 6.35 (s, 1H), 5.95 (s, 1H), 4.88 (t, J=8.4 Hz, 1H), 4.09-4.04 (m, 2H), 3.75 (s, 3H), 3.4 (s, 3H), 2.80-2.78 (m, 2H), 1.16 (t, J=7.2 Hz, 3H). MS (ESI): mass calcd. for $C_{25}H_{24}ClNO_5$, 453.13; m/z found, 454.2[M+H]$^+$.

Example 1D

Ethyl-2-((5R,7R)-(4-chlorophenyl)-9-methoxy-2-methyl-3-oxo-2,3,5,7-tetrahydrobenzo[5,6]oxepino[4,3-c]pyridin-5-yl)acetate

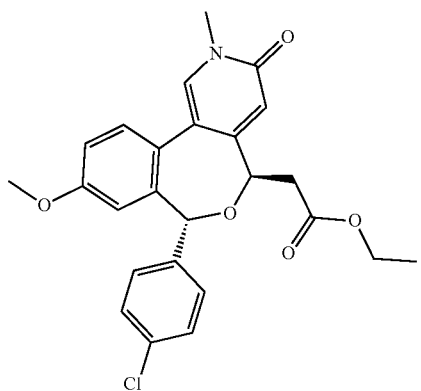 [SMILES: CCOC(=O)C[C@H]1O[C@H](c2ccc(Cl)cc2)c2cc(OC)ccc2-c2cn(C)c(=O)cc21]

$^1$H NMR (DMSO-d$_6$, 400 MHz): δ (ppm) 7.98 (s, 1H), 7.45 (d, J=8.4 Hz, 3H), 7.31 (d, J=8.0 Hz, 2H), 7.07-7.04 (dd. J=2.4 Hz, J=2.4 Hz, 1H), 6.43 (s, 1H), 5.96-5.96 (d, J=1.6 Hz, 1H), 5.48 (s, 1H), 4.51 (m, 1H), 4.09-4.07 (m, 2H), 3.63 (s, 3H), 3.53 (s, 3H), 2.95 (d, J=7.2 Hz, 2H), 1.16 (t, J=7.2 Hz, 3H). MS (ESI): mass calcd. for $C_{25}H_{24}ClNO_5$, 453.13; m/z found, 454.2[M+H]$^+$.

Following compounds were synthesized using the above procedure as exemplified in example 1

Example 2

±Ethyl-2-(7-cyclohexyl-9-methoxy-2-methyl-3-oxo-2,3,5,7-tetrahydrobenzo[5,6]oxepino[4,3-c]pyridin-5-yl)acetate

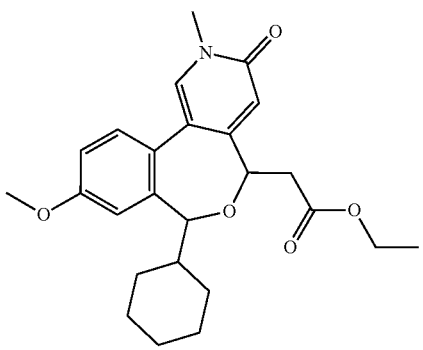 [SMILES: CCOC(=O)CC1OC(C2CCCCC2)c2cc(OC)ccc2-c2cn(C)c(=O)cc21]

MS (ESI): mass calcd. for $C_{25}H_{31}NO_5$, 425.1; m/z found, 426.2[M+H]$^+$.

Example 3

±Ethyl-2-(7-(cyclopropylmethyl)-9-methoxy-2-methyl-3-oxo-2,3,5,7-tetrahydrobenzo[5,6]oxepino[4,3-c]pyridin-5-yl)acetate

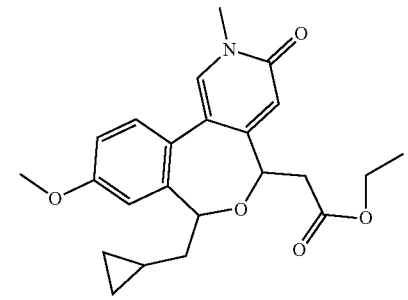 [SMILES: CCOC(=O)CC1OC(CC2CC2)c2cc(OC)ccc2-c2cn(C)c(=O)cc21]

MS (ESI): mass calcd. for $C_{23}H_{27}NO_5$, 397.2; m/z found, 398.2 [M+H]$^+$.

Example 4

±Ethyl-2-(9-methoxy-2-methyl-7-(5-methylpyridin-2-yl)-3-oxo-2,3,5,7-tetrahydrobenzo[5,6]oxepino[4,3-c]pyridin-5-yl)acetate

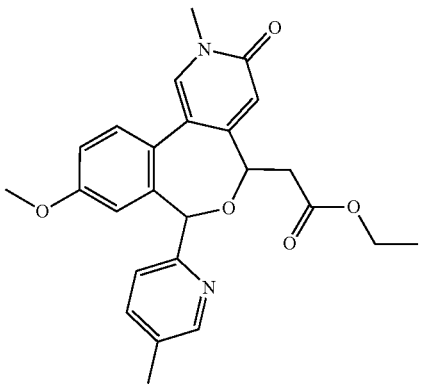 [SMILES: CCOC(=O)CC1OC(c2ccc(C)cn2)c2cc(OC)ccc2-c2cn(C)c(=O)cc21]

MS (ESI): mass calcd. for $C_{25}H_{26}N_2O_5$, 434.2: m/z found, 435.2[M+H]$^+$.

Example 5

±Ethyl-2-(7-(4-chlorophenyl)-9-fluoro-2-methyl-3-oxo-2,3,5,7-tetrahydrobenzo[5,6]oxepino[4,3-c]pyridin-5-yl)acetate

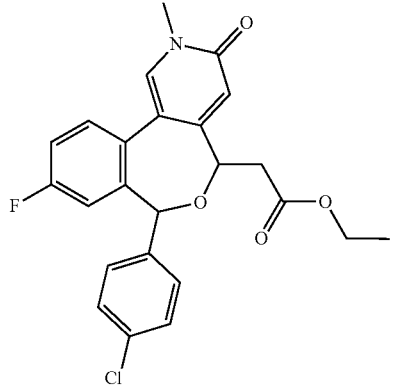 [SMILES: CCOC(=O)CC1OC(c2ccc(Cl)cc2)c2cc(F)ccc2-c2cn(C)c(=O)cc21]

(ESI): mass calcd for $C_{24}H_{21}ClFNO_4$, 441.2; m/z found, 442.2 [M+H]$^+$.

Example 6

±Ethyl-2-(7-(4-chlorophenyl)-2-methyl-3-oxo-9-(trifluoromethyl)-2,3,5,7-tetrahydrobenzo[5,6]oxepino[4,3-c]pyridin-5-yl)acetate

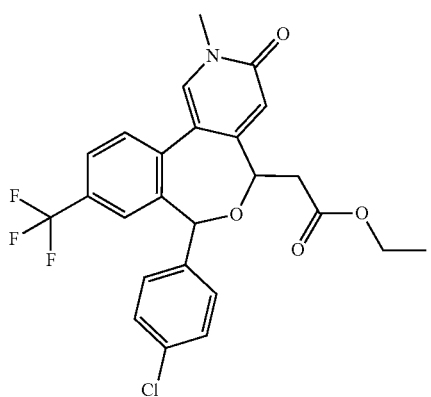 [SMILES: CCOC(=O)CC1OC(c2ccc(Cl)cc2)c2cc(C(F)(F)F)ccc2-c2cn(C)c(=O)cc21]

(ESI): mass calcd for $C_{25}H_{21}ClF_3NO_4$, 491.3; m/z found, 492.3 [M+H]$^+$.

Example 7

±7(4-chlorophenyl)-5-(2-hydroxyethyl) 9-methoxy, 2-methyl, 5,7dihydrobenzo[5,6]oxepino[4,3-c]pyridin-3(2H)-one

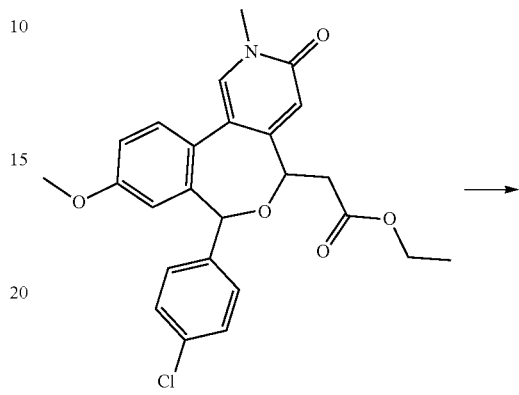

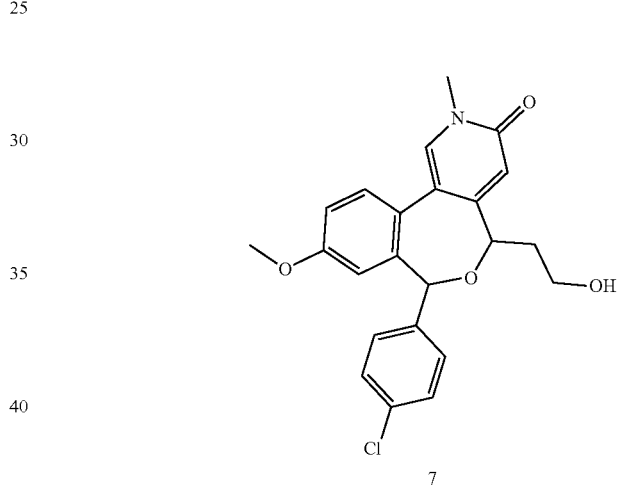

To a stirred solution of ethyl 2-(7-(4-chlorophenyl)-9-methoxy-2-methyl-3-oxo-2,3,5,7-tetrahydrobenzo[5,6]oxepino[4,3-c]pyridin-5-yl)acetate (example 1) (0.025 g, 0.055 mmol) in dry THF (1 mL), at 0° C. Lithium Aluminium Hydride (0.0023, 0.06 mmol, 2M in THF) was added dropwise and stirred at same temperature for 1 h. After the completion of reaction, reaction mixture was quenched with saturated ammonium chloride solution. Reaction mixture was extracted with DCM dried over sodium sulphate and concentrated. The crude product was purified by Biotage purifier, eluted in 1%-5% DCM/Methanol to yield 7-(4-chlorophenyl)-5-(2-hydroxyethyl)-9-methoxy-2-methyl-5,7-dihydrobenzo[5,6]oxepino[4,3-c]pyridin-3(2H)-one as a off-white solid (8 mg, 35% yield). $^1$H NMR (DMSO-d$_6$, 400 MHz): δ (ppm) 7.78 (s, 1H), 7.37 (d, J=8.4 Hz, 1H), 7.27 (d, J=7.6 Hz, 2H), 7.12 (d, J=7.6 Hz, 2H), 7.00 (d, J=8.4 Hz, 1H), 6.68 (s, 1H), 6.34 (s, 1H), 5.92 (s, 1H), 4.70-4.60 (m, 1H), 4.50-4.45 (m, 1H), 3.72 (s, 3H), 3.60-3.48 (m, 2H), 3.43 (s, 3H), 1.82-1.70 (m, 2H). MS (ESI): mass calcd. for $C_{23}H_{22}ClNO_4$, 411.1; m/z found, 412.1 [M+H]$^+$.

Example 8

±2-(7-(4-chlorophenyl)9methoxy2methyl3oxo2,3,5,7tetrahydrobenzo[5,6]oxepino[4,3-c]pyridin-5-yl)-N-ethylacetamide

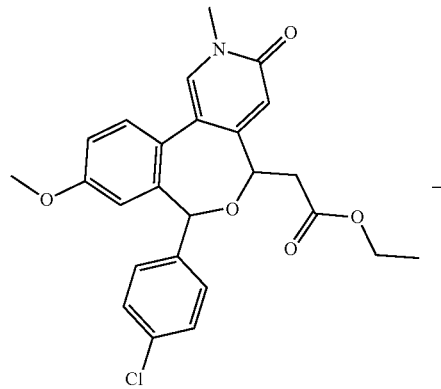

1

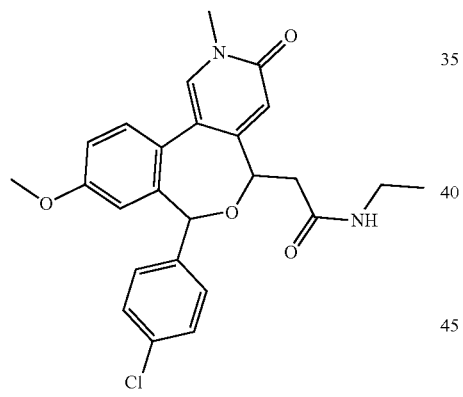

8

To a stirred solution of ethyl 2-(7-(4-chlorophenyl)-9-methoxy-2-methyl-3-oxo-2,3,5,7-tetrahydrobenzo[5,6]oxepino[4,3-c]pyridin-5-yl)acetate (example 1) (0.5 g, 1.1 mmol) in THF (2 mL), trimethyl aluminium (4.4 mL, 8.8 mmol) and 2 M ethyl amine solution (4.4 mL, 8.8 mmol) was added at 0° C. under nitrogen atmosphere. The mixture was stirred for 1 h at 90° C. The mixture was quenched with saturated ammonium chloride. The residue was partitioned with ethyl acetate and water. The organic layer was washed with cold water, dried over Na$_2$SO$_4$, concentrated under reduced pressure. The crude was purified by HPLC using InertsilODS (250 mm×4.6 mm×5µ) column with 0.01% ammonia/water and ACN as mobile phase with UV detection 254 nm was utilized. 160 mg of a mixture of diastereomer 8A and 140 mg of a mixture of diastereomer 8B obtained.

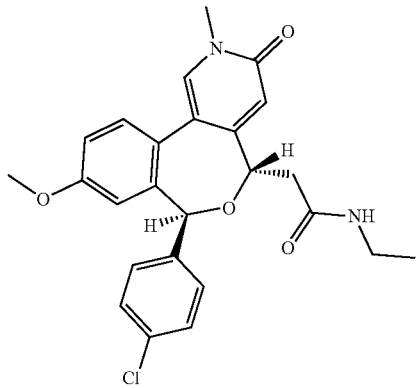

±8A

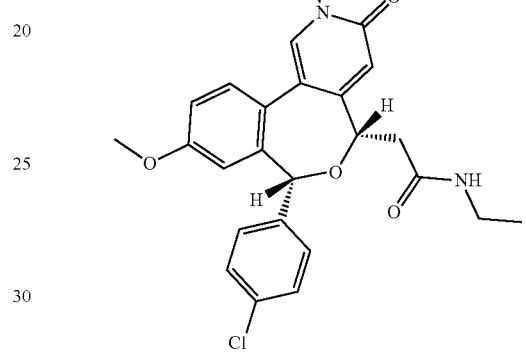

±8B

Preparative Chiral HPLC Method for the Separation of Diastereomers 8A and 8B:
Column: CHIRALPAK IA (250 mm×4.6 mm×5 µm)
Wavelength: 254 nm UV
Injection Volume: 25.0 µl/min. 20 deg C.
Eluent: 80:20:0.1 MTBE:MeOH:DEA

Example 5C 2-((5S,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide

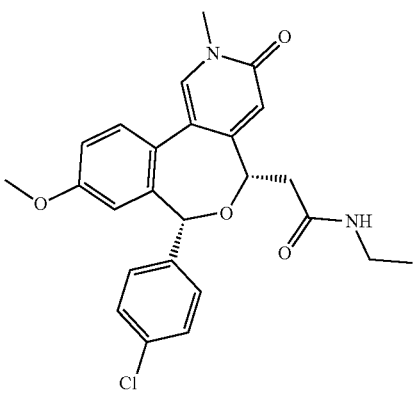 [SMILES: CCNC(=O)C[C@@H]1O[C@H](c2ccc(Cl)cc2)c2cc(OC)ccc2-c2cn(C)c(=O)cc21]

$^1$H-NMR (DMSO-d$_6$, 400 MHz) δ (ppm): 7.95 (br. s., 1H), 7.75 (s, 1H), 7.37 (d, J=8.8 Hz, 1H), 7.22 (d, J=8.4 Hz, 2H), 7.04-6.99 (m, 3H), 6.92 (s, 1H), 6.30 (s, 1H), 5.97 (s, 1H), 4.86 (t, J=7.2 Hz, 1H), 3.76 (s, 3H), 3.41 (s, 3H), 3.06-3.03 (m, 2H), 2.64-2.62 (m, 2H), 0.98 (t, J=7.2 Hz, 3H). MS (ESI): mass calcd. for $C_{25}H_{25}ClN_2O_4$, 452.2; m/z found, 453.2[M+H]$^+$.

Example 8D 2-((5S,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide

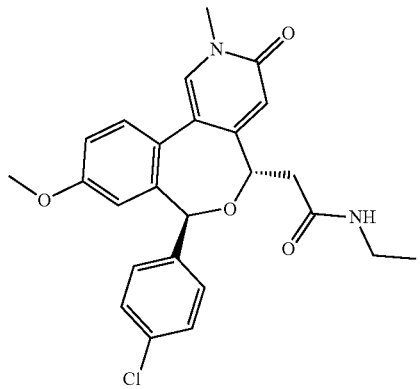 [SMILES: CCNC(=O)C[C@@H]1O[C@@H](c2ccc(Cl)cc2)c2cc(OC)ccc2-c2cn(C)c(=O)cc21]

$^1$H-NMR (DMSO-d$_6$, 400 MHz) δ (ppm): 8.02 (br. s., 1H), 7.96 (s, 1H), 7.45-7.41 (m, 3H), 7.34 (d, J=8.4 Hz, 2H), 7.07-7.04 (m, 1H), 6.44 (s, 1H), 5.94 (s, 1H), 5.46 (s, 1H), 4.52 (t, J=6.8 Hz, 1H), 3.62 (s, 3H), 3.53 (s, 3H), 3.10-3.00 (m, 2H), 2.70-2.68-2.66 (m, 2H), 1.00 (t, J=7.2 Hz, 3H). MS (ESI): mass calcd. for $C_{25}H_{25}ClN_2O_4$, 452.2; m/z found, 453.2[M+H]$^+$.

Example 8E 2-((5R,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide

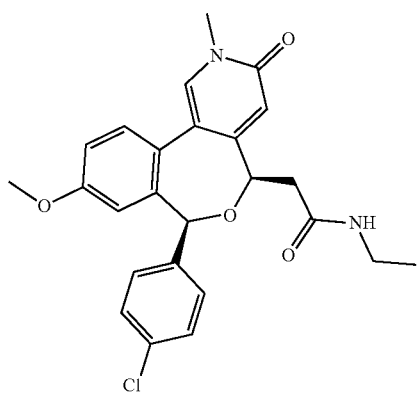 [SMILES: CCNC(=O)C[C@H]1O[C@@H](c2ccc(Cl)cc2)c2cc(OC)ccc2-c2cn(C)c(=O)cc21]

$^1$H-NMR (DMSO-d$_6$, 400 MHz) δ (ppm): 7.95 (br. s., 1H), 7.75 (s, 1H), 7.37 (d, J=8.8 Hz, 1H), 7.22 (d, J=8.4 Hz, 2H), 7.04-6.99 (m, 3H), 6.92 (s, 1H), 6.30 (s, 1H), 5.97 (s, 1H), 4.86 (t, J=7.2 Hz, 1H), 3.76 (s, 3H), 3.41 (s, 3H), 3.06-3.03 (m, 2H), 2.64-2.62 (m, 2H), 0.98 (t, J=7.2 Hz, 3H). MS (ESI): mass calcd. for $C_{25}H_{25}ClN_2O_4$, 452.2; m/z found, 453.2[M+H]$^+$.

Example 8F 2-((5R,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide

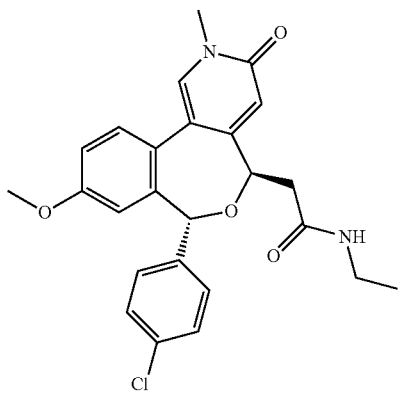 [SMILES: CCNC(=O)C[C@H]1O[C@H](c2ccc(Cl)cc2)c2cc(OC)ccc2-c2cn(C)c(=O)cc21]

$^1$H-NMR (DMSO-d$_6$, 400 MHz) δ (ppm): 8.02 (br. s., 1H), 7.96 (s, 1H), 7.45-7.41 (m, 3H), 7.34 (d, J=8.4 Hz, 2H), 7.07-7.04 (m, 1H), 6.44 (s, 1H), 5.94 (s, 1H), 5.46 (s, 1H), 4.52 (t, J=6.8 Hz, 1H), 3.62 (s, 3H), 3.53 (s, 3H), 3.10-3.00 (m, 2H), 2.70-2.68-2.66 (m, 2H), 1.00 (t, J=7.2 Hz, 3H). MS (ESI): mass calcd. for $C_{25}H_{25}ClN_2O_4$, 452.2: m/z found, 453.2[M+H]$^+$.

Following compounds were synthesized using the above procedure as exemplified in example 8

Example 9

±2-(7-cyclohexyl-9-methoxy-2-methyl-3-oxo-2,3,5,7-tetrahydrobenzo[5,6]oxepino[4,3-c]pyridin-5-yl)-N-ethylacetamide

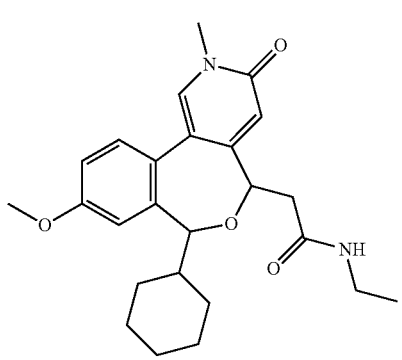 [SMILES: CCNC(=O)CC1OC(C2CCCCC2)c2cc(OC)ccc2-c2cn(C)c(=O)cc21]

This compound was synthesized and purified as described for synthesizing compound 8 and the diastereoisomers were separated by HPLC to give 9A and 9B using similar conditions for separating 8A and 8B

Example 9A

±2-((5S,7R)-7-cyclohexyl-9-methoxy-2-methyl-3-oxo-2,3,5,7-tetrahydrobenzo[5,6]oxepino[4,3-c]pyridin-5-yl)-N-ethylacetamide

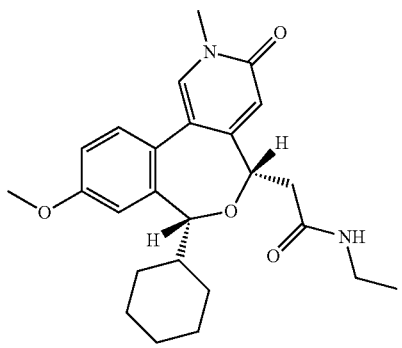 [SMILES: CCNC(=O)C[C@@H]1O[C@H](C2CCCCC2)c2cc(OC)ccc2-c2cn(C)c(=O)cc21]

¹H NMR: (400 MHz, DMSO-d) 7.91 (br.s, 1H) 7.83 (s, 1H) 7.36 (d, J=8.4 Hz, 1H) 7.02-7.01 (m, 1H) 6.94-6.92 (m, 1H), 6.23 (s, 1H), 4.66-4.63 (m, 1H), 4.60-4.58 (m, 1H), 3.78 (m, 3H), 3.48 (s, 3H), 3.07-3.00 (m, 2H), 2.66-2.53 (m, 2H), 1.56-1.47 (m, 4H), 1.37 (m, 1H), 1.22 (m, 1H), 1.33-0.98 (m, 6H), 0.89-0.85 (m, 2H). (ESI): mass calcd for $C_{25}H_{32}N_2O_4$, 424.3; m/z found, 425.0 [M+H]⁺.

Example 9B

±2-((5S,7S)-7-cyclohexyl-9-methoxy-2-methyl-3-oxo-2,3,5,7-tetrahydrobenzo[5,6]oxepino[4,3-c]pyridin-5-yl)-N-ethylacetamide

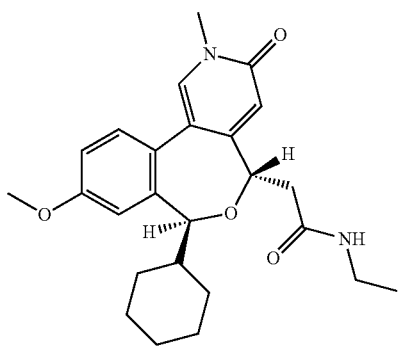 [SMILES: CCNC(=O)C[C@@H]1O[C@@H](C2CCCCC2)c2cc(OC)ccc2-c2cn(C)c(=O)cc21]

(ESI): mass calcd for $C_{25}H_2N_2O_4$, 424.3; m/z found, 425.0 [M+H]⁺.

Example 10

±2-(7-(cyclopropylmethyl)-9-methoxy-2-methyl-3-oxo-2,3,5,7-tetrahydrobenzo[5,6]oxepino[4,3-c]pyridin-5-yl)-N-ethylacetamide

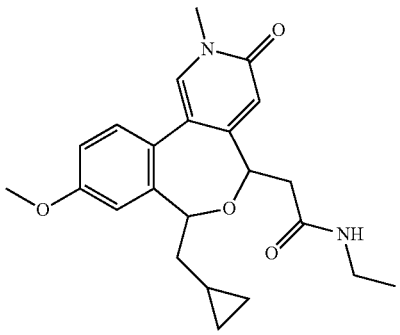 [SMILES: CCNC(=O)CC1OC(CC2CC2)c2cc(OC)ccc2-c2cn(C)c(=O)cc21]

Compound 10 was synthesized and purified as described for synthesizing compound 8 and the diastereoisomers were separated by HPLC to give 10A and 10B using similar conditions for separating 8A and 8B

Example 10A 2-((5S,7R)-7-(cyclopropylmethyl)-9-methoxy-2-methyl-3-oxo-2,3,5,7-tetrahydrobenzo[5,6]oxepino[4,3-c]pyridin-5-yl)-N-ethylacetamide

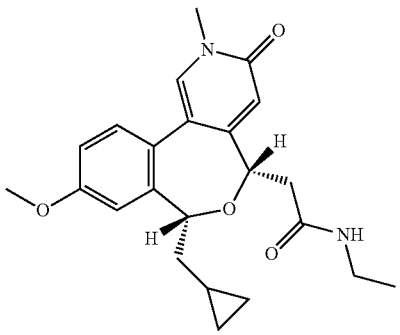 [SMILES: CCNC(=O)C[C@@H]1O[C@H](CC2CC2)c2cc(OC)ccc2-c2cn(C)c(=O)cc21]

¹H-NMR (DMSO-d₆, 400 MHz): δ (ppm) 7.90-7.85 (m, 2H), 7.34 (d, J=8.4 Hz, 1H), 6.95 (d, J=8.4 Hz, 1H), 6.85 (s, 1H), 6.26 (s, 1H), 4.81 (t, J=6.0 Hz, 1H), 4.71 (t, J=6.8 Hz, 1H), 3.77 (s, 3H), 3.47 (s, 3H), 3.10-2.95 (m, 2H), 1.56-1.45 (m, 1H), 1.30-1.20 (m, 2H), 0.95 (t, J=6.8 Hz, 3H), 0.55-0.45 (m, 1H), 0.3-0.15 (m, 2H), (−)0.12-(−)0.13 (m, 2H). MS (ESI): mass calculated for $C_{23}H_{28}N_2O_4$, 396.2 m/z found, 397.2[M+H]⁺.

Example 10B

±2-((5S,7S)-7-(cyclopropylmethyl)-9-methoxy-2-methyl-3-oxo-2,3,5,7-tetrahydrobenzo[5,6]oxepino[4,3-c]pyridin-5-yl)-N-ethylacetamide

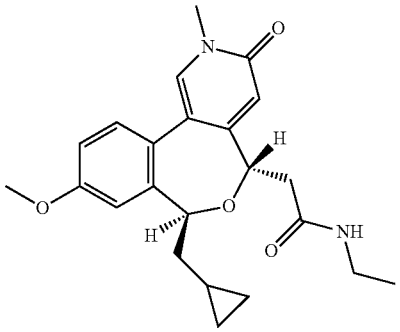 [SMILES: CCNC(=O)C[C@@H]1O[C@@H](CC2CC2)c2cc(OC)ccc2-c2cn(C)c(=O)cc21]

$^1$H-NMR (DMSO-d$_6$, 400 MHz): δ (ppm) 7.93 (br. s., 1H), 7.84 (s, 1H), 7.36 (d, J=8.4 Hz, 1H), 7.02 (d, J=8.4 Hz, 1H), 6.95 (s, 1H), 6.42 (s, 1H), 4.26 (t, J=Hz, 1H), 4.20 (t, J=Hz, 1H), 3.80 (s, 3H), 3.48 (s, 3H), 3.01-2.95 (m, 2H), 2.70-2.60 (m, 2H), 1.82-1.70 (m, 2H), 0.95 (t, J=7.2 Hz, 3H), 0.75-0.60 (m, 1H), 0.33-0.31 (m, 2H), 0.05-0.015 (m, 2H). MS (ESI): mass calculated for C$_{23}$H$_{28}$N$_2$O$_4$, 396.2; m/z found, 397.2[M+H]$^+$.

Example 11

±2-(9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide

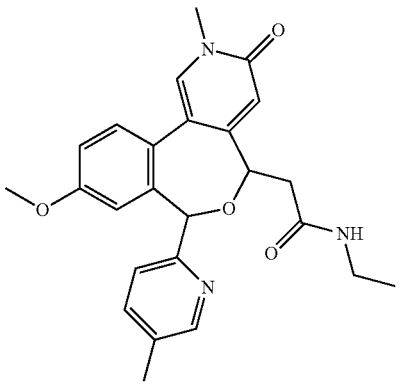 [SMILES: CCNC(=O)CC1OC(c2ccc(C)cn2)c2cc(OC)ccc2-c2cn(C)c(=O)cc21]

Compound 11 was synthesized and purified as described for synthesizing compound 8 and the diastereoisomers were separated by HPLC to give 11A and 11B using similar conditions for separating 8A and 8B.

Example 11A

±2-((5S,7S)-9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide

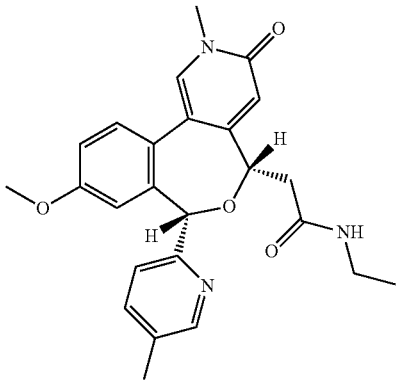 [SMILES: CCNC(=O)C[C@@H]1O[C@H](c2ccc(C)cn2)c2cc(OC)ccc2-c2cn(C)c(=O)cc21]

$^1$HNMR: (400 MHz, DMSO-d): δ (ppm) 8.36 (s, 1H), 8.04 (t, J=8 Hz, 1H), 7.96 (s, 1H), 7.79 (d, J=8 Hz, 1H), 7.53 (d, J=8 Hz, 1H), 7.43 (d, J=8 Hz, 1H), 7.05-7.03 (m, 1H), 6.45 (s, 1H), 5.83 (s, 1H), 5.40 (s, 1H), 4.54-4.51 (m, 1H), 3.61 (s, 3H), 3.52 (s, 3H), 3.09-3.00 (m, 2H), 2.70-2.69 (m, 2H), 2.30 (s, 3H), 0.99 (t, J=8 Hz, 3H). (ESI): mass calcd for C$_{25}$H$_{27}$N$_3$O$_4$, 433.1; m/z found, 434.2.0 [M+H]$^+$.

Example 11B

±2-((5S,7R)-9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide

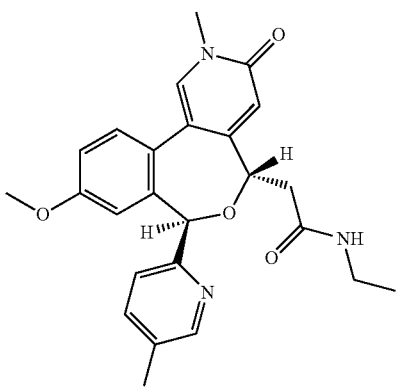 [SMILES: CCNC(=O)C[C@@H]1O[C@@H](c2ccc(C)cn2)c2cc(OC)ccc2-c2cn(C)c(=O)cc21]

(ESI): mass calcd for C$_{25}$H$_{27}$N$_3$O$_4$, 433.1; m/z found, 434.2.0 [M+H]$^+$.

Example 12

±2-(7-(4-chlorophenyl)-9-fluoro-2-methyl-3-oxo-2,3,5,7-tetrahydrobenzo[5,6]oxepino[4,3-c]pyridin-5-yl)-N-ethylacetamide Compound 12 was synthesized and purified as described for synthesizing compound 8 and the diastereoisomers were separated by HPLC to give 12A and 12B using similar conditions for separating 8A and 8B

Example 12A

±-2-((5S,7R)-7-(4-chlorophenyl)-9-fluoro-2-methyl-3-oxo-2,3,5,7-tetrahydrobenzo[5,6]oxepino[4,3-c]pyridin-5-yl)-N-ethylacetamide

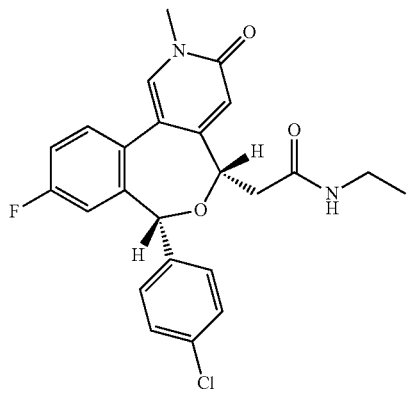 [SMILES: CCNC(=O)C[C@@H]1O[C@H](c2ccc(Cl)cc2)c2cc(F)ccc2-c2cn(C)c(=O)cc21]

$^1$H NMR (DMSO-d$_6$, 400 MHz): δ (ppm) 8.03 (br.s., 2H), 7.57-7.53 (m, 1H), 7.45 (d, J=8.0 Hz, 2H), 7.36-7.34 (m, 2H), 6.45 (s, 1H), 6.16 (d, J=8.0 Hz, 1H), 5.48 (s, 1H), 4.49-4.46 (m, 1H), 3.52 (s, 3H), 3.05-3.01 (m 3H), 2.69-2.64 (m, 2H), 0.98 (t, J=8.0 Hz, 3H); MS(ESI): mass calcd for C$_{24}$H$_{22}$ClFN$_2$O$_3$, 440.1; m/z found, 441.2 [M+H]$^+$.

Example 12B

±2-((5S,7S)-9-fluoro-2-methyl-3-oxo-7-phenyl-2,3,5,7-tetrahydrobenzo[5,6]oxepino[4,3-c]pyridin-5-yl)-N-ethylacetamide

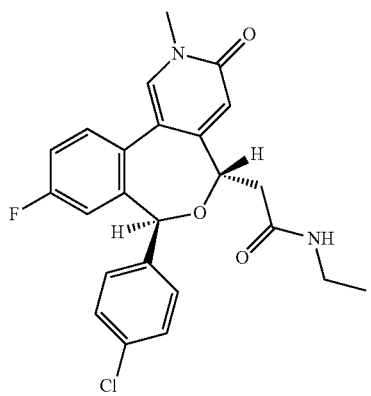 [SMILES: CCNC(=O)C[C@@H]1O[C@@H](c2ccc(Cl)cc2)c2cc(F)ccc2-c2cn(C)c(=O)cc21]

$^1$H NMR (DMSO-d$_6$, 400 MHz): δ (ppm) 7.93 (s, 1H), 7.83 (s, 1H), 7.50-7.47 (m, 1H), 7.22 (d, J=8.0 Hz, 2H), 7.16-7.14 (m, 1H), 7.05 (d, J=8.0 Hz, 2H), 6.31 (s, 1H), 5.99 (s, 1H), 4.87-4.85 (m, 1H), 3.41 (s, 3H), 3.05-3.02 (m, 2H), 2.64-2.58 (m, 3H), 0.90 (t, J=8.0 Hz, 3H); MS(ESI): mass calcd for C$_{24}$H$_{22}$ClFN$_2$O$_3$, 440.1; m/z found, 441.2 [M+H]$^+$.

Example 13

2-(7-(4-chlorophenyl)-2-methyl-3-oxo-9-(trifluoromethyl)-2,3,5,7-tetrahydrobenzo[5,6]oxepino[4,3-c]pyridin-5-yl)-N-ethylacetamide

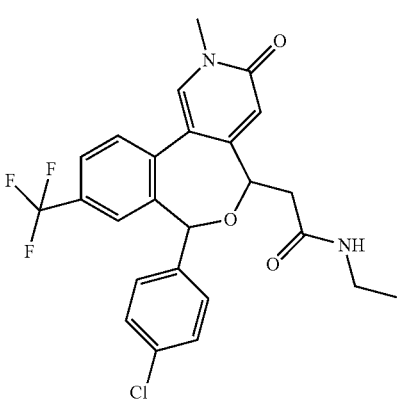 [SMILES: CCNC(=O)CC1OC(c2ccc(Cl)cc2)c2cc(C(F)(F)F)ccc2-c2cn(C)c(=O)cc21]

Compound 13 was synthesized and purified as described for synthesizing compound 8 and the diastereoisomers were separated by HPLC to give 13A and 13B using similar conditions for separating 8A and 8B

Example 13A

±2-((5S,7R)-7-(4-chlorophenyl)-2-methyl-3-oxo-9-(trifluoromethyl)-2,3,5,7-tetrahydrobenzo[5,6]oxepino[4,3-c]pyridin-5-yl)-N-ethylacetamide

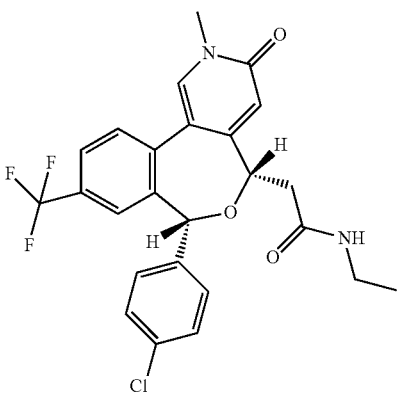 [SMILES: CCNC(=O)C[C@@H]1O[C@H](c2ccc(Cl)cc2)c2cc(C(F)(F)F)ccc2-c2cn(C)c(=O)cc21]

$^1$H NMR (DMSO-d$_6$, 400 MHz): δ (ppm) 8.15 (s, 1H), 8.01 (t, J=8 Hz, 1H), 7.85 (br.s., 1H), 7.75 (d, J=8.0 Hz, 1H), 7.47 (d, J=8.0 Hz, 2H), 7.37 (d, J=8.0 Hz, 2H), 6.67 (s, 1H), 6.48 (s, 1H), 5.57 (s, 1H), 4.49 (t, J=8.0 Hz, 1H), 3.54 (s, 3H), 3.07-3.03 (m, 2H), 2.69 (d, J=4.0 Hz, 2H), 0.98 (t, J=8.0 Hz, 3H). MS(ESI): mass calcd for C$_{25}$H$_{22}$ClF$_3$N$_2$O$_3$, 490.1; m/z found, 491.1 [M+H]$^+$.

Example 13B

±2-((5S,7S)-7-(4-chlorophenyl)-2-methyl-3-oxo-9-(trifluoromethyl)-2,3,5,7-tetrahydrobenzo[5,6]oxepino[4,3-c]pyridin-5-yl)-N-ethylacetamide

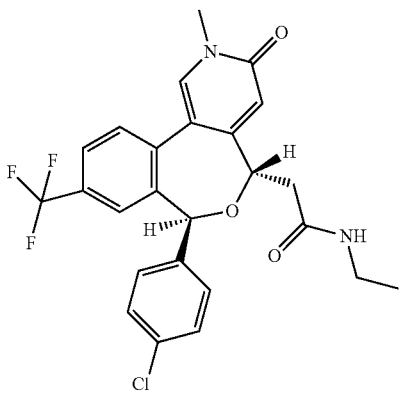 [SMILES: CCNC(=O)C[C@@H]1O[C@@H](c2ccc(Cl)cc2)c2cc(C(F)(F)F)ccc2-c2cn(C)c(=O)cc21]

¹H NMR (DMSO-d₆, 400 MHz): δ (ppm) 7.95 (br.s., 2H), 7.79 (d, J=8 Hz, 1H), 7.67 (d, J=8 Hz, 2H), 7.24 (d, J=8 Hz, 2H), 7.03 (d, J=8 Hz, 2H), 6.34 (s, 1H), 6.15 (s, 1H), 4.86 (t, J=7.8 Hz, 1H), 3.42 (s, 3H), 3.05-3.01 (m, 3H), 2.64-2.62 (m, 2H), 0.96 (t, J=8 Hz, 3H). MS(ESI): mass calcd for $C_{25}H_{22}ClF_3N_2O_3$, 490.1; m/z found, 491.1 $[M+H]^+$.

Example 14

±-Ethyl-2-(7-(4-chlorophenyl)-9-methoxy-2-methyl-3-oxo-3,5-dihydro-2H-benzo[c]pyrido[3,4-e]azepin-5-yl)acetate

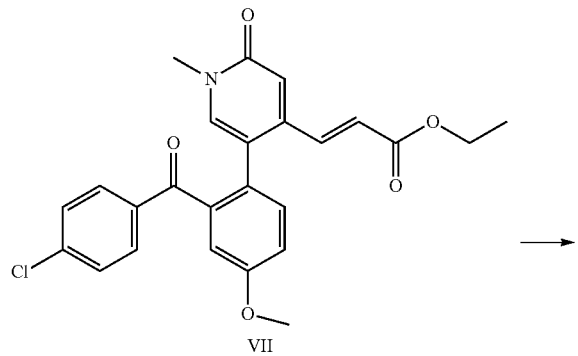

14

To a stirred solution of (E)-ethyl 3-(-(2-(4-chlorobenzoyl)-4-methoxyphenyl)-1-methyl-2-oxo-1,2-dihydropyridin-4-yl)acrylate (step F, example 1, compound VIII) (0.01 g, 0.22 mmol) in ethanol (2 mL), ammonium formate (0.280 mg, 4.4 mmol) was added at room temperature under nitrogen atmosphere. The reaction mixture was stirred at 95° C. for 4 h. After 4 h heating the reaction was monitored by LCMS. The reaction mixture was cooled to room temperature and concentrated under reduced pressure. The residue was partitioned with ethyl acetate and water. The organic layer was washed with brine, dried over $Na_2SO_4$ and concentrated under reduced pressure to get thick mass. The crude was purified by combi-flash eluting with (0-10%) MeOH:DCM. The pure fractions were concentrated to obtain white solid (15 mg, 15%). ¹HNMR (400 MHz, DMSO-d): δ (ppm) 8.02 (s, 1H), 7.65 (d, J=8, 1H), 7.46-7.40 (m, 4H), 7.28-7.25 (m, 1H), 6.75-6.73 (m, 1H), 6.34 (s, 1H), 4.22-4.06 (m 3H), 3.75 (s, 3H), 3.46 (s, 3H), 3.25-3.14 (m, 2H), 1.17 (t, J=7.2 Hz, 3H). MS(ESI): mass calcd for $C_{25}H_{23}ClN_2O_4$, 450.2; m/z found, 451.2 $[M+H]^+$.

Following compounds were synthesized using the above procedure as exemplified in example 14

Example 15

±Ethyl-2-(7-cyclohexyl-9-methoxy-2-methyl-3-oxo-3,5-dihydro-2H-benzo[c]pyrido[3,4-e]azepin-5-yl)acetate

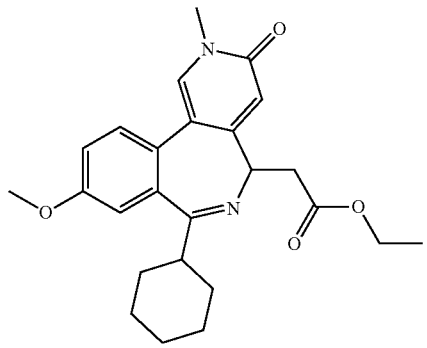 [SMILES: CCOC(=O)CC1N=C(C2CCCCC2)c2cc(OC)ccc2-c2cn(C)c(=O)cc21]

MS(ESI): mass calcd for $C_{25}H_{30}N_2O_4$, 422.0; m/z found, 423.2 $[M+H]^+$.

Example 16

±Ethyl-2-(9-methoxy-2-methyl-3-oxo-7-(pyridin-2-yl)-3,5-dihydro-2H-benzo[c]pyrido[3,4-e]azepin-5-yl)acetate

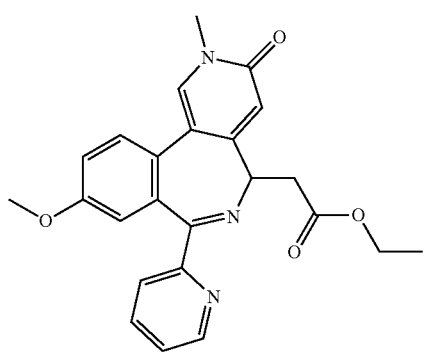 [SMILES: CCOC(=O)CC1N=C(c2ccccn2)c2cc(OC)ccc2-c2cn(C)c(=O)cc21]

MS (ESI): mass calculated for $C_{24}H_{23}N_3O_4$, 417.2; m/z found, 418.2.1 $[M+H]^+$.

Example 17

±Ethyl-2-(7-(cyclopropylmethyl)-9-methoxy-2-methyl-3-oxo-3,5-dihydro-2H-benzo[c]pyrido[3,4-e]azepin-5-yl)acetate

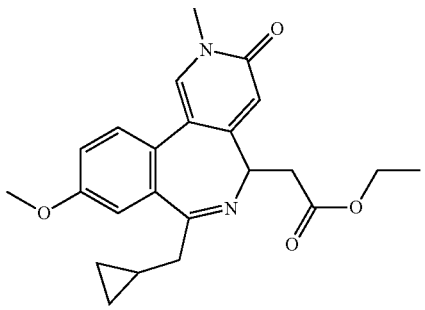 [SMILES: CCOC(=O)CC1N=C(CC2CC2)c2cc(OC)ccc2-c2cn(C)c(=O)cc21]

MS (ESI): mass calculated for $C_{20}H_{19}F_3N_2O_4$, 394.1; m/z found, 395.1[M+H]$^+$.

Example 18

±Ethyl-2-(9-methoxy-2-methyl-3-oxo-7-(trifluoromethyl)-3,5-dihydro-2H-benzo[c]pyrido[3,4-e]azepin-5-yl)acetate

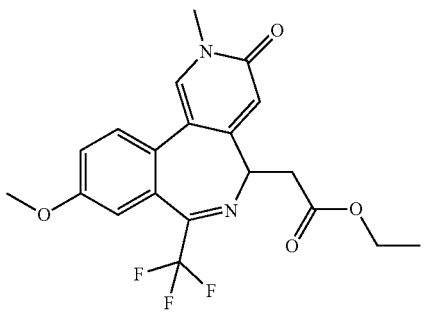 [SMILES: CCOC(=O)CC1N=C(C(F)(F)F)c2cc(OC)ccc2-c2cn(C)c(=O)cc21]

$^1$H-NMR (DMSO-d$_6$, 400 MHz) δ (ppm): 8.06 (s, 1H), 7.68 (d, J=8.8 Hz, 1H), 7.37-7.32 (m, 1H), 7.11 (s, 1H), 6.40 (s, 1H), 4.30-4.25 (m, 1H), 4.12-3.90 (m, 2H), 3.81 (s, 3H), 3.46 (s, 3H), 3.30-3.12 (m, 2H), 1.14 (t. J=6.8 Hz, 3H). MS (ESI): mass calculated for $C_{20}H_{19}F_3N_2O_4$, 408.1; m/z found, 409.1[M+H]$^+$.

Example 19

±Ethyl-2-(9-methoxy-2,7-dimethyl-3-oxo-3,5-dihydro-2H-benzo[c]pyrido[3,4-e]azepin-5-yl)acetate

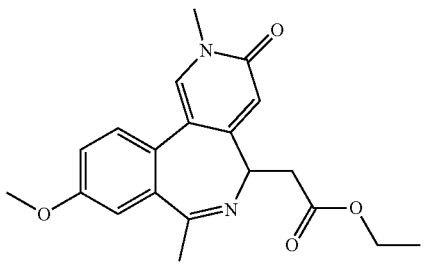 [SMILES: CCOC(=O)CC1N=C(C)c2cc(OC)ccc2-c2cn(C)c(=O)cc21]

$^1$H-NMR (DMSO-d$_6$, 400 MHz) δ (ppm): 7.90 (s, 1H), 7.51 (d, J=8.8 Hz, 1H), 7.23-7.22 (m, 1H), 7.16-7.13 (m, 1H), 6.24 (s, 1H), 4.03-3.99 (m, 3H), 3.83 (s, 3H), 3.44 (s, 3H), 3.05-3.01 (m, 2H), 2.24 (s, 3H), 1.12 (t, J=7.6 Hz, 3H). MS (ESI): mass calculated for $C_{20}H_{22}N_2O_4$, 354.20; m/z found, 355.1 [M+H]$^+$.

Example 20

±Ethyl-2-(9-methoxy-2-methyl-7-(5-methylpyridin-2-yl)-3-oxo-3,5-dihydro-2H-benzo[c]pyrido[3,4-e]azepin-5-yl)acetate

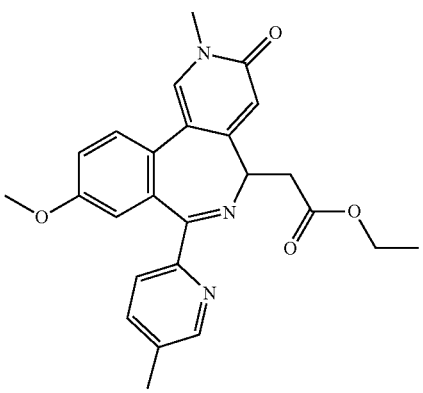 [SMILES: CCOC(=O)CC1N=C(c2ccc(C)cn2)c2cc(OC)ccc2-c2cn(C)c(=O)cc21]

$^1$HNMR: (400 MHz, DMSO-d$_6$) 8.29 (s, 1H), 7.98 (s, 1H), 7.98-7.76 (d, J=8 Hz, 1H), 7.69-7.67 (d, J=8 Hz, 1H), 7.58-7.56 (d, J=8 Hz, 1H), 7.21-7.18 (dd, 1H), 6.72-6.71 (m, 1H), 6.33 (s, 1H), 4.26-4.25 (m, 1H), 4.04-4.05 (m, 2H), 3.71 (s, 3H), 3.44 (s, 3H), 3.27-3.22 (dd, 1H), 3.15-3.13 (dd, 1H), 2.29 (s, 3H), 1.17-1.13 (t, J=5.2 Hz, 3H). MS (ESI): mass calculated for $C_{24}H_{25}N_3O_4$, 431.2; m/z found, 432.2 [M+H]$^+$.

Example 21

±Ethyl-2-(7-(4-chlorophenyl)-2-isopropyl-9-methoxy-3-oxo-3,5-dihydro-2H-benzo[c]pyrido[3,4-e]azepin-5-yl)acetate

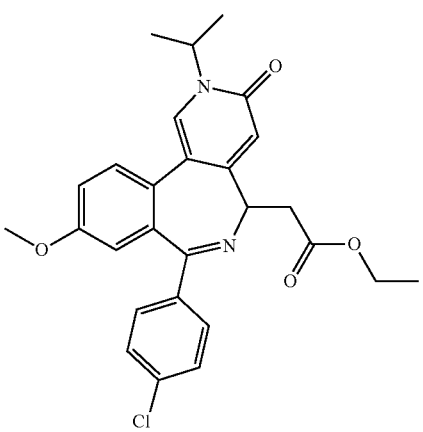 [SMILES: CCOC(=O)CC1N=C(c2ccc(Cl)cc2)c2cc(OC)ccc2-c2cn(C(C)C)c(=O)cc21]

MS (ESI): mass calculated for $C_{27}H_{27}ClN_2O_4$, 478.1; m/z found, 479.1[M+H]$^+$.

Example 22

±Ethyl-2-(7-(4-chlorophenyl)-9-fluoro-2-methyl-3-oxo-3,5-dihydro-2H-benzo[c]pyrido[3,4-e]azepin-5-yl)acetate

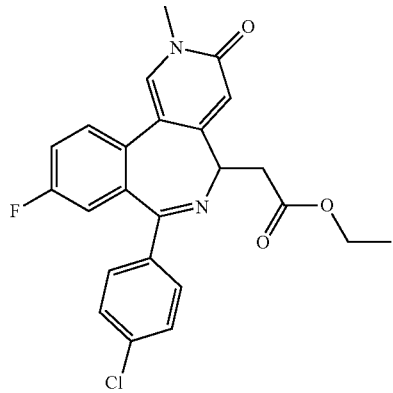 [SMILES: CCOC(=O)CC1N=C(c2ccc(Cl)cc2)c2cc(F)ccc2-c2cn(C)c(=O)cc21]

MS(ESI): mass calcd for $C_{24}H_{20}ClFN_2O_3$, 438.1; m/z found, 439.1 [M+H]$^+$.

Example 23

±Ethyl-2-(7-(2,6-difluorophenyl)-9-methoxy-2-methyl-3-oxo-3,5-dihydro-2H-benzo[c]pyrido[3,4-e]azepin-5-yl)acetate

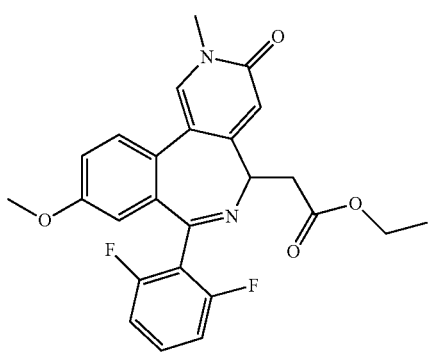 [SMILES: CCOC(=O)CC1N=C(c2c(F)cccc2F)c2cc(OC)ccc2-c2cn(C)c(=O)cc21]

MS(ESI): mass calcd for $C_{25}H_{22}F_2N_2O_4$, 452.1; m/z found, 453.2 [M+H]$^+$.

Example 24

±Ethyl-2-(7-(4-chloro-2-methylphenyl)-9-methoxy-2-methyl-3-oxo-3,5-dihydro-2H-benzo[c]pyrido[3,4-e]azepin-5-yl)acetate

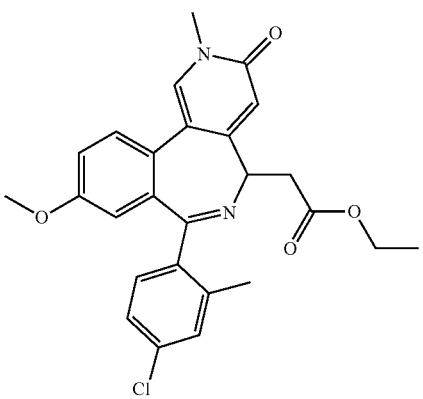 [SMILES: CCOC(=O)CC1N=C(c2ccc(Cl)cc2C)c2cc(OC)ccc2-c2cn(C)c(=O)cc21]

MS(ESI): mass calcd for $C_{26}H_{25}ClN_2O_4$, 464.2; m/z found, 465.2 [M+H]$^+$.

Example 25

±2-(7-(4-chlorophenyl)-9-methoxy-2-methyl-3-oxo-3,5dihydro2Hbenzo[c]pyrido[3,4-e]azepin-5-yl)-N-ethylacetamide

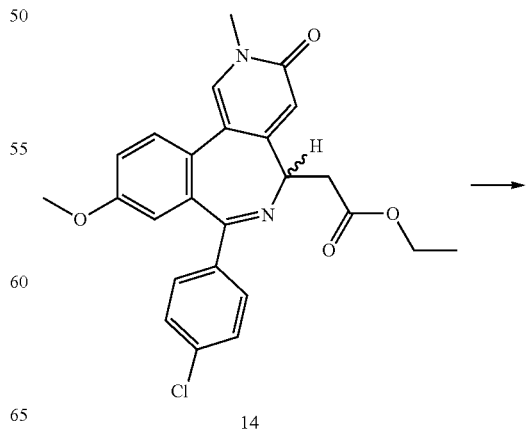

14

-continued

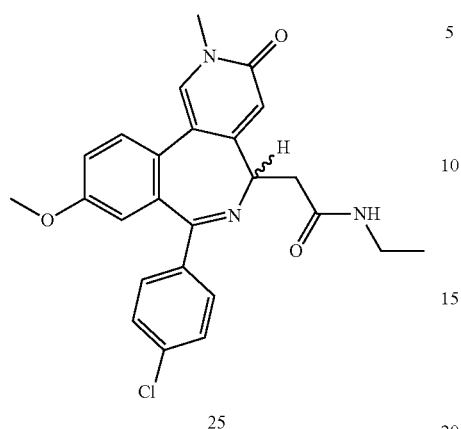

The compound was synthesized according to the procedure for example 8. $^1$H NMR (DMSO-$d_6$, 400 MHz): δ (ppm) 8.13 (br. s., 1H), 7.99 (s, 1H), 7.62 (d, J=8.4 Hz, 1H), 7.48-7.38 (m, 4H), 7.25-7.24 (m, 1H), 6.73 (d, J=2.0 Hz, 1H), 6.35 (s, 1H), 4.24 (t, J=7.2 Hz, 1H), 3.73 (s, 3H), 3.44 (s, 3H), 3.08-3.04 (m, 2H), 2.93-2.91 (m, 2H), 1.00 (t, J=7.6 Hz, 3H). MS (ESI): mass calcd. for $C_{25}H_{24}ClN_3O_3$, 449.1; m/z found, 450.4[M+H]$^+$.

Chiral Separation Conditions, 25A and 25B
Analytical Conditions:
Column: chiralpak IA (250 mm×4.6 mm×5 im)
Mobile phase: MtBe:IPA with 0.1% TFA (70:30)
Flow rate: 1.0 mL/min; Injection Volume: 20.00 ul
PDA detector, wavelength: 261.0 nm Example 25A (S)-2-(7-(4-chlorophenyl)-9-methoxy-2-methyl-3-oxo-3,5-dihydro-2H-benzo[c]pyrido[3,4-e]azepin-5-yl)-N-ethylacetamide

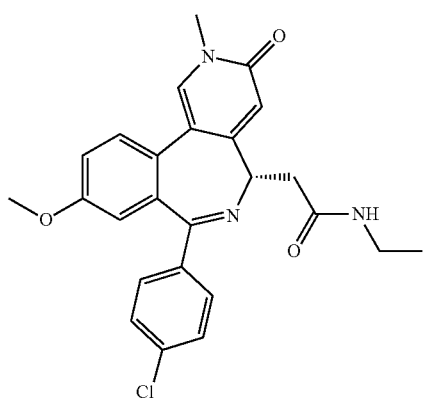 [SMILES: CCNC(=O)C[C@@H]1N=C(c2ccc(Cl)cc2)c2cc(OC)ccc2-c2cn(C)c(=O)cc21]

MS (ESI): mass calcd. for $C_{25}H_{24}ClN_3O_3$, 449.1; m/z found, 450.2[M+H]$^+$.

Example 25B (R)-2-(7-(4-chlorophenyl)-9-methoxy-2-methyl-3-oxo-3,5-dihydro-2H-benzo[c]pyrido[3,4-e]azepin-5-yl)-N-ethylacetamide

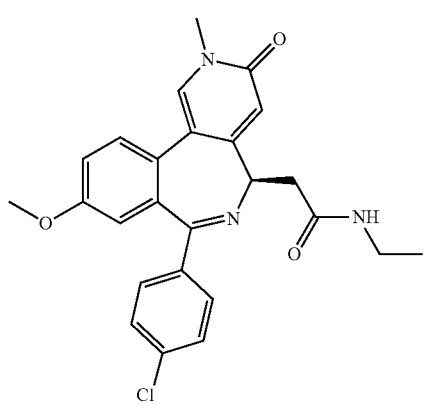 [SMILES: CCNC(=O)C[C@H]1N=C(c2ccc(Cl)cc2)c2cc(OC)ccc2-c2cn(C)c(=O)cc21]

MS (ESI): mass calcd. for $C_{25}H_{24}ClN_3O_3$, 449.1; m/z found, 450.2[M+H]$^+$.

The following compounds were synthesized using the procedure for synthesizing 25

Example 26

±2-(7-cyclohexyl-9-methoxy-2-methyl-3-oxo-3,5-dihydro-2H-benzo[c]pyrido[3,4-e]azepin-5-yl)-N-ethylacetamide

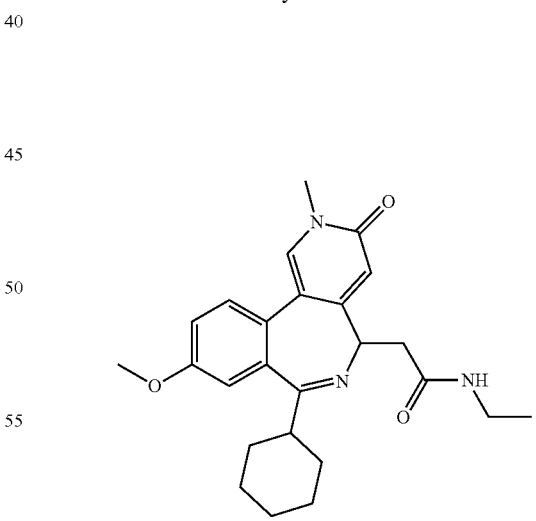

$^1$H NMR (DMSO-$d_6$), δ (ppm): 8.02 (br.s., 1H) 7.90 (s, 1H) 7.48-7.46 (d J=8.4 Hz, 1H) 7.16-7.15 (m, 1H) 7.12-7.10 (m, 1H), 6.28 (s, 11H), 4.01 (t, J=6.8 Hz, 1H), 3.83 (s, 3H), 3.43 (s, 3H), 3.04-2.97 (m, 2H), 2.89-2.70 (m, 3H), 1.82-1.00 (m, 9H), 0.96 (t, J=7.2 Hz, 3H), 0.67-0.59 (m, 1H). MS(ESI): mass calcd for $C_{25}H_{31}N_3O_3$, 421.2; m/z found, 422.5[M+H]$^+$.

Compound 26 was chiral separated (26A and 26B) following the procedures used for separating 25A and 25B

Example 26A (S)-2-(7-cyclohexyl-9-methoxy-2-methyl-3-oxo-3,5-dihydro-2H-benzo[c]pyrido[3,4-e]azepin-5-yl)-N-ethylacetamide

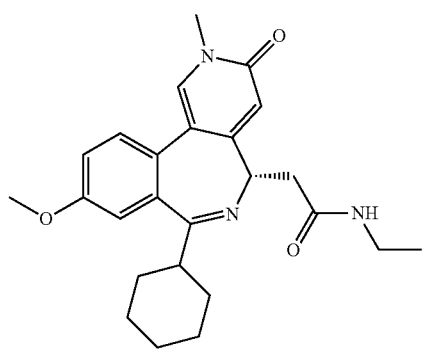 [SMILES: CCNC(=O)C[C@@H]1N=C(C2CCCCC2)c2cc(OC)ccc2-c2cn(C)c(=O)cc21]

MS(ESI): mass calcd for $C_{25}H_{31}N_3O_3$, 421.2; m/z found, 422.5[M+H]$^+$.

Example 26B (R)-2-(7-cyclohexyl-9-methoxy-2-methyl-3-oxo-3,5-dihydro-2H-benzo[c]pyrido[3,4-e]azepin-5-yl)-N-ethylacetamide

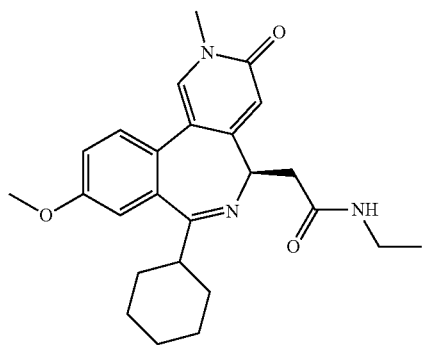 [SMILES: CCNC(=O)C[C@H]1N=C(C2CCCCC2)c2cc(OC)ccc2-c2cn(C)c(=O)cc21]

MS(ESI): mass calcd for $C_{25}H_{31}N_3O_3$, 421.2; m/z found, 422.5[M+H]$^+$.

Example 27

±2-(9-methoxy-2-methyl-3-oxo-7-(pyridin-2-yl)-3,5-dihydro-2H-benzo[c]pyrido[3,4-e]azepin-5-yl)-N-ethylacetamide

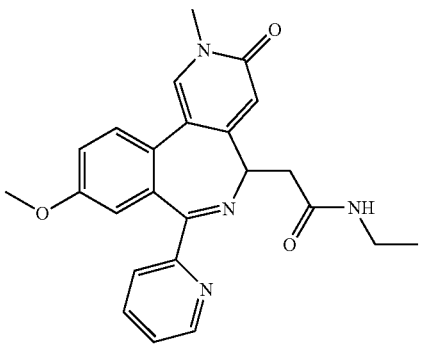 [SMILES: CCNC(=O)CC1N=C(c2ccccn2)c2cc(OC)ccc2-c2cn(C)c(=O)cc21]

$^1$H NMR (DMSO-d$_6$): δ (ppm) 8.45 (d, J=4 Hz, 1H), 8.14 (br. s., 1H), 7.97 (s, 1H), 7.92-7.82 (m, 2H), 7.57 (d, J=12 Hz, 1H), 7.42-7.39 (m, 1H), 7.20-7.18 (m, 1H), 6.71 (s, 1H), 6.36 (s, 1H), 4.31 (t, J=6.4 Hz, 1H), 3.71 (s, 3H), 3.44 (s, 3H), 3.08-3.05 (m, 2H), 2.94-2.93 (m, 2H), 1.01 (t, J=7.2 Hz, 3H). MS (ESI): mass calculated for $C_{24}H_{24}N_4O_3$, 416.1; m/z found, 417.3.1[M+H]$^+$.

Compound 27 was chiral separated (27A and 27B) following the procedures used for separating 25A and 25B

Example 27A (S)-2-(9-methoxy-2-methyl-3-oxo-7-(pyridin-2-yl)-3,5-dihydro-2H-benzo[c]pyrido[3,4-e]azepin-5-yl)-N-ethylacetamide

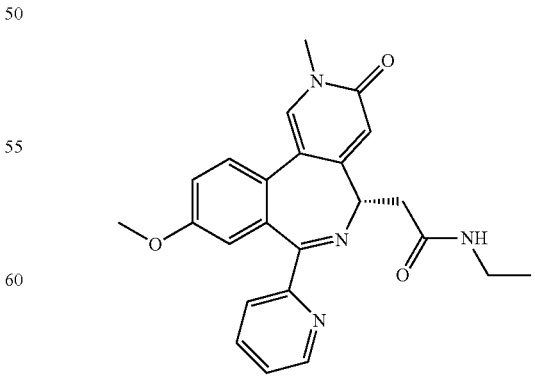

MS (ESI): mass calculated for $C_{24}H_{24}N_4O_3$, 416.1; m/z found, 417.3.1[M+H]$^+$.

Example 27B (R)-2-(9-methoxy-2-methyl-3-oxo-7-(pyridin-2-yl)-3,5-dihydro-2H-benzo[c]pyrido[3,4-e]azepin-5-yl)-N-ethylacetamide

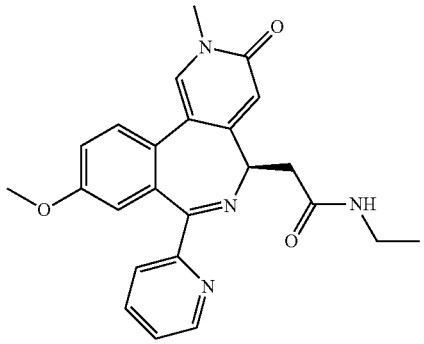 [SMILES: CCNC(=O)C[C@H]1N=C(c2ccccn2)c2cc(OC)ccc2-c2cn(C)c(=O)cc21]

MS (ESI): mass calculated for $C_{24}H_{24}N_4O_3$, 416.1; m/z found, 417.3, $[M+H]^+$.

Example 28

±2-(7-(4-chlorophenyl)-9-methoxy-2-methyl-3-oxo-3,5-dihydro-2H-benzo[c]pyrido[3,4-e]azepin-5-yl)acetamide

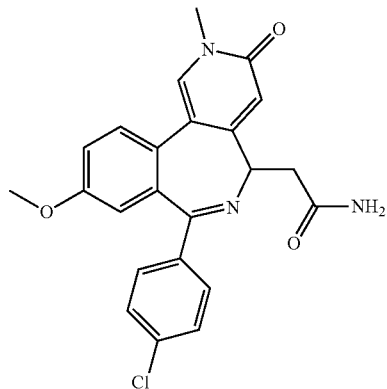 [SMILES: COc1ccc2c(c1)C(c1ccc(Cl)cc1)=NC(CC(N)=O)c1cc(=O)n(C)cc1-2]

$^1$H NMR (DMSO-d$_6$): δ (ppm) 12.28 (s, 1H), 8.01 (s, 1H), 7.63 (d, J=8.4 Hz, 1H), 7.45-7.40 (m, 4H), 7.26-7.23 (m, 1H), 6.74-6.71 (m, 1H), 6.31 (s, 1H), 4.17 (t, J=3.8 Hz, 1H), 3.73 (s, 3H), 3.45 (s, 3H), 3.13-3.08 (m, 3H). MS (ESI): mass calcd. for $C_{23}H_{20}ClN_3O_3$, 421.8; m/z found, 423.1 $[M+H]^+$.

Example 29

±2-(7-(4-chlorophenyl)-9-hydroxy-2-methyl-3-oxo-3,5-dihydro-2H-benzo[c]pyrido[3,4-e]azepin-5-yl)-N-ethylacetamide

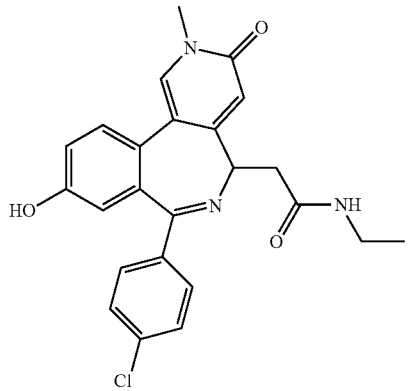 [SMILES: CCNC(=O)CC1N=C(c2ccc(Cl)cc2)c2cc(O)ccc2-c2cn(C)c(=O)cc21]

$^1$H NMR (DMSO-d$_6$, 400 MHz) δ (ppm): 9.79 (s, 1H), 8.12 (br.s., 1H), 7.94 (s, 1H), 7.5 (d, J=8.8 Hz, 1H), 7.45-7.38 (m, 4H), 7.04-7.01 (m, 1H), 6.60-6.59 (m, 1H), 6.33 (s, 1H), 4.22 (t, J=7.2 Hz, 1H), 3.43 (s, 3H), 3.08-3.03 (m, 2H), 2.93-2.88 (m, 2H), 1.00 (t, J=7.2 Hz, 3H). MS (ESI): mass calculated for $C_{24}H_{22}ClN_3O_3$, 435.90; m/z found, 436.1$[M+H]^+$.

Example 30

±2-(7-(cyclopropylmethyl)-9-methoxy-2-methyl-3-oxo-3,5-dihydro-2H-benzo[c]pyrido[3,4-e]azepin-5-yl)-N-ethylacetamide

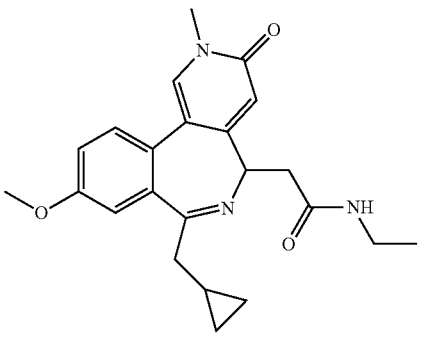

$^1$H NMR (DMSO-d 400 MHz): δ (ppm) 8.03 (br. s, 1H), 7.91 (s, 1H), 7.49 (d, J=8.8 Hz, 1H), 7.20 (d, J=2.8 Hz, 1H), 7.13 (dd, J1=2.4 Hz, J2=8.8 Hz, 1H), 6.28 (s, 1H), 4.05 (t, J=7.2 Hz, 1H), 3.83 (s, 3H), 3.44 (s, 3H), 3.10-2.95 (m, 2H), 2.85-2.76 (m, 3H), 2.34-2.25 (m, 1H), 0.96 (t, J=7.2 Hz, 3H), 0.65-0.55 (m, 1H), 0.24-0.15 (m, 2H), (−) 0.05-(−)0.12 (m, 2H). MS (ESI): mass calcd. for $C_{23}H_{27}N_3O_3$, 393.2; m/z found, 394.2 $[M+H]^+$.

Compound 30 was chiral separated (30A and 30B) following the procedures used for separating 25A and 25B

Example 30A (S)-2-(7-(cyclopropylmethyl)-9-methoxy-2-methyl-3-oxo-3,5-dihydro-2H-benzo[c]pyrido[3,4-e]azepin-5-yl)-N-ethylacetamide

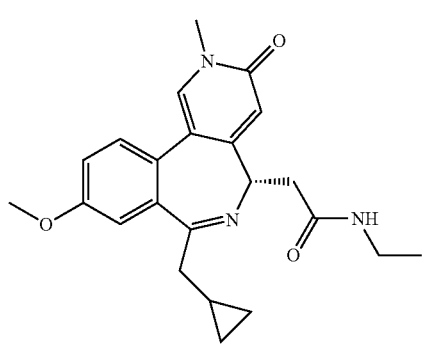 [SMILES: CCNC(=O)C[C@@H]1N=C(CC2CC2)c2cc(OC)ccc2-c2cn(C)c(=O)cc21]

MS (ESI): mass calcd. for $C_{23}H_{27}N_3O_3$, 393.2; m/z found, 394.2 [M+H]$^+$.

Example 30B (R)-2-(7-(cyclopropylmethyl)-9-methoxy-2-methyl-3-oxo-3,5-dihydro-2H-benzo[c]pyrido[3,4-e]azepin-5-yl)-N-ethylacetamide

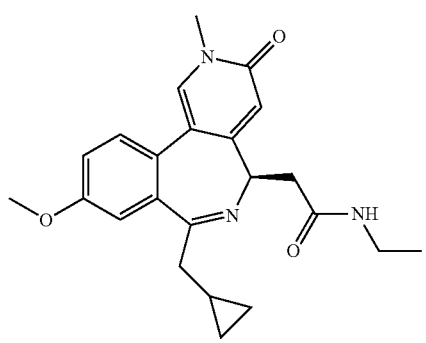 [SMILES: CCNC(=O)C[C@H]1N=C(CC2CC2)c2cc(OC)ccc2-c2cn(C)c(=O)cc21]

MS (ESI): mass calcd. for $C_{23}H_{27}N_3O_3$, 393.2: m/z found, 394.2 [M+H]$^+$.

Example 31

±2-(7-(4-chlorophenyl)-9-(difluoromethoxy)-2-methyl-3-oxo-3,5-dihydro-2H-benzo[c]pyrido[3,4-e]azepin-5-yl)-N-ethylacetamide

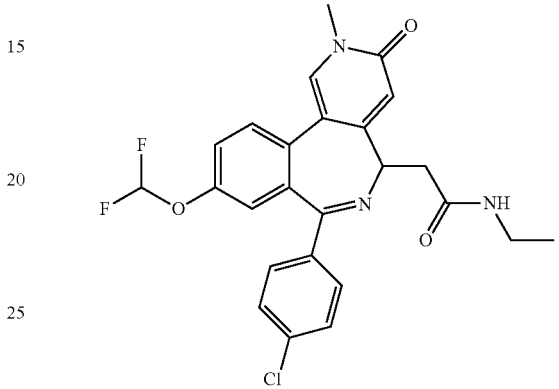

MS (ESI): mass calculated for $C_{25}H_{22}ClF_2N_3O$, 485.1; m/z found, 486.1[M+H]$^+$.

Example 32

±2-(9-methoxy-2-methyl-3-oxo-7-(trifluoromethyl)-3,5-dihydro-2H-benzo[c]pyrido[3,4-e]azepin-5-yl)-N-ethylacetamide

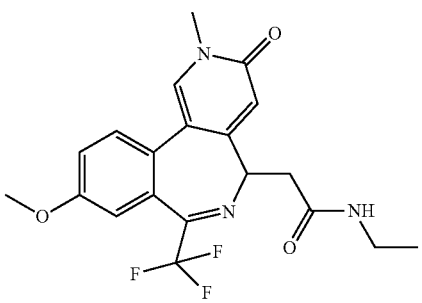 [SMILES: CCNC(=O)CC1N=C(C(F)(F)F)c2cc(OC)ccc2-c2cn(C)c(=O)cc21]

$^1$H-NMR (DMSO-d$_6$, 400 MHz) δ (ppm): 8.10 (t, J=5.2 Hz, 1H), 8.04 (s, 1H), 7.68 (d, J=8.8 Hz, 1H), 7.38-7.32 (m, 1H), 7.11 (s, 1H), 6.39 (s, 1H), 4.35-4.30 (m, 1H), 3.85 (s, 3H), 3.44 (s, 3H), 3.08-2.90 (m, 4H), 0.97 (t, J=6.8 Hz, 3H). MS (ESI): mass calculated for $C_{20}H_{20}F_3N_3O_3$, 407.1; m/z found, 408.3[M+H]$^+$.

Compound 32 was chiral separated (32A and 32B) following the procedures used for separating 25A and 25B

Example 32A (S)-2-(9-methoxy-2-methyl-3-oxo-7-(trifluoromethyl)-3,5-dihydro-2H-benzo[c]pyrido[3,4-e]azepin-5-yl)-N-ethylacetamide

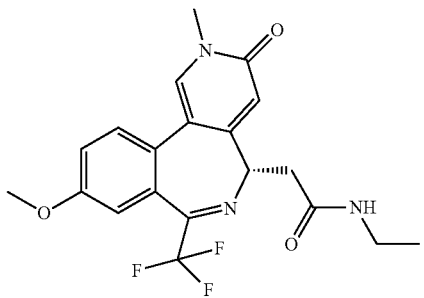 [SMILES: CCNC(=O)C[C@@H]1N=C(C(F)(F)F)c2cc(OC)ccc2-c2cn(C)c(=O)cc21]

MS (ESI): mass calculated for $C_{20}H_{20}F_3N_3O_3$, 407.1; m/z found, 408.3[M+H]$^+$.

Example 32B (R)-2-(9-methoxy-2-methyl-3-oxo-7-(trifluoromethyl)-3,5-dihydro-2H-benzo[c]pyrido[3,4-e]azepin-5-yl)-N-ethylacetamide

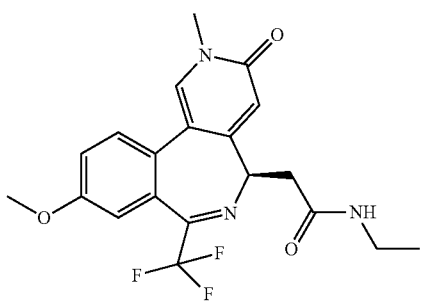 [SMILES: CCNC(=O)C[C@H]1N=C(C(F)(F)F)c2cc(OC)ccc2-c2cn(C)c(=O)cc21]

MS (ESI): mass calculated for $C_{20}H_{20}F_3N_3O_3$, 407.1; m/z found, 408.3[M+H]$^+$.

Example 33

±2-(7-(4-cyanophenyl)-9-methoxy-2-methyl-3-oxo-3,5-dihydro-2H-benzo[c]pyrido[3,4-e]azepin-5-yl)-N-ethylacetamide

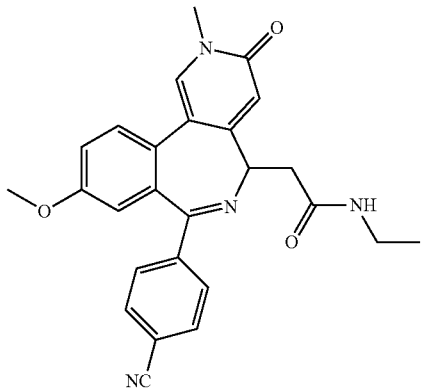 [SMILES: CCNC(=O)CC1N=C(c2ccc(C#N)cc2)c2cc(OC)ccc2-c2cn(C)c(=O)cc21]

$^1$H NMR (DMSO-d$_6$), δ (ppm): 8.15 (t, J=7.4 Hz, 1H), 8.00 (s, 1H), 7.84 (d, J=8.4 Hz, 1H), 7.64 (d, J=8.8 Hz, 1H), 7.56 (d, J=8.4 Hz, 2H), 7.41-7.45 (m, 1H), 7.25-7.28 (m, 1H), 6.71 (d, J=2.8 Hz, 1H), 6.36 (s, 1H), 4.28 (t, J=7.2 Hz, 1H), 3.73 (s, 3H), 3.44 (s, 3H), 3.03-3.08 (m, 2H), 2.92-2.95 (m, 2H), 1.01 (t, J=8.0 Hz, 3H); MS(ESI): mass calcd for $C_{26}H_{24}N_4O_3$, 440.1; m/z found, 441.2[M+H]$^+$.

Example 34

±2-(9-methoxy-2-methyl-7-(5-methylpyridin-2-yl)-3-oxo-3,5-dihydro-2H-benzo[c]pyrido[3,4-e]azepin-5-yl)-N-ethylacetamide

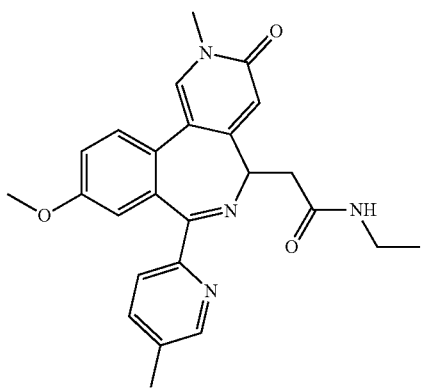 [SMILES: CCNC(=O)CC1N=C(c2ccc(C)cn2)c2cc(OC)ccc2-c2cn(C)c(=O)cc21]

$^1$HNMR: (400 MHz, DMSO-d$_6$), δ (ppm): 8.29 (s, 1H), 8.13 (br.s., 1H), 7.96 (s, 1H), 7.81 (d, J=8 Hz, 1H), 7.68 (d, J=5.2 Hz, 1H), 7.55 (d, J=8 Hz, 1H), 7.19-7.17 (m, 1H), 6.39 (s, 1H), 4.28 (t, J=6.4 Hz, 1H), 3.71 (s, 3H), 3.44 (s, 3H), 3.08-3.04 (m, 2H), 2.93-2.91 (m, 2H), 2.29 (s, 3H), 1.03 (t, J=8 Hz, 3H). MS(ESI): mass calcd for $C_{25}H_{26}N_4O_3$, 430.1; m/z found, 431.2[M+H]$^+$.

Example 35

±2-(7-(4-chlorophenyl)-2-methyl-3-oxo-9-(trifluoromethyl)-3,5-dihydro-2H-benzo[c]pyrido[3,4-e]azepin-5-yl)-N-ethylacetamide

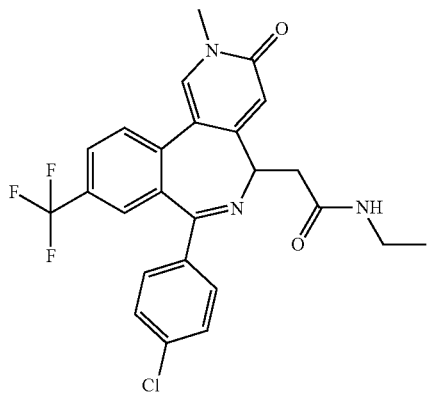 [SMILES: CCNC(=O)CC1N=C(c2ccc(Cl)cc2)c2cc(C(F)(F)F)ccc2-c2cn(C)c(=O)cc21]

$^1$H NMR (DMSO-d$_6$, 400 MHz): δ (ppm) 8.20 (s, 1H), 8.13 (br.s., 1H), 8.01 (d, J=8.0 Hz, 1H), 7.94 (d, J=8.0 Hz, 1H), 7.53 (s, 1H), 7.46 (d, J=8.0 Hz, 2H), 7.37 (d, J=8.0 Hz, 2H), 6.39 (s, 1H), 4.23 (t, J=8.0 Hz, 1H), 3.47 (s, 3H), 3.09-3.03 (m, 2H), 2.95 (d, J=8.0 Hz, 2H), 1.00 (t, J=8.0 Hz, 3H). MS(ESI): mass calcd for C$_{25}$H$_{21}$ClF$_3$N$_3$O$_2$, 487.1; m/z found, 488.3[M+H]$^+$ LCMS: 488.3 [M+H].

Example 36

±2-(7-(4-chlorophenyl)-2-isopropyl-9-methoxy-3-oxo-3,5-dihydro-2H-benzo[c]pyrido[3,4-e]azepin-5-yl)-N-ethylacetamide

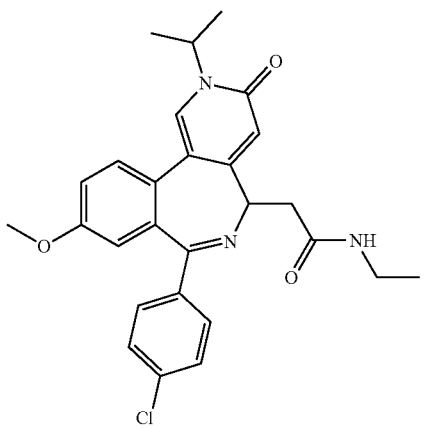 [SMILES: CCNC(=O)CC1N=C(c2ccc(Cl)cc2)c2cc(OC)ccc2-c2cn(C(C)C)c(=O)cc21]

$^1$H NMR (DMSO-d$_6$, 400 MHz): 8.13 (br. s., 1H), 7.89 (s, 1H), 7.66 (d, J=8.4 Hz, 1H), 7.50-7.40 (m, 4H), 7.27-7.23 (m, 1H), 6.75 (d, J=2.4 Hz, 1H), 6.35 (s, 1H), 5.10-4.95 (m, 1H), 4.25 (t, J=7.2 Hz, 1H), 3.74 (s, 3H), 3.10-3.05 (m, 2H), 2.92 (d, J=6.8 Hz, 2H), 1.38 (d, J=6.4 Hz, 3H), 1.26 (d, J=7.2 Hz, 3H), 1.01 (t, J=7.6 Hz, 3H); MS(ESI): mass calcd for C$_{27}$H$_{28}$ClN$_3$O$_3$, 477.1; m/z found, 478.1[M+H]$^+$.

Example 37

±2-(7-(4-chlorophenyl)-9-fluoro-2-methyl-3-oxo-3,5-dihydro-2H-benzo[c]pyrido[3,4-e]azepin-5-yl)-N-ethylacetamide

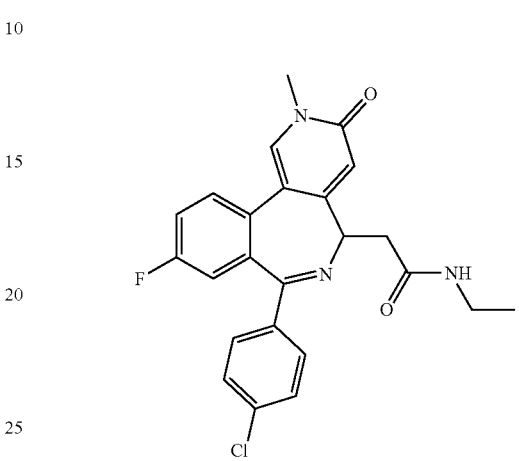

$^1$H NMR (DMSO-d$_6$, 400 MHz): δ (ppm) 8.13 (1, J=8 Hz, 1H), 8.06 (s, 1H), 7.77-7.73 (m, 1H), 7.56-7.51 (m, 1H), 7.46-7.36 (m, 4H), 7.11-7.086 (dd, J=4 Hz, J=4 Hz, 1H), 6.36 (s, 1H), 4.22 (t, J=8.0 Hz, 1H), 3.45 (s, 3H), 3.09-3.03 (m, 2H), 2.94-2.92 (m, 2H), 1.00 (t, 1=8.0 Hz 3H). MS(ESI): mass calcd for C$_{24}$H$_{21}$ClFN$_3$O$_2$, 437.1; m/z found, 438.1 [M+H]$^+$.

Example 38

±2-(7-(2,6-difluorophenyl)-9-methoxy-2-methyl-3-oxo-3,5-dihydro-2H-benzo[c]pyrido[3,4-e]azepin-5-yl)-N-ethylacetamide

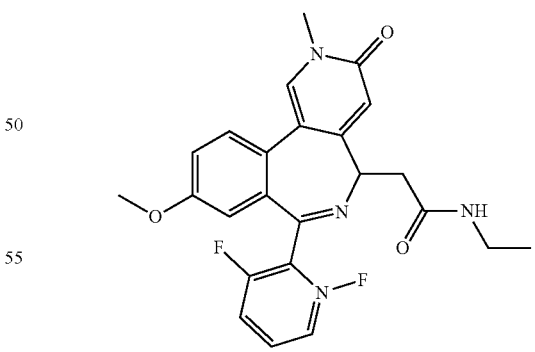

$^1$H NMR (DMSO-d$_6$, 400 MHz): (ppm) 8.06-8.05 (m, 2H), 7.64 (d, J=8.4 Hz, 1H), 7.56-7.45 (m, 1H), 7.23-7.20 (m, 1H), 7.10-7.08 (m, 2H), 6.59 (s, 1H), 6.36 (s, 1H), 4.33 (t, J=6.8 Hz, 1H), 3.73 (s, 3H), 3.48 (s, 3H), 3.05-3.03 (m, 2H), 2.89 (d, J=Hz, 2H), 1.00 (t, J=7.2 Hz, 3H). MS (ESI): mass calculated for C$_{25}$H$_{23}$F$_2$N$_3$O$_3$, 451.2; m/z found, 452.2 [M+H]$^+$.

Example 39

±2-(7-(4-chloro,2-methylphenyl)-9-methoxy-2-methyl-3-oxo-3,5-dihydro-2H-benzo[c]pyrido[3,4-e]azepin-5-yl)-N-ethylacetamide

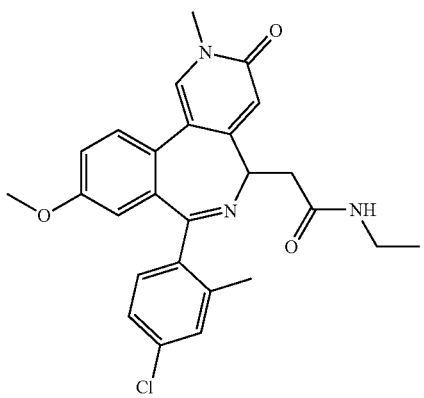 [SMILES: CCNC(=O)CC1N=C(c2ccc(Cl)cc2C)c2cc(OC)ccc2-c2cn(C)c(=O)cc21]

$^1$H NMR (DMSO-d$_6$, 400 MHz), δ (ppm): 8.09 (br. s., 1H), 8.03 (s, 1H), 7.62 (d, J=8.8 Hz, 1H), 7.27 (s, 1H), 7.25-7.20 (m, 2H), 6.98 (d, J=6.4 Hz, 1H), 6.44 (d, J=2.4 Hz, 1H), 6.31 (s, 1H), 4.28 (t, J=8.4 Hz, 1H), 3.67 (s, 3H), 3.48 (s, 3H), 3.10-2.78 (m, 4H), 1.94 (s, 3H), 1.00 (t, J=7.2 Hz, 3H); MS(ESI): mass calcd for C$_{26}$H$_{26}$ClN$_3$O$_3$, 463.1; m/z found, 464.1 [M+H]$^+$.

Example 40

±2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide

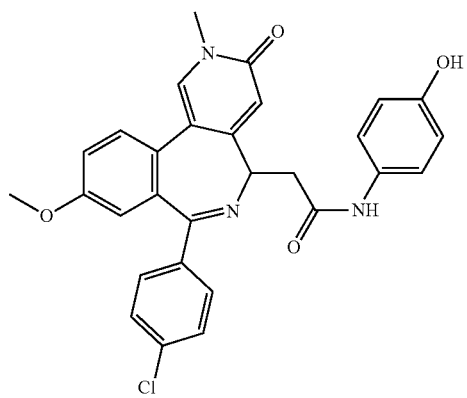 [SMILES: COc1ccc2c(c1)C(c1ccc(Cl)cc1)=NC(CC(=O)Nc1ccc(O)cc1)c1cc(=O)n(C)cc1-2]

$^1$H NMR (DMSO-d$_6$): –δ (ppm) 9.96 (s, 1H), 9.11 (br.s., 1H), 8.02 (s, 1H), 7.64 (d, J=8.4 Hz, 1H), 7.45-7.40 (m, 4H), 7.33 (d, J=7.6 Hz, 2H), 7.26-7.24 (m, 1H), 6.73 (d, J=2.8 Hz, 1H), 6.66 (d, J=8.4 Hz, 2H), 6.41 (s, 1H), 4.31 (t, J=6.8 Hz, 1H), 3.73 (s, 3H), 3.45 (s, 3H), 3.12-3.08 (m, 2H); MS (ESI): mass calcd for C$_{29}$H$_{24}$ClN$_3$O$_4$, 513.1; m/z found, 514.4 [M+H]$^+$.

Compound 40 was chiral separated (40A and 40B) following the procedures used for separating 25A and 25B

Example 40A (S)-2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide

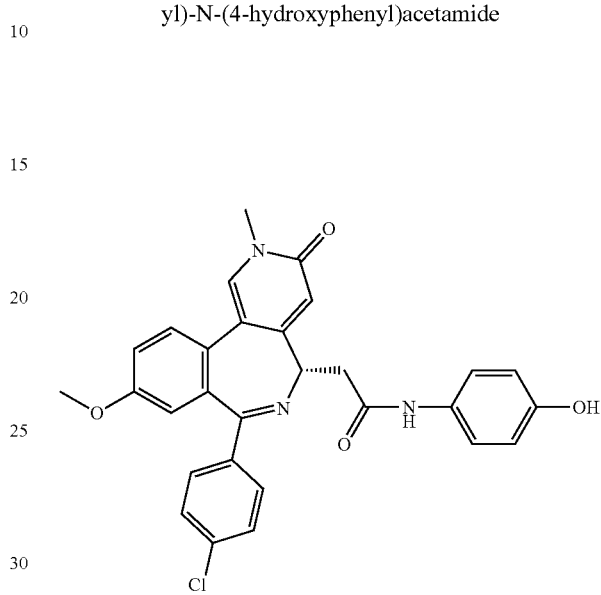

MS (ESI): mass calcd for C$_{29}$H$_{24}$ClN$_3$O$_4$, 513.1; m/z found, 514.4 [M+H]$^+$.

Example 40B (R)-2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide

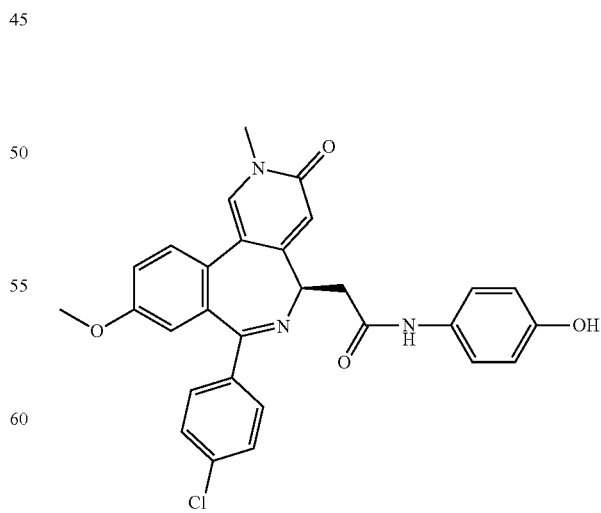

MS (ESI): mass calcd for C$_{29}$H$_{24}$ClN$_3$O$_4$, 513.1; m/z found, 514.4 [M+H]$^+$.

Example 41

±7-(4-chlorophenyl)-9-methoxy-2,5-dimethyl-2H-benzo[c]pyrido[3,4-e]azepin-3(5H)-one

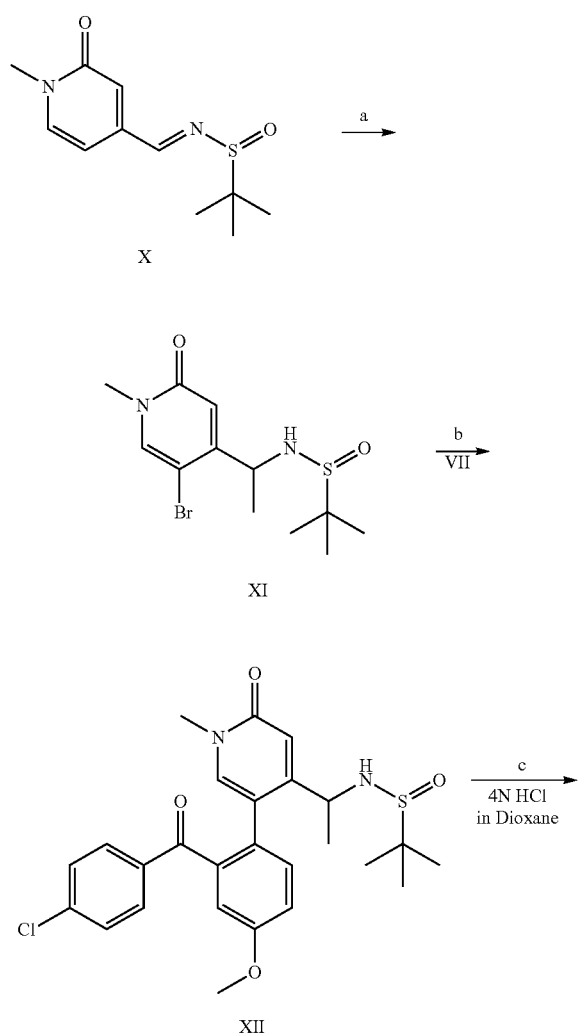

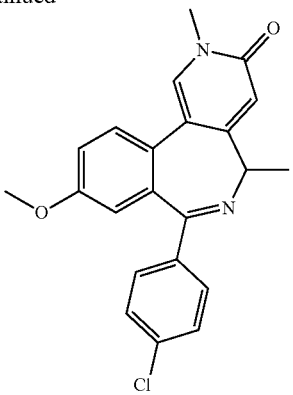

41

Step a: N-(1-(5-bromo-1-methyl-2-oxo-1,2-dihydropyridin-4-yl)ethyl)-2-methylpropane-2-sulfinamide To a stirred solution of (E)-N-((5-bromo-1-methyl-2-oxo-1,2-dihydropyridin-4-yl)methylene)-2-methylpropane-2-sulfinamide (X, 0.3 g, 0.94 mmol) in dry THF was cooled to −78° C. and then methylmagnesium bromide (0.13 mL, 1.12 mmol) was added dropwise and stirred at same temperature for 2 h and then stirred at room temperature for another 1 h. Reaction mixture was quenched with ammonium chloride solution and extracted with ethylacetate (25 mL×2). The organic layer was dried, concentrated under vacuum and purified by column chromatography using methanol/DCM as eluent to get N-(1-(5-bromo-1-methyl-2-oxo-1,2-dihydropyridin-4-yl)ethyl)-2-methylpropane-2-sulfinamide (0.27 g, 86%) as yellow solid. MS (ESI): mass calcd for $C_{12}H_{19}BrN_2O_2S$, 334.0; m/z found, 335.0 [M+H]$^+$.

Step b: N-(1-(5-(2-(4-chlorobenzoyl)-4-methoxyphenyl)-1-methyl-2-oxo-1,2-dihydropyridin-4-yl)ethyl)-2-methylpropane-2-sulfinamide To a stirred solution of N-(1-(5-bromo-1-methyl-2-oxo-1,2-dihydropyridin-4-yl)ethyl)-2-methylpropane-2-sulfinamide (XI, 0.33 g, 0.98 mmol) and (4-chlorophenyl)(5-methoxy-2-(4,4,5,5-tetramethyl-1,3,2-dioxaborolan-2-yl)phenyl)methanone (VII, 0.441 g, 1.18 mmol) in toluene (20 mL) To this mixture, was added sodium bicarbonate (249 mg, 2.96 mmol) and Pd(PPh$_3$)$_4$ (0.114 g, 0.098 mmol) nitrogen was purged for 10 min at room temperature in inert condition. The reaction mixture was heated to 110° C. and stirred for 16 h. To the reaction mixture water was added and extracted with ethyl acetate, the organic layer was dried over by sodium sulfate and concentrated. The crude product was purified by column chromatography the product eluted at 6% of MeOH/DCM. to get the product (280 mg, 57% yield), MS (ESI): mass calcd. for $C_{26}H_{29}ClN_2O_4S$, 500.2; m/z found, 501.1 [M+H]$^+$.

Step C: 7-(4-chlorophenyl)-9-methoxy-2,5-dimethyl-2H-benzo[c]pyrido[3,4-e]azepin-3(5H)-one To a stirred solution of N-(1-(5-(2-(4-chlorobenzoyl)-4-methoxyphenyl)-1-methyl-2-oxo-1,2-dihydropyridin-4-yl)ethyl)-2-methylpropane-2-sulfinamide (XII, 0.280 g, 0.56 mmol) in 4N HCl in dioxane (5 mL) was stirred at room temperature for 1 h. After completion of reaction the solvent was evaporated then crude residue was basified with sodium bicarbonate and organic layer was extracted with DCM then dried over by sodium sulfate and concentrated and the crude was purified by column chromatography by using 5% methanol/DCM as eluent to get the compound 41 as pale yellow solid. (140 mg, 66% yield).

$^1$H NMR (DMSO-d$_6$, 400 MHz): δ (ppm) 7.98 (s, 1H), 7.60 (d, J=9.2 Hz, 1H), 7.46-7.41 (m, 4H), 7.25-7.20 (m, 1H), 6.74 (d, J=2.4 Hz, 1H), 6.35 (s, 1H), 3.94 (q, J=6.1 Hz, 1H), 3.73 (s, 3H), 3.45 (s, 3H), 1.62 (d, J=6.4 Hz, 3H). MS (ESI): mass calculated for C$_{22}$H$_{19}$ClN$_2$O$_2$, 378.1; m/z found, 379.1[M+H]$^+$.

Compound 41 was chiral separated (41A and 41B) following the procedures used for separating 25a and 25b

Example 41A (S)-7-(4-chlorophenyl)-9-methoxy-2,5-dimethyl-2H-benzo[c]pyrido[3,4-e]azepin-3(5H)-one

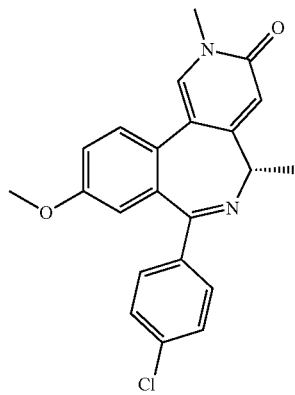

MS (ESI): mass calculated for C$_{22}$H$_{19}$ClN$_2$O$_2$, 378.1; m/z found, 379.1[M+H]$^+$.

Example 41B (R)-7-(4-chlorophenyl)-9-methoxy-2,5-dimethyl-2H-benzo[c]pyrido[3,4-e]azepin-3(5H)-one

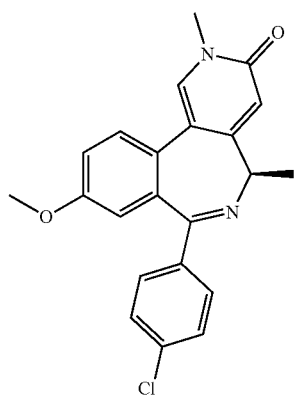

MS (ESI): mass calculated for C$_{22}$H$_{19}$ClN$_2$O$_2$, 378.1; m/z found, 379.1[M+H]$^+$.

Example 42

±7-(4-chlorophenyl)-9-methoxy-2-methyl-2H-benzo[c]pyrido[3,4-e]azepin-3(5H)-one

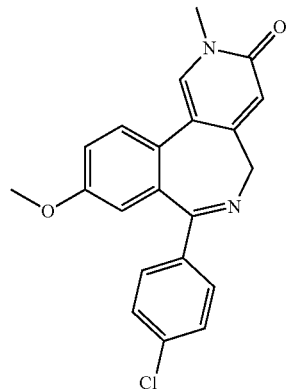 [SMILES: COc1ccc2c(c1)C(c1ccc(Cl)cc1)=NCc1cc(=O)n(C)cc1-2]

The compound was synthesized using the procedure in the example 41

$^1$H NMR (DMSO-d$_6$, 400 MHz): δ (ppm) 8.03 (s, 1H), 7.60 (d, J=8.8 Hz, 1H), 7.47-7.41 (m, 4H), 7.23 (dd, J=2.4 Hz, 8.8 Hz, 1H), 6.71 (d, J=2.8 Hz, 1H), 6.46 (s, 1H), 4.70 (d, J=10.0 Hz, 1H), 3.86 (d, J=10 Hz, 1H), 3.72 (s, 3H), 3.45 (s, 3H). MS (ESI): mass calcd. for C$_{21}$H$_{17}$ClN$_2$O$_2$, 364.1; m/z found, 365.1 [M+H]$^+$.

Example 43

±2-(7-(4-chlorophenyl)-2-methyl-3-oxo-9-(trifluoromethyl)-3,5-dihydro-2H benzo[c]pyrido[3,4-e]azepin-5-yl)acetic acid

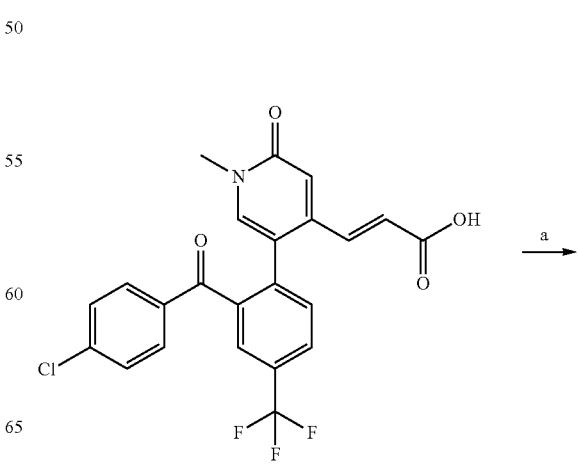

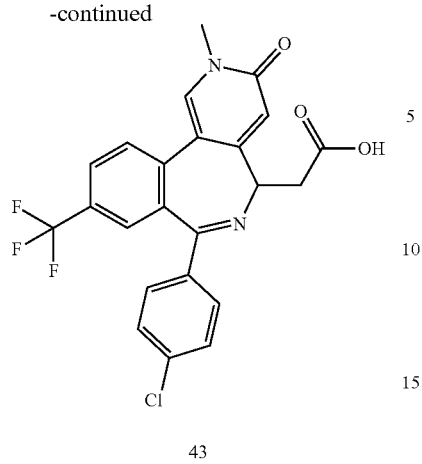

43

Step A: 2-(7-(4-chlorophenyl)2-methyl-3-oxo-9-(trifluoromethyl)-3,5-dihydro-2H-benzo[c]pyrido[3,4-e]azepin-5-yl)acetic add Ammonium formate (0.41 g, 0.650 mmol) was added to a stirred solution of 3-(5-(2-(4-chlorobenzoyl)-4-(trifluoromethyl)phenyl)-1-methyl-2-oxo-1,2-dihydropyridin-4-yl) acrylic acid (0.150 g, 0.325 mmol) dissolved in ethanol (5 mL), was carried out in seal tube at 90° C. After 15 h the reaction mixture was cooled to room temperature and concentrated to get mass, which was taken in ethyl acetate and water. The organic layer was separated and dried over sodium sulfate and concentrated to get residue. The crude was purified by comb flash eluting with 0-80% ethyl acetate/hexane. The pure fractions were concentrated to obtain 2-(7-(4-chlorophenyl)-2-methyl-3-oxo-9-(trifluoromethyl)-3,5-dihydro-2H-benzo[c]pyrido[3,4-e]azepin-5-yl)acetic acid (0.08 g, 57% yield) as a off-white solid. $^1$H NMR (DMSO-d$_6$, 400 MHz): δ (ppm) 12.32 (s, 1H), 8.01 (s, 1H), 8.02-8.00 (m, 1H), 7.96-7.94 (d, J=8 Hz, 1H), 7.54 (s, 1H), 7.50-7.48 (d, J=8 Hz, 2H), 7.39-7.37 (d, J=8 Hz, 2H), 6.36 (s, 1H), 4.176 (t, J=8 Hz, 1H), 3.47 (s, 3H), 3.17-3.12 (m, 2H); MS(ESI): mass calcd for C$_{23}$H$_{16}$ClF$_3$N$_2$O$_3$, 460.1; m/z found, 461.1[M+H]$^+$.

Example 44

±2-(7-(4-chlorophenyl)-9-methoxy-2-methyl-3-oxo-3,5-dihydro-2H-benzo[c]pyrido[3,4-e]azepin-5-yl) acetic acid

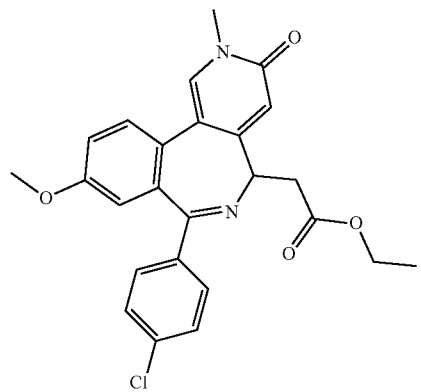

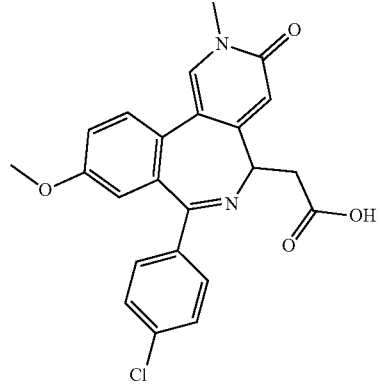

44

To a stirred solution of ethyl 2-(7-(4-chlorophenyl)-9-methoxy-2-methyl-3-oxo-3,5-dihydro-2H-benzo[c]pyrido[3,4-e]azepin-5-yl)acetate (2.1 g, 4.65 mmol) in THF (30 ml) was added 1N NaOH (9.3 ml, 9.31 mmol) and stirred at rt for 3 hours. Reaction mixture was neutralized with 1N HCl solution (9.3 ml) and extracted with 5% MeOH/DCM (50 ml×2). The organic layer was dried over sodium sulphate and concentrated under vacuum to get compound 44 (1.95 g, 98.9%) as off-white solid.

MS(ESI): mass calcd for C$_{23}$H$_{19}$ClN$_2$O$_4$, 422.1; m/z found, 423.1[M+H]$^+$.

Example 45

±tert-butyl ((7-(4-chlorophenyl)-9-methoxy-2-methyl-3-oxo-3,5-dihydro-2H-benzo[c]pyrido[3,4-e] azepin-5-yl)methyl)carbamate

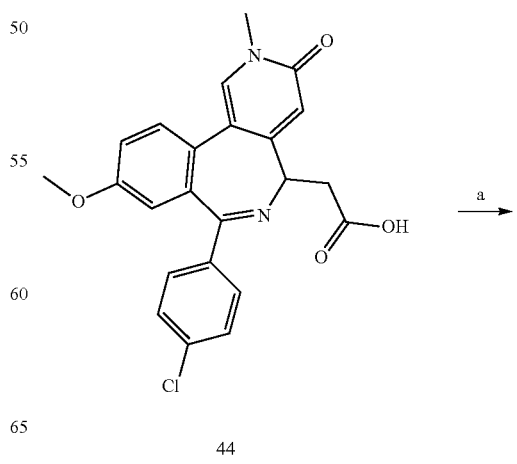

44

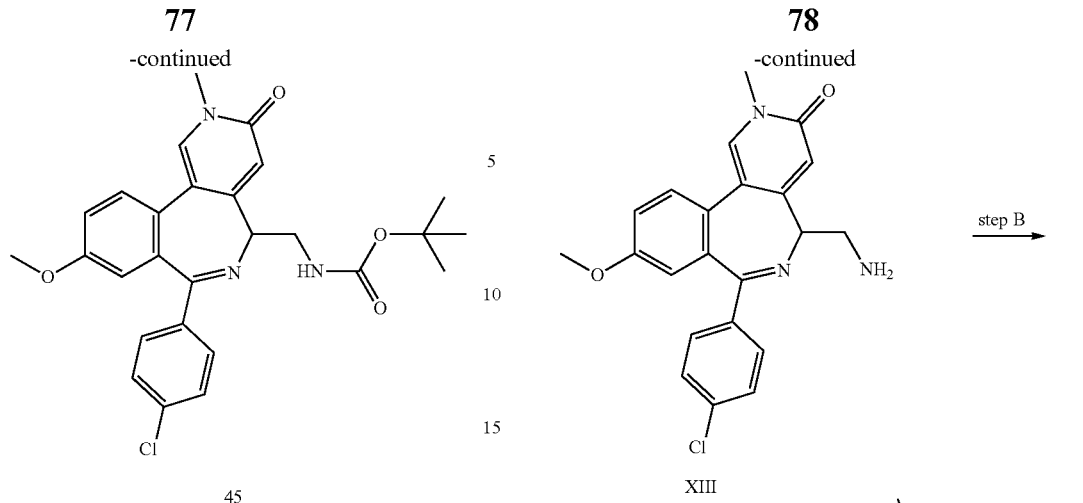

To a stirred solution of 2-(7-(4-chlorophenyl)-9-methoxy-2-methyl-3-oxo-3,5-dihydro-2H-benzo[c]pyrido[3,4-e]azepin-5-yl)acetic acid (example 44, 0.4 g, 0.945 mmol) in t-BuOH (20 mL), TEA (0.198 mL, 1.41 mmol), diphenylphosphoryl azide (0.225 mL, 1.04 mmol) at room temperature. The mixture was stirred at 105° C. for 24 h. The mixture was cooled to room temperature and concentrated under vacuum. The crude was dissolved in ethyl acetate and washed with saturated NaHCO$_3$ solution and brine, dried over sodium sulphate, concentrated under reduced pressure. The crude was purified by combiflash purifier by using 5-100% ethyl acetate/hexane as the eluent to get the product as off white solid. (0.15 g, 32% yield). $^1$H NMR (DMSO-d$_6$, 400 MHz): δ (ppm) 7.99 (s, 1H), 7.61 (d, J=8.4 Hz, 1H), 7.50 (d, J=8.4 Hz, 2H), 7.43 (d, J=8.8 Hz, 2H), 7.24-7.22 (m, 1H), 7.01-6.92 (m, 1H), 6.75 (d, J=2.8 Hz, 1H), 6.42 (s, 1H), 3.90-3.86 (m, 2H), 3.73 (s, 3H), 3.70-3.63 (m, 1H), 3.44 (s, 3H), 1.32 (s, 9H). MS (ESI): mass calcd. for C$_{27}$H$_{28}$ClN$_3$O$_4$, 493.2; m/z found, 494.1 [M+H]$^+$.

Example 46

±N-((7-(4-chlorophenyl)-9-methoxy-2-methyl-3-oxo-3,5-dihydro-2H-benzo[c]pyrido[3,4-e]azepin-5-yl)methyl)acetamide

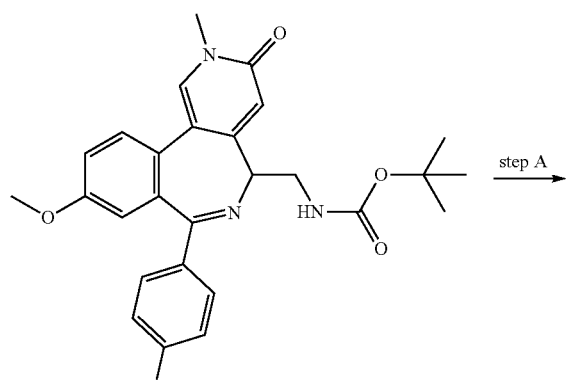

Example 45

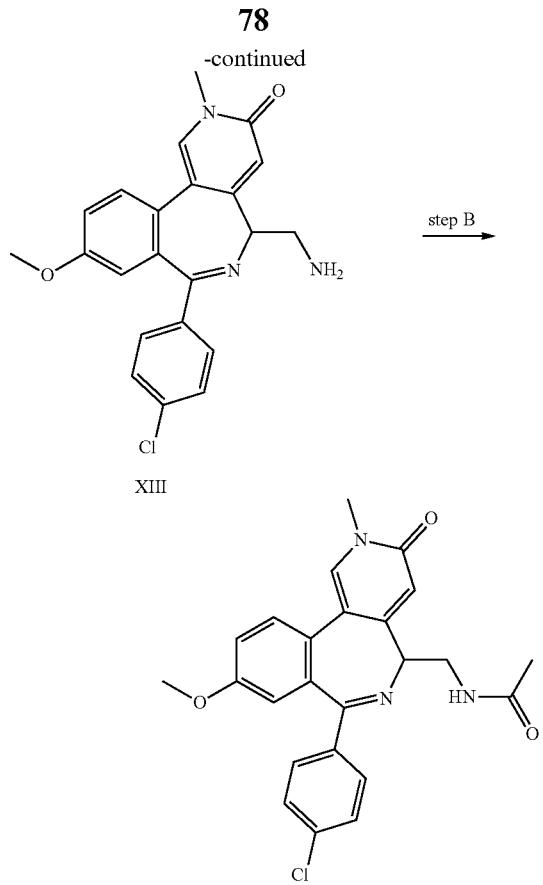

Example 46

Step A: 5-(aminomethyl)-7-(4-chlorophenyl)-9-methoxy-2-methyl-2H-benzo[c]pyrido[3,4-e]azepin-3(5H)-one hydrochloride To a stirred solution of tert-butyl ((7-(4-chlorophenyl)-9-methoxy-2-methyl-3-oxo-3,5-dihydro-2H-benzo[c]pyrido[3,4-e]azepin-5-yl)methyl)carbamate (example 45, 0.15 g, 0.3 mmol) in dioxan (1 mL), dioxin.HCl (5 mL) at 0° C. under nitrogen atmosphere. The mixture was concentrated under vacuum. The crude was washed with diethyl ether twice and dried under vacuum (0.1 g crude). MS (ESI): mass calcd. for CH$_{22}$Cl$_{21}$N$_3$O$_2$, 393.1; m/z found, 394.1[M+H]$^+$.

Step B

To a stirred solution of 5-(aminomethyl)-7-(4-chlorophenyl)-9-methoxy-2-methyl-2H-benzo[c]pyrido[3,4-e]azepin-3(5H)-one hydrochloride (XIII, 0.1 g crude, 0.25 mmol) in DCM (5 mL), triethyl amine (0.052 mL, 0.375 mmol) at 0° C. under nitrogen atmosphere. The mixture was stirred for 15 mins. Then acetyl chloride (0.021 mL, 0.3 mmol) was added at 0° C. The mixture was stirred for 1 h at room temperature. The mixture was quenched with water and extracted with DCM, dried over sodium sulphate, and dried under vacuum (0.006 g). $^1$H NMR (DMSO-d$_6$, 400 MHz): δ (ppm) 8.06 (br.s., 1H), 7.99 (s, 1H), 7.61 (d, J=8.4 Hz, 1H), 7.50 (d, J=8.4 Hz, 2H), 7.43 (d, J=8.8 Hz, 2H), 7.24-7.22 (m, 1H), 6.73 (d, J=2.8 Hz, 1H), 6.4 (s, 1H), 3.9-3.85 (m, 2H), 3.72 (s, 3H), 3.71-3.69 (m, 1H), 3.48 (s, 3H), 1.7 (s, 3H). MS (ESI): mass calcd. for C$_{24}$H$_{22}$ClN$_3$O$_3$, 435.13; m/z found, 436.2[M+H]$^+$.

Biological Methods

BRD4 AlphaLISA (Perkin Elmer)

Compounds were diluted by step-down dilution method (final concentration of DMSO was 1%) and added to the wells of a 384 well opti plate at desired concentrations. 5 nM BDR4-BD1 enzyme (produced in-house) and 12 nM of biotinylated substrate were added to the wells, covered and incubated at room temperature (RT) for 1 h. At the end of 1 h 250 ng of GSH acceptor beads were added to the well and incubated for 1 h at RT; then 500 ng of streptavidin donor beads were added and incubated again for 1 h at RT. Plates were read in a Pherastar reader at 680 nm excitation and 570 nm emission. As detailed above, compounds were tested for both BRD4 enzyme inhibitory activities and $IC_{50}$ were determined. The activities of selected compounds are listed in Table 1

Anticancer Activity: Alamar Blue Assay

The impact of the compounds on cancer cell proliferation was determined using the AML cell line MV4-11 (ATCC) in a 3-day proliferation assay. MV4-11 cells were maintained in RPMI supplemented with 10% FBS at 37° C., 5% $CO_2$. For compound testing, MV4-11 cells were plated in a 96-well black bottom plate at a density of 15,000 cells/well in 100 µL culture media and incubated at 37° C. overnight. Compound dilution series were prepared in DMSO via a 3-fold serial dilution from 100 µM to 0.005 µM. The DMSO dilution series were then diluted with media, with the final compound concentrations added to the wells ranging from 10 µM to 0.0005 µM. After the additions of compounds, the cells were incubated for 72 h and the numbers of viable cells were determined using the Alamar Blue assay (Invitrogen), according the manufacturers suggested protocol. The fluorescent readings from the Alamar Blue assay were normalized to the DMSO treated cells and analyzed using the GraphPad Prism software with sigmoidal curve fitting to obtain $EC_{50}$. The selected compounds activities are listed in Table 1.

TABLE 1

Selected list of compounds with BRD4-BD1 $IC_{50}$ and Anti-cancer activity

| Compound | BRD4_BD1 IC50_µM | MV4-11 EC50_µM |
| --- | --- | --- |
| 1 | 0.024 | ND |
| 2 | 0.01 | 0.001 |
| 8F | 0.012 | 0.024 |
| 11 | 0.061 | 0.175 |
| 14 | 0.003 | 0.002 |
| 18 | 0.122 | ND |
| 19 | 0.176 | ND |
| 23 | 0.001 | 0.005 |
| 25 | 0.0016 | 0.003 |
| 26 | 0.002 | 0.008 |
| 27 | 0.0044 | 0.112 |
| 28 | 0.036 | 0.326 |
| 30 | 0.01 | 0.118 |
| 32 | 0.049 | 0.108 |
| 35 | 0.077 | 0.04 |
| 37 | 0.004 | 0.028 |
| 38 | <0.0005 | 0.013 |
| 39 | 0.004 | 0.008 |

Determination of Biomarker C-Myc and p21 in MV4-11 Cells.

MV4-11 cells were seeded in a 24-well plate at a density of $0.2 \times 10^6$ cells/ml and incubated at 37° C. overnight. The cells were treated with the compounds at the indicated concentrations and time points. The cells were harvested at the indicated time points and protein extraction was performed using the RIPA buffer. For the tumor samples, the protein was extracted by homogenizing a small piece of the tumor in RIPA buffer. 25-50 µg protein was resolved in SDS-PAGE and subjected to Western Blotting. The antibodies against cMYC and p21 were purchased from Cell Signaling. The antibody against β-Actin was purchased from Sigma.

In Vivo Xenograft Model

The effects of the compounds to inhibit the growth of MV4-11 xenograft tumors were evaluated. Briefly, $5 \times 10^6$ cells of MV4-11 cells; diluted 1:1 with matrigel were injected subcutaneously on the upper flanks of female nude mice (Charles Rivers Labs). The total volume injected per animal was 200 µL. The mice were observed for approximately 15-20 days with concomitant tumor volume measurement. The treatment was initiated post-randomization when the average tumor volume was approximately 100 $mm^3$. The compounds were formulated in 0.02% Tween-80, 0.5% Methylcellulose and administered by oral gavage. The tumors were measured by a pair of callipers thrice a week starting at the time of size match, and tumor volumes were calculated according to the formula $V=(L \times W \times H) \times 0.52$ (V:volume, $mm^3$; L:length, mm; W:width, mm; H:height, mm). The tumor volume and body weight were measured for the duration of the experiment, until the mean tumor volume in each group reached an endpoint of >1000 $mm^3$. Compounds of formula I showing greater 50% tumor growth inhibition are considered as active.

Although the subject matter has been described in considerable detail with reference to certain embodiments thereof, other embodiments are possible. As such, the spirit and scope of the invention should not be limited to the description of the embodiments contained herein.

We claim:

1. A method of inhibiting one or more BET family bromodomains in a cell comprising contacting said cell with an effective amount of the compound of the Formula (I)

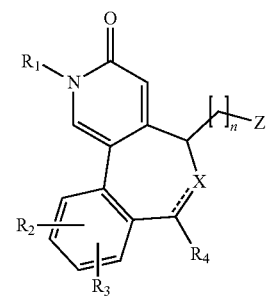

or a tautomeric form, stereoisomer, polymorph, solvate, or pharmaceutically acceptable salts thereof;

wherein

--- is a single bond or a double bond;

X is selected from —O— or —N—;

n is 0-6;

$R_1$ is selected from alkyl or cycloalkyl;

$R_2$ and $R_3$ are independently selected from hydrogen, halogen, hydroxy, nitro, cyano, azido, nitroso, oxo (=O), thioxo (=S), —$SO_2$—, amino, hydrazino, formyl, alkyl, haloalkyl, alkoxy, haloalkoxy, arylalkoxy, cycloalkyl, cycloalkyloxy, aryl, heterocyclyl, heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and Re are independently selected from hydrogen, alkyl, cycloalkyl, aryl, arylalkyl, heterocyclyl, heteroaryl or heteroarylalkyl;

R$_4$ is selected from hydrogen, optionally substituted alkyl, optionally substituted cycloalkyl, optionally substituted cycloalkenyl, optionally substituted cycloalkylalkyl, optionally substituted aryl, optionally substituted arylalkyl, optionally substituted heterocyclyl, optionally substituted heterocyclylalkyl, optionally substituted heteroaryl, optionally substituted heteroarylalkyl or optionally substituted haloalkyl;

Z is selected from hydrogen, —CH$_2$OR$_5$, —COOR$_5$, —CONR$_5$R$_6$, —NHCOOR$_5$, —NHCOR$_5$ or —NHSO$_2$R$_5$; and R$_5$ and R$_6$ are independently selected from hydrogen, hydroxyl, aryl, heteroaryl, cycloalkyl, or alkyl, wherein R$_5$ and R$_6$ are optionally substituted.

2. A method of treating a proliferative disorder or cancer, comprising administering to a subject suffering from the proliferative disorder or cancer a therapeutically effective amount of a compound of the Formula (I)

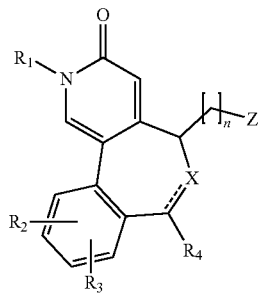

or a tautomeric form, stereoisomer, polymorph, solvate, or pharmaceutically acceptable salts thereof;
wherein
--- is a single bond or a double bond;
X is selected from —O— or —N—;
n is 0-6;
R$_1$ is selected from alkyl or cycloalkyl;
R$_2$ and R$_3$ are independently selected from hydrogen, halogen, hydroxy, nitro, cyano, azido, nitroso, oxo (=O), thioxo (=S), —SO$_2$—, amino, hydrazino, formyl, alkyl, haloalkyl, alkoxy, haloalkoxy, arylalkoxy, cycloalkyl, cycloalkyloxy, aryl, heterocyclyl, heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and Re are independently selected from hydrogen, alkyl, cycloalkyl, aryl, arylalkyl, heterocyclyl, heteroaryl or heteroarylalkyl;

R$_4$ is selected from hydrogen, optionally substituted alkyl, optionally substituted cycloalkyl, optionally substituted cycloalkenyl, optionally substituted cycloalkylalkyl, optionally substituted aryl, optionally substituted arylalkyl, optionally substituted heterocyclyl, optionally substituted heterocyclylalkyl, optionally substituted heteroaryl, optionally substituted heteroarylalkyl or optionally substituted haloalkyl;

Z is selected from hydrogen, —CH$_2$OR$_5$, —COOR$_5$, —CONR$_5$R$_6$, —NHCOOR$_5$, —NHCOR$_5$ or —NHSO$_2$R$_5$; and R$_5$ and R$_6$ are independently selected from hydrogen, hydroxyl, aryl, heteroaryl, cycloalkyl, or alkyl, wherein R$_5$ and R$_6$ are optionally substituted; and wherein the proliferative disorder or cancer is lymphoma, leukemia, breast cancer, lung cancer, ovarian cancer, prostate cancer, brain tumor, and skin cancer.

3. The method of claim 2, wherein the compound is administered in combination with at least one compound selected from cytotoxic agents or non-cytotoxic agents to the subject.

4. The method of claim 2, wherein the compound is administered in combination with at least one other clinically relevant cytotoxic agents or non-cytotoxic agents to the subject.

5. The method of claim 2, wherein the compound is administered in combination with at least one with other clinically relevant immune modulators agents to the subject.

6. The method of claim 2, wherein
--- is a single bond or a double bond;
X is selected from —O— or —N—;
n is 0-1;
R$_1$ is selected from C$_1$-C$_8$ alkyl or C$_3$-C$_8$cycloalkyl;
R$_2$ and R$_3$ are independently selected from hydrogen, fluoro, chloro, bromo, iodo, hydroxy, nitro, cyano, azido, nitroso, oxo (=O), thioxo (=S), —SO$_2$—, amino, hydrazino, formyl, C$_1$-C$_8$alkyl, C$_1$-C$_8$haloalkyl independently substituted with up to three halogen groups selected from fluoro, chloro, bromo, or iodo, C$_1$-C$_8$alkoxy, C$_1$-C$_8$haloalkoxy, C$_5$-C$_{18}$arylalkoxy, C$_3$-C$_8$cycloalkyl, C$_3$-C$_8$cycloalkyloxy, C$_5$-C$_{18}$aryl, C$_2$-C$_{18}$heterocyclyl, C$_2$-C$_{18}$heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogen, C$_1$-C$_8$ alkyl, C$_3$-C$_8$cycloalkyl, C$_5$-C$_{18}$aryl, C$_5$-C$_{18}$arylalkyl, C$_2$-C$_{18}$heterocyclyl, C$_2$-C$_{18}$heteroaryl and C$_2$-C$_{18}$heteroarylalkyl;

R$_4$ is selected from hydrogen, C$_1$-C$_8$alkyl, C$_2$-C$_8$alkynyl, C$_3$-C$_8$cycloalkyl, C$_3$-C$_8$cyloalkenyl, C$_3$-C$_8$cycloalkylalkyl, C$_5$-C$_{18}$aryl, C$_5$-C$_{18}$arylalkyl, C$_2$-C$_{18}$heterocyclyl, C$_2$-C$_{18}$heterocyclylalkyl, C$_2$-C$_{18}$heteroaryl, C$_2$-C$_{18}$heteroarylalkyl or C$_1$-C$_8$haloalkyl, wherein alkyl, cycloalkyl, cycloalkenyl, cycloalkylalkyl, aryl, arylalkyl, heterocyclyl, heterocyclylalkyl, heteroaryl and heteroarylalkyl are independently unsubstituted or substituted with up to three substituents independently selected from halogen, alkyl, alkenyl, alkynyl, alkoxy, acyl, acyloxy, amino, hydroxy, keto, nitro, azido, cyano, amide, sulfonamide and carbamate, wherein the heterocyclyl, heterocylylalkyl, heteroaryl and heteroarylalkyl contains up to three heteroatoms selected from O, N or S;

Z is selected from hydrogen, —CH$_2$OR$_5$, —COOR$_5$, —CONR$_5$R$_6$, —NHCOOR$_5$, —NHCOR$_5$ or —NHSO$_2$R$_5$, wherein R$_5$ and R$_6$ are independently selected from hydrogen, hydroxyl, C$_5$-C$_{18}$aryl, C$_2$-C$_{18}$heteroaryl, C$_3$-C$_8$cycloalkyl or C$_1$-C$_8$alkyl; wherein R$_5$ and R$_6$ are optionally substituted with one or more substituents selected from fluorine, chlorine, bromine, iodine, hydroxy, nitro, cyano, azido, nitroso, oxo (=O), thioxo (=S), —SO$_2$—, amino, hydrazino, formyl, C$_1$-C$_8$alkyl, C$_1$-C$_8$haloalkylalkoxy, C$_1$-C$_8$haloalkoxy, C$_5$-C$_{18}$arylalkoxy, C$_3$-C$_8$cycloalkyl, C$_3$-C$_8$cycloalkyloxy, C$_5$-C$_{18}$aryl, C$_2$-C$_{18}$heterocyclyl, C$_2$-C$_{18}$heteroaryl, alkylamino, —COOR$^a$, —C(O)R$^b$, —C(S)R$_a$, —C(O)NR$^a$R$^b$, —C(S)NR$^a$R$^b$, —NR$^a$C(O)NR$^b$R$^c$, NR$^a$C(S)NR$^b$R$^c$, —N(R$^a$)SOR$^b$, —N(R$^a$)SO$_2$R$^b$, —NR$^a$C(O)OR$^b$, —NR$^a$R$^b$, —NR$^a$C(O)R$^b$—, NR$^a$C(S)R$^b$—, —SONR$^a$R$^b$—, —SO$_2$NR$^a$R$^b$—, —OR$^a$, —OR$^a$C(O)OR$^b$—, —OC(O)NR$^a$R$^b$, OC(O)R$^a$, —OC(O)NR$^a$R$^b$—, —R$^a$NR$^b$R$^c$, —R$^a$OR$^b$—, —SR$^a$, —SOR$^a$, or —SO$_2$R$^a$, wherein R$^a$, R$^b$ and R$^c$ are independently selected from hydrogen, or optionally substituted groups selected from alkyl, cycloalkyl, aryl, arylalkyl, heterocyclyl, heteroaryl or hetroarylalkyl.

7. The method of claim 6, wherein
--- is a single bond or a double bond;
X is selected from —O— or —N—;
n is 0-1;
R$_1$ is selected from hydrogen, methyl, ethyl, n-propyl, ispopropyl, n-butyl, isobutyl, t-butyl, pentyl, hexyl, heptyl, octyl, cyclopropyl, cyclobutyl, cyclopentyl or cyclohexyl;
R$_2$ and R$_3$ are independently selected from hydrogen, fluorine, chlorine, bromine, iodine, hydroxy, nitro, cyano, azido, nitroso, oxo (=O), thioxo (=S), —SO$_2$—, amino, hydrazino, formyl, alkyl, haloalkyl, alkoxy, haloalkoxy, arylalkoxy, cycloalkyl, cycloalkyloxy, aryl, heterocyclyl, heteroaryl, alkylamino, —COOR$_a$, —C(O)R$_b$, —C(S)R$_a$, —C(O)NR$_a$R$_b$, —C(S)NR$_a$R$_b$, —NR$_a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and Re are independently selected from hydrogen, alkyl, cycloalkyl, aryl, arylalkyl, heterocyclyl, heteroaryl and hetroarylalkyl;
R$_4$ is selected from hydrogen, substituted or unsubstituted aryl selected from the group consisting of phenyl, naphthyl, biphenyl and indanyl, heteroaryl selected from the group consisting of pyridinyl, pyridazinyl, pyrimidyl, triazinyl, pyrrolyl, indolyl, pyrazolyl, imidazolyl, pyrazinyl, pyrimidinyl, tetrazolyl, furyl, thienyl, thiazolyl, isoxazolyl, oxazolyl and quinolinyl, cycloalkyl selected from the group consisting of cyclopropyl, cyclobutyl, cyclopentyl, cyclohexyl and cyclooctyl, alkyl selected from the group consisting of methyl, ethyl, n-propyl, isopropyl, butyl, isobutyl, t-butyl, pentyl, hexyl, heptyl and octyl, haloalkyl selected from the group consisting of trichloromethyl, trifluoromethyl, difluoromethyl, trifluoroethyl, trichloroethyl, monofluoromethyl and monochloromethyl;
Z is selected from hydrogen, —CH$_2$OR$_5$, —COOR$_5$, —CONR$_5$R$_6$, —NHCOOR$_5$, —NHCOR$_5$ or —NHSO$_2$R$_5$, wherein R$_5$ and R$_6$ are selected from hydrogen, substituted or unsubstituted aryl selected from the group consisting of phenyl, naphthyl, biphenyl and indanyl, heteroaryl selected from the group consisting of pyridinyl, pyridazinyl, pyrimidyl, triazinyl, pyrrolyl, indolyl, pyrazolyl, imidazolyl, pyrazinyl, pyrimidinyl, tetrazolyl, furyl, thienyl, thiazolyl, isoxazolyl, oxazolyl and quinolinyl, cycloalkyl selected from the group consisting of cyclopropyl, cyclobutyl, cyclopentyl, cyclohexyl and cyclooctyl, alkyl group selected from the group consisting of methyl, ethyl, n-propyl, isopropyl, butyl, isobutyl, t-butyl, pentyl, hexyl, heptyl and octyl;
R$_5$ and R$_6$ are optionally substituted with one or more selected from halogen, hydroxy, nitro, cyano, azido, nitroso, oxo (=O), thioxo (=S), —SO$_2$—, amino, hydrazino, formyl, alkyl, haloalkyl, alkoxy, haloalkoxy, arylalkoxy, cycloalkyl, cycloalkyloxy, aryl, heterocyclyl, heteroaryl, alkylamino, —COOR$^a$, —C(O)R$^b$, —C(S)R$^a$, —C(O)NR$^a$R$^b$, —C(S)NR$^a$R$^b$, —NR$^a$C(O)NR$^b$R$^c$, NR$^a$C(S)NR$^b$R$^c$, —N(R$^a$)SOR$^b$, —N(R$^a$)SO$_2$R$^b$, —NR$^a$C(O)OR$^b$, —NR$^a$R$^b$, —NR$^a$C(O)R$^b$—, NR$^a$C(S)R$^b$—, —SONR$^a$R$^b$—, —SO$_2$NR$^a$R$^b$—, —OR$^a$, —OR$^a$C(O)OR$^b$—, —OC(O)NR$^a$R$^b$, OC(O)R$^a$, —OC(O)NR$^a$R$^b$—, —R$^a$NR$^b$R$^c$, —R$^a$OR$^b$—, —SR$^a$, —SOR$^a$ or —SO$_2$R$^a$, wherein R$^a$, R$^b$ and R$^c$ are independently selected from hydrogen or optionally substituted groups selected from alkyl, cycloalkyl, aryl, arylalkyl, heterocyclyl, heteroaryl or hetroarylalkyl.

8. The method of claim 2, wherein
--- is a single bond;
X is —O—;
n is 0-1;
R$_1$ is selected from C$_1$-C$_8$ alkyl or C$_3$-C$_8$cycloalkyl;
R$_2$ is hydrogen;
R$_3$ is selected from halogen, C$_1$-C$_8$ alkyl, C$_1$-C$_8$haloalkyl substituted up to 3 halogen groups selected from fluoro, chloro, bromo, or iodo, C$_1$-C$_8$alkoxy, C$_1$-C$_8$haloalkoxy, C$_5$-C$_{18}$arylalkoxy, C$_3$-C$_8$cycloalkyl, C$_3$-C$_8$cycloalkyloxy, C$_5$-C$_{18}$ aryl, C$_2$-C$_{18}$heterocyclyl or C$_2$-C$_{18}$heteroaryl;
R$_4$ is selected from hydrogen, C$_1$-C$_8$ alkyl, C$_3$-C$_8$cycloalkyl, C$_3$-C$_8$cyloalkenyl, C$_3$-C$_8$cycloalkylalkyl, C$_5$-C$_{18}$ aryl, C$_5$-C$_{18}$arylalkyl, C$_2$-C$_{18}$heterocyclyl, C$_2$-C$_{18}$heterocyclylalkyl, C$_2$-C$_{18}$heteroaryl, C$_2$-C$_{18}$ heteroarylalkyl or C$_1$-C$_8$haloalkyl, wherein alkyl, cycloalkyl, cycloalkenyl, cycloalkylalkyl, aryl, arylalkyl, heterocyclyl, heterocyclylalkyl, heteroaryl and heteroarylalkyl are independently unsubstituted or substituted with up to three substituents independently selected from halogen, alkyl, alkenyl, alkynyl, alkoxy, acyl, acyloxy, amino, hydroxy, keto, nitro, azido, cyano, amide, sulfonamide and carbamate;
wherein the heterocyclyl, heterocyclylalkyl, heteroaryl and heteroarylalkyl contains up to three heteroatoms selected from O, N or S;
Z is selected from the group consisting of hydrogen, —CH$_2$OR$_5$, —COOR$_5$, —CONR$_5$R$_6$, —NHCOOR$_5$, —NHCOR$_5$ or —NHSO$_2$R$_5$; wherein R$_5$ and R$_6$ are independently selected from hydrogen, hydroxyl, C$_5$-C$_{18}$ aryl, C$_2$-C$_{18}$heteroaryl, C$_3$-C$_8$cycloalkyl or C$_1$-C$_8$ alkyl; wherein R$_5$ and R$_6$ are optionally substituted with one or more substituents selected fluorine, chlorine, bromine, iodine; hydroxy, nitro, cyano, azido, nitroso, oxo (=O), thioxo (=S), —SO$_2$—, amino, hydrazino, formyl, C$_1$-C$_8$ alkyl, C$_1$-C$_8$haloalkylalkoxy, $C_1$-$C_8$haloalkoxy, $C_5$-$C_{18}$arylalkoxy; $C_3$-$C_8$cycloalkyl, $C_3$-$C_8$cycloalkyloxy, $C_6$-$C_{18}$ aryl, $C_2$-$C_{18}$heterocyclyl, or $C_2$-$C_{18}$heteroaryl.

9. The method of claim 6, wherein
--- is a single bond or a double bond;
X is selected from —O— or —N—;
n is 0-1;
$R_1$ is selected from $C_1$-$C_2$ alkyl;
$R_2$ and $R_3$ are independently selected from hydrogen, halogen, $C_1$-$C_8$ haloalkyl, $C_1$-$C_8$ alkoxy, and $C_1$-$C_8$ haloalkoxy;
$R_4$ is selected from hydrogen, $C_1$-$C_8$alkyl, $C_3$-$C_8$cycloalkyl, $C_3$-$C_8$cycloalkylalkyl, $C_5$-$C_{18}$aryl, $C_2$-$C_{18}$heteroaryl, or $C_1$-$C_8$haloalkyl, wherein alkyl, cycloalkyl, cycloalkylalkyl, aryl, heteroaryl and heteroarylalkyl are independently unsubstituted or substituted with up to three substituents independently selected from halogen, alkyl, and cyano, wherein the heteroaryl contains up to three heteroatoms selected from O or N;
Z is selected from hydrogen, —$CH_2OR_5$, —$COOR_5$, —$CONR_5R_6$, —$NHCOOR_5$, — or $NHCOR_5$, wherein $R_5$ and $R_6$ are independently selected from hydrogen, $C_5$-$C_{18}$aryl, or $C_1$-$C_8$alkyl; wherein
$R_5$ and $R_6$ are optionally substituted with one or more substituents selected from fluorine, chlorine, bromine, iodine, hydroxy, and cyano.

10. The method of claim 6, wherein
$R_1$ is selected from methyl and isopropyl;
$R_2$ is hydrogen;
$R_3$ is selected from, halogen, $C_1$-$C_2$ haloalkyl, $C_1$-$C_2$ alkoxy, and $C_1$-$C_2$ haloalkoxy; wherein haloalkyl and haloalkoxy are substituted with one or more substituents selected from fluorine and chlorine;
$R_4$ is selected from hydrogen, $C_1$-$C_2$alkyl, $C_3$-$C_5$cycloalkyl, $C_3$-$C_5$cycloalkylalkyl, $C_5$-$C_6$ aryl, $C_5$-$C_6$heteroaryl, or $C_1$-$C_2$haloalkyl, wherein alkyl, cycloalkylalkyl, aryl, heteroaryl and heteroarylalkyl are independently unsubstituted or substituted with up to three substituents independently selected from halogen, alkyl, and cyano, wherein the heteroaryl contains one heteroatom as N;
Z is selected from hydrogen, —$CH_2OR_5$, —$COOR_5$, —$CONR_5R_6$, —$NHCOOR_5$, — or $NHCOR_5$, wherein $R_5$ and $R_6$ are independently selected from hydrogen, $C_6$ aryl, or $C_1$-$C_3$alkyl; wherein $C_6$ aryl is substituted with hydroxyl.

11. The method of claim 8, wherein
--- is a single bond;
X is —O—;
n is 0-1;
$R_1$ is selected from $C_1$-$C_8$ alkyl or $C_3$-$C_8$cycloalkyl;
$R_2$ is hydrogen;
$R_3$ is selected from halogen, $C_1$-$C_8$ alkyl, $C_1$-$C_8$haloalkyl substituted up to 3 halogen groups selected from fluoro, chloro, bromo, or iodo, $C_1$-$C_8$alkoxy, $C_1$-$C_8$haloalkoxy, $C_5$-$C_{18}$arylalkoxy, $C_3$-$C_8$cycloalkyl, $C_3$-$C_8$cycloalkyloxy, $C_5$-$C_{18}$ aryl, $C_2$-$C_{18}$heterocyclyl, or $C_2$-$C_{18}$heteroaryl;
$R_4$ is selected from hydrogen, $C_1$-$C_8$ alkyl, $C_3$-$C_8$cycloalkyl, $C_5$-$C_{18}$ aryl, $C_5$-$C_{18}$arylalkyl, $C_2$-$C_{18}$heterocyclyl, $C_2$-$C_{18}$heteroaryl, $C_2$-$C_{18}$heteroarylalkyl or $C_1$-$C_8$haloalkyl, wherein alkyl, cycloalkyl, aryl, arylalkyl, heterocyclyl, heteroaryl and heteroarylalkyl are independently unsubstituted or substituted with up to three substituents independently selected from halogen, alkyl, alkenyl, alkynyl, alkoxy, acyl, acyloxy, amino, hydroxy, keto, nitro, azido, cyano, amide, sulfonamide, and carbamate;
wherein the heterocyclyl, heteroaryl and heteroarylalkyl contains up to three heteroatoms selected from O, N or S;
Z is selected from the group consisting of hydrogen, —$CH_2OR_5$, —$COOR_5$, —$CONR_5R_6$, —$NHCOOR_5$, —$NHCOR_5$ or —$NHSO_2R_5$;
$R_5$ and $R_6$ are independently selected from hydrogen, hydroxyl, $C_5$-$C_{18}$ aryl, $C_2$-$C_{18}$heteroaryl, $C_3$-$C_8$cycloalkyl or $C_1$-$C_8$ alkyl; wherein $R_5$ and $R_6$ are optionally substituted with one or more substituents selected from fluorine, chlorine, bromine, iodine; hydroxy, nitro, cyano, azido, nitroso, oxo (═O), thioxo (═S), —$SO_2$—, amino, hydrazino, formyl, $C_1$-$C_8$ alkyl, $C_1$-$C_8$haloalkylalkoxy, $C_1$-$C_8$haloalkoxy, $C_5$-$C_{18}$arylalkoxy, $C_3$-$C_8$cycloalkyl, $C_3$-$C_8$cycloalkyloxy, $C_6$-$C_{18}$ aryl, $C_2$-$C_{18}$heterocyclyl, or $C_2$-$C_{18}$heteroaryl.

12. The method of claim 2, wherein
--- is a double bond;
X is —N—;
n is 0-1;
$R_1$ is selected from $C_1$-$C_8$ alkyl or $C_3$-$C_8$ cycloalkyl;
$R_2$ is hydrogen;
$R_3$ is selected from halogen, $C_1$-$C_8$ alkyl, $C_1$-$C_8$haloalkyl substituted up to three halogens selected from fluoro, chloro, bromo, or iodo, $C_1$-$C_8$alkoxy, $C_1$-$C_8$haloalkoxy, $C_5$-$C_{18}$arylalkoxy, $C_3$-$C_8$cycloalkyl, $C_3$-$C_8$cycloalkyloxy, $C_5$-$C_{18}$ aryl, $C_2$-$C_{18}$heterocyclyl or $C_2$-$C_{18}$heteroaryl;
$R_4$ is selected from hydrogen, $C_1$-$C_8$ alkyl, $C_3$-$C_8$cycloalkyl, $C_3$-$C_8$cyloalkenyl, $C_3$-$C_8$ cycloalkylalkyl, $C_5$-$C_{18}$ aryl, $C_5$-$C_{18}$arylalkyl, $C_2$-$C_{18}$heterocyclyl, $C_2$-$C_{18}$heterocyclylalkyl, $C_2$-$C_{18}$heteroaryl, $C_2$-$C_{18}$heteroarylalkyl, or $C_1$-$C_8$haloalkyl; wherein alkyl, cycloalkyl, cycloalkenyl, cycloalkylalkyl, aryl, arylalkyl, heterocyclyl, heterocyclylalkyl, heteroaryl, and heteroarylalkyl are independently unsubstituted or substituted with up to three substituents independently selected from halogen, alkyl, alkenyl, alkynyl, alkoxy, acyl, acyloxy, amino, hydroxy, keto, nitro, azido, cyano, amide, sulfonamide and carbamate; wherein the heterocyclyl, heterocyclylalkyl, heteroaryl and heteroarylalkyl contains up to three heteroatoms selected from O, N or S;
Z is selected from the group consisting of hydrogen, —$CH_2OR_5$, —$COOR_5$, —$CONR_5R_6$, —$NHCOOR_5$, —$NHCOR_5$, or —$NHSO_2R_5$;
$R_5$ and $R_6$ are independently selected from hydrogen, hydroxyl, $C_5$-$C_{18}$ aryl, $C_2$-$C_{18}$heteroaryl, $C_3$-$C_8$cycloalkyl, or $C_1$-$C_8$ alkyl; wherein
$R_5$ and $R_6$ are optionally substituted with, the one or more substituents are selected from halogen; hydroxy, nitro, cyano, azido, nitroso, oxo (═O), thioxo (═S), —$SO_2$—, amino, hydrazino, formyl, $C_1$-$C_8$ alkyl, $C_1$-$C_8$ haloalkylalkoxy, $C_1$-$C_8$ haloalkoxy, $C_5$-$C_{18}$ arylalkoxy, $C_3$-$C_8$ cycloalkyl, $C_3$-$C_8$ cycloalkyloxy, $C_6$-$C_{18}$ aryl, $C_2$-$C_{18}$ heterocyclyl, or $C_2$-$C_{18}$ heteroaryl.

13. The method of claim 10, wherein
--- is a double bond;
X is —N—;
n is 0-1;
$R_1$ is selected from $C_1$-$C_8$ alkyl or $C_3$-$C_8$ cycloalkyl;
$R_2$ is hydrogen;

R₃ is selected from halogen, C₁-C₈ alkyl, C₁-C₈ haloalkyl substituted up to 3 halogen groups selected from fluoro, chloro, bromo, iodo, C₁-C₈ alkoxy, C₁-C₈ haloalkoxy, C₅-C₁₈ arylalkoxy, C₃-C₈ cycloalkyl, C₃-C₈ cycloalkyloxy, C₆-C₁₈ aryl, C₂-C₁₈ heterocyclyl, or C₅-C₁₈ heteroaryl; R₄ is selected from hydrogen, C₁-C₈ alkyl, C₃-C₈ cycloalkyl, C₅-C₁₈ aryl, C₅-C₁₈ arylalkyl, C₂-C₁₈ heterocyclyl, C₂-C₁₈ heteroaryl, C₂-C₁₈ heteroarylalkyl, or C₁-C₈ haloalkyl;

wherein alkyl, cycloalkyl, aryl, arylalkyl, heterocyclyl, heteroaryl and heteroarylalkyl are independently unsubstituted or substituted with up to three substituents independently selected from halogen, alkyl, alkenyl, alkynyl, alkoxy, acyl, acyloxy, amino, hydroxy, keto, nitro, azido, cyano;

wherein the heterocyclyl, heteroaryl, and heteroarylalkyl contains up to three heteroatoms selected from O, N or S;

Z is selected from the group consisting of hydrogen, —CH₂OR₅, —COOR₅, —CONR₅R₆, —NHCOOR₅, or —NHCOR₅; wherein R₅ and R₆ are independently selected from hydrogen, hydroxyl, C₆-C₁₈ aryl, C₂-C₁₈ heteroaryl, C₃-C₈ cycloalkyl or C₁-C₈ alkyl wherein;

R₅ and R₆ are optionally substituted, with one or more substituents selected from fluorine, chlorine, bromine, iodine; hydroxy, nitro, cyano, azido, nitroso, oxo (=O), thioxo (=S), —SO₂—, amino, hydrazino, formyl, C₁-C₈ alkyl, C₁-C₈ haloalkylalkoxy, C₁-C₈ haloalkoxy, C₅-C₁₈ arylalkoxy, C₃-C₈ cycloalkyl, C₃-C₈ cycloalkyloxy, C₅-C₁₈ aryl, C₂-C₁₈ heterocyclyl, or C₂-C₁₈ heteroaryl.

14. The method of claim 2, the compound is a compound of the Formula (Ia),

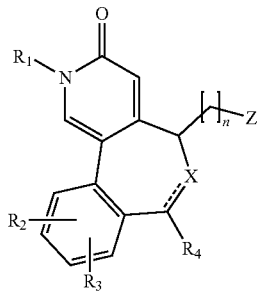

wherein
X is selected from —O— or —N—;
n is 0-1;
R₁ is selected from C₁-C₈ alkyl or C₃-C₈ cycloalkyl;
R₂ and R₃ are independently selected from hydrogen, fluoro, chloro, bromo, iodo, hydroxy, nitro, cyano, azido, nitroso, oxo (=O), thioxo (=S), —SO₂—, amino, hydrazino, formyl, C₁-C₈ alkyl, C₁-C₈ haloalkyl independently substituted with up to 3 halogen groups selected from fluoro, chloro, bromo, or iodo, C₁-C₈alkoxy, C₁-C₈haloalkoxy, C₅-C₁₈arylalkoxy, C₃-C₈cycloalkyl, C₃-C₈cycloalkyloxy, C₅-C₁₈ aryl, C₂-C₁₈heterocyclyl, C₂-C₁₈heteroaryl, alkylamino, —COOR_a, —C(O)R_b, —C(S)R_a, —C(O)NR_aR_b, —C(S)NR_aR_b, —NR_aC(O)NR_bR_c, NR_aC(S)NR_bR_c, —N(R_a)SOR_b, —N(R_a)SO₂R_b, —NR_aC(O)OR_b, —NR_aR_b, —NR_aC(O)R_b—, NR_aC(S)R_b—, —SONR_aR_b—, —SO₂NR_aR_b—, —OR_a, —OR_aC(O)OR_b—, —OC(O)NR_aR_b, OC(O)R_a, —OC(O)NR_aR_b—, —R_aNR_bR_c, —R_aOR_b—, —SR_a, —SOR_a or —SO₂R_a, wherein R_a, R_b and R_c are independently selected from hydrogen, C₁-C₈ alkyl, C₃-C₈cycloalkyl, C₅-C₁₈aryl, C₅-C₁₈arylalkyl, C₂-C₁₈heterocyclyl, C₂-C₁₈heteroaryl, and C₂-C₁₈hetroarylalkyl, R₄ is selected from hydrogen, C₁-C₈ alkyl, C₃-C₈ cycloalkyl, C₆-C₁₈aryl or C₂-C₁₈heteroaryl; wherein alkyl, cycloalkyl, aryl, and heteroaryl are independently unsubstituted or substituted with up to three substituents independently selected from halogen, alkyl, alkenyl, alkynyl, alkoxy, acyl, acyloxy, amino, hydroxy, keto, nitro, azido, cyano;

wherein the heteroaryl contains up to three heteroatoms selected from O, N or S;

Z is selected from —CH₂OR₅, —COOR₅, —CONR₅R₆, or —CONHR₇;

R₅ and R₆ are independently selected from hydrogen, hydroxyl, C₅-C₁₈ aryl, C₂-C₁₈heteroaryl, C₃-C₈cycloalkyl or C₁-C₈ alkyl; wherein R₅ and R₆ are optionally substituted, with one or more substituents selected from fluorine, chlorine, bromine, iodine; hydroxy, nitro, cyano, azido, nitroso, oxo (=O), thioxo (=S), —SO₂—, amino, hydrazino, formyl, C₁-C₈ alkyl, C₁-C₈ haloalkylalkoxy, C₁-C₈ haloalkoxy; C₅-C₁₈ arylalkoxy; C₃-C₈ cycloalkyl, C₃-C₈ cycloalkyloxy, C₅-C₁₈ aryl, C₂-C₁₈ heterocyclyl, C₂-C₁₈ heteroaryl, alkylamino, —COOR^a, —C(O)R^b, —C(S)R^a, —C(O)NR^aR^b, —C(S)NR^aR^b, —NR^aC(O)NR^bR^c, NR^aC(S)NR^bR^c, —N(R^a)SOR^b, —N(R^a)SO₂R^b, —NR^aC(O)OR^b, —NR^aR^b, —NR^aC(O)R^b—, NR^aC(S)R^b—, —SONR^aR^b—, —SO₂NR^aR^b—, —OR^a, —OR^aC(O)OR^b—, —OC(O)NR^aR^b, OC(O)R^a, —OC(O)NR^aR^b—, —R^aNR^bR^c, —R^aOR^b—, —SR^a, —SOR^a or —SO₂R^a, wherein R^a, R^b and R^c are independently selected from hydrogen or optionally substituted groups selected from alkyl, cycloalkyl, aryl, arylalkyl, heterocyclyl, heteroaryl or hetroarylalkyl, R₇ represents —OR₈, ortho substituted aniline, amino aryl and amino heteroaryl, which may be further substituted, wherein R₈ is selected from hydrogen or optionally substituted groups selected from alkyl, aryl, heterocyclyl, and —COR₉, wherein R₉ is selected from alkyl, aryl, heteroaryl, cycloalkyl or heterocyclyl.

15. The method of claim 2, wherein the compound is selected from a group consisting of:
±Ethyl 2-(-7-(4-chlorophenyl)-9-methoxy-2-methyl-3-oxo-2,3,5,7-tetrahydrobenzo[5,6]oxepino[4,3-c]pyridin-5-yl)acetate,
Ethyl 2-((5S,7R)-(4-chlorophenyl)-9-methoxy-2-methyl-3-oxo-2,3,5,7-tetrahydrobenzo[5,6]oxepino[4,3-c]pyridin-5-yl)acetate,
Ethyl 2-((5S,7S)-(4-chlorophenyl)-9-methoxy-2-methyl-3-oxo-2,3,5,7-tetrahydrobenzo[5,6]oxepino[4,3-c]pyridin-5-yl)acetate,
Ethyl 2-((5R,7S)-(4-chlorophenyl)-9-methoxy-2-methyl-3-oxo-2,3,5,7-tetrahydrobenzo[5,6]oxepino[4,3-c]pyridin-5-yl)acetate,
Ethyl 2-((5R,7R)-(4-chlorophenyl)-9-methoxy-2-methyl-3-oxo-2,3,5,7-tetrahydrobenzo[5,6]oxepino[4,3-c]pyridin-5-yl)acetate,
±Ethyl 2-(7-cyclohexyl-9-methoxy-2-methyl-3-oxo-2,3,5,7-tetrahydrobenzo[5,6]oxepino[4,3-c]pyridin-5-yl)acetate,
±Ethyl 2-(7-(cyclopropylmethyl)-9-methoxy-2-methyl-3-oxo-2,3,5,7-tetrahydrobenzo[5,6]oxepino[4,3-c]pyridin-5-yl)acetate, ±Ethyl 2-(9-methoxy-2-methyl-7-(5-methylpyridin-2-yl)-3-oxo-2,3,5,7-tetrahydrobenzo[5,6]oxepino[4,3-c]pyridin-5-yl)acetate, ±Ethyl 2-(7-(4-chlorophenyl)-9-fluoro-2-methyl-3-oxo-2,3,5,7-tetrahydrobenzo[5,6]oxepino[4,3-c]pyridin-5-yl)acetate, ±Ethyl 2-(7-(4-chlorophenyl)-2-methyl-3-oxo-9-(trifluoromethyl)-2,3,5,7-tetrahydrobenzo[5,6]oxepino[4,3-c]pyridin-5-yl)acetate, ±7-(4-chlorophenyl)-5-(2-hydroxyethyl)-9-methoxy-2-methyl-5,7-dihydrobenzo[5,6]oxepino[4,3-c]pyridin-3(2H)-one, ±2-(-7-(4-chlorophenyl)-9-methoxy-2-methyl-3-oxo-2,3,5,7-tetrahydrobenzo[5,6]oxepino[4,3-c]pyridin-5-yl)-N-ethylacetamide, ±2-((5S,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide, ±2-((5S,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide, 2-((5S,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide, 2-((5S,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide, 2-((5R,7S)-7-(4-chlorophenyl)-9-methoxy-2-methyl-3-oxo-2,3,5,7-tetrahydrobenzo[5,6]oxepino[4,3-c]pyridin-5-yl)-N-ethylacetamide, 2-((5R,7R)-7-(4-chlorophenyl)-9-methoxy-2-methyl-3-oxo-2,3,5,7-tetrahydrobenzo[5,6]oxepino[4,3-c]pyridin-5-yl)-N-ethylacetamide, ±2-(7-cyclohexyl-9-methoxy-2-methyl-3-oxo-2,3,5,7-tetrahydrobenzo[5,6]oxepino[4,3-c]pyridin-5-yl)-N-ethylacetamide, ±2-((5S,7R)-7-cyclohexyl-9-methoxy-2-methyl-3-oxo-2,3,5,7-tetrahydrobenzo[5,6]oxepino[4,3-c]pyridin-5-yl)-N-ethylacetamide, ±2-((5S,7S)-7-cyclohexyl-9-methoxy-2-methyl-3-oxo-2,3,5,7-tetrahydrobenzo[5,6]oxepino[4,3-c]pyridin-5-yl)-N-ethylacetamide, ±2-(7-(cyclopropylmethyl)-9-methoxy-2-methyl-3-oxo-2,3,5,7-tetrahydrobenzo[5,6]oxepino[4,3-c]pyridin-5-yl)-N-ethylacetamide, ±2-((5S,7R)-7-(cyclopropylmethyl)-9-methoxy-2-methyl-3-oxo-2,3,5,7-tetrahydrobenzo[5,6]oxepino[4,3-c]pyridin-5-yl)-N-ethylacetamide, ±2-((5S,7S)-7-(cyclopropylmethyl)-9-methoxy-2-methyl-3-oxo-2,3,5,7-tetrahydrobenzo[5,6]oxepino[4,3-c]pyridin-5-yl)-N-ethylacetamide, ±2-(9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide, ±2-((5S,7S)-9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide, ±2-((5S,7R)-9-methoxy-2-methyl-7-(5-methylpyridin-2-yl)-3-oxo-2,3,5,7-tetrahydrobenzo[5,6]oxepino[4,3-c]pyridin-5-yl)-N-ethylacetamide, ±2-(7-(4-chlorophenyl)-9-fluoro-2-methyl-3-oxo-2,3,5,7-tetrahydrobenzo[5,6]oxepino[4,3-c]pyridin-5-yl)-N-ethylacetamide, ±-2-((5S,7R)-7-(4-chlorophenyl)-9-fluoro-2-methyl-3-oxo-2,3,5,7-tetrahydrobenzo[5,6]oxepino[4,3-c]pyridin-5-yl)-N-ethylacetamide ±-2-((5S,7S)-7-(4-chlorophenyl)-9-fluoro-2-methyl-3-oxo-2,3,5,7-tetrahydrobenzo[5,6]oxepino[4,3-c]pyridin-5-yl)-N-ethylacetamide ±2-(7-(4-chlorophenyl)-2-methyl-3-oxo-9-(trifluoromethyl)-2,3,5,7-tetrahydrobenzo[5,6]oxepino[4,3-c]pyridin-5-yl)-N-ethylacetamide, ±2-((5S,7R)-2-methyl-3-oxo-7-phenyl-9-(trifluoromethyl)-2,3,5,7-tetrahydrobenzo[5,6]oxepino[4,3-c]pyridin-5-yl)-N-ethylacetamide, ±2-((5S,7S)-2-methyl-3-oxo-7-phenyl-9-(trifluoromethyl)-2,3,5,7-tetrahydrobenzo[5,6]oxepino[4,3-c]pyridin-5-yl)-N-ethylacetamide, ±Ethyl 2-(7-(4-chlorophenyl)-9-methoxy-2-methyl-3-oxo-3,5-dihydro-2H-benzo[c]pyrido[3,4-e]azepin-5-yl)acetate, ±Ethyl 2-(7-cyclohexyl-9-methoxy-2-methyl-3-oxo-3,5-dihydro-2H-benzo[c]pyrido[3,4-e]azepin-5-yl)acetate, ±Ethyl 2-(9-methoxy-2-methyl-3-oxo-7-(pyridin-2-yl)-3,5-dihydro-2H-benzo[c]pyrido[3,4-e]azepin-5-yl)acetate, ±Ethyl 2-(7-(cyclopropylmethyl)-9-methoxy-2-methyl-3-oxo-3,5-dihydro-2H-benzo[c]pyrido[3,4-e]azepin-5-yl)acetate, ±Ethyl 2-(9-methoxy-2-methyl-3-oxo-7-(trifluoromethyl)-3,5-dihydro-2H-benzo[c]pyrido[3,4-e]azepin-5-yl)acetate, ±Ethyl 2-(9-methoxy-2,7-dimethyl-3-oxo-3,5-dihydro-2H-benzo[c]pyrido[3,4-e]azepin-5-yl)acetate, ±Ethyl 2-(9-methoxy-2-methyl-7-(5-methylpyridin-2-yl)-3-oxo-3,5-dihydro-2H-benzo[c]pyrido[3,4-e]azepin-5-yl)acetate, ±Ethyl 2-(7-(4-chlorophenyl)-2-isopropyl-9-methoxy-3-oxo-3,5-dihydro-2H-benzo[c]pyrido[3,4-e]azepin-5-yl)acetate, ±Ethyl 2-(7-(4-chlorophenyl)-9-fluoro-2-methyl-3-oxo-3,5-dihydro-2H-benzo[c]pyrido[3,4-e]azepin-5-yl)acetate, ±Ethyl 2-(7-(2,6-difluorophenyl)-9-methoxy-2-methyl-3-oxo-3,5-dihydro-2H-benzo[c]pyrido[3,4-e]azepin-5-yl)acetate, ±Ethyl 2-(7-(4-chloro-2-methylphenyl)-9-methoxy-2-methyl-3-oxo-3,5-dihydro-2H-benzo[c]pyrido[3,4-e]azepin-5-yl)acetate, ±2-(7-(4-chlorophenyl)-9-methoxy-2-methyl-3-oxo-3,5-dihydro-2H-benzo[c]pyrido[3,4-e]azepin-5-yl)-N-ethylacetamide, (S)-2-(7-(4-chlorophenyl)-9-methoxy-2-methyl-3-oxo-3,5-dihydro-2H-benzo[c]pyrido[3,4-e]azepin-5-yl)-N-ethylacetamide, (R)-2-(7-(4-chlorophenyl)-9-methoxy-2-methyl-3-oxo-3,5-dihydro-2H-benzo[c]pyrido[3,4-e]azepin-5-yl)-N-ethylacetamide, ±2-(7-cyclohexyl-9-methoxy-2-methyl-3-oxo-3,5-dihydro-2H-benzo[c]pyrido[3,4-e]azepin-5-yl)-N-ethylacetamide, (S)-2-(7-cyclohexyl-9-methoxy-2-methyl-3-oxo-3,5-dihydro-2H-benzo[c]pyrido[3,4-e]azepin-5-yl)-N-ethylacetamide, (R)-2-(7-cyclohexyl-9-methoxy-2-methyl-3-oxo-3,5-dihydro-2H-benzo[c]pyrido[3,4-e]azepin-5-yl)-N-ethylacetamide, ±2-(9-methoxy-2-methyl-3-oxo-7-(pyridin-2-yl)-3,5-dihydro-2H-benzo[c]pyrido[3,4-e]azepin-5-yl)-N-ethylacetamide, (S)-2-(9-methoxy-2-methyl-3-oxo-7-(pyridin-2-yl)-3,5-dihydro-2H-benzo[c]pyrido[3,4-e]azepin-5-yl)-N-ethylacetamide, (R)-2-(9-methoxy-2-methyl-3-oxo-7-(pyridin-2-yl)-3,5-dihydro-2H-benzo[c]pyrido[3,4-e]azepin-5-yl)-N-ethylacetamide, ±2-(7-(4-chlorophenyl)-9-methoxy-2-methyl-3-oxo-3,5-dihydro-2H-benzo[c]pyrido[3,4-e]azepin-5-yl)acetamide, ±2-(7-(4-chlorophenyl)-9-hydroxy-2-methyl-3-oxo-3,5-dihydro-2H-benzo[c]pyrido[3,4-e]azepin-5-yl)-N-ethylacetamide, ±2-(7-(cyclopropylmethyl)-9-methoxy-2-methyl-3-oxo-3,5-dihydro-2H-benzo[c]pyrido[3,4-e]azepin-5-yl)-N-ethylacetamide, (S)-2-(7-(cyclopropylmethyl)-9-methoxy-2-methyl-3-oxo-3,5-dihydro-2H-benzo[c]pyrido[3,4-e]azepin-5-yl)-N-ethylacetamide, (R)-2-(7-(cyclopropylmethyl)-9-methoxy-2-methyl-3-oxo-3,5-dihydro-2H-benzo[c]pyrido[3,4-e]azepin-5-yl)-N-ethylacetamide, ±2-(7-(4-chlorophenyl)-9-(difluoromethoxy)-2-methyl-3-oxo-3,5-dihydro-2H-benzo[c]pyrido[3,4-e]azepin-5-yl)-N-ethylacetamide, ±2-(9-methoxy-2-methyl-3-oxo-7-(trifluoromethyl)-3,5-dihydro-2H-benzo[c]pyrido[3,4-e]azepin-5-yl)-N-ethylacetamide, (S)-2-(9-methoxy-2-methyl-3-oxo-7-(trifluoromethyl)-3,5-dihydro-2H-benzo[c]pyrido[3,4-e]azepin-5-yl)-N-ethylacetamide, (R)-2-(9-methoxy-2-methyl-3-oxo-7-(trifluoromethyl)-3,5-dihydro-2H-benzo[c]pyrido[3,4-e]azepin-5-yl)-N-ethylacetamide, ±2-(7-(4-cyanophenyl)-9-methoxy-2-methyl-3-oxo-3,5-dihydro-2H-benzo[c]pyrido[3,4-e]azepin-5-yl)-N-ethylacetamide, ±2-(9-methoxy-2-methyl-7-(5-methylpyridin-2-yl)-3-oxo-3,5-dihydro-2H-benzo[c]pyrido[3,4-e]azepin-5-yl)-N-ethylacetamide, ±2-(7-(4-chlorophenyl)-2-methyl-3-oxo-9-(trifluoromethyl)-3,5-dihydro-2H-benzo[c]pyrido[3,4-e]azepin-5-yl)-N-ethylacetamide, ±2-(7-(4-chlorophenyl)-2-isopropyl-9-methoxy-3-oxo-3,5-dihydro-2H-benzo[c]pyrido[3,4-e]azepin-5-yl)-N-ethylacetamide, ±2-(7-(4-chlorophenyl)-9-fluoro-2-methyl-3-oxo-3,5-dihydro-2H-benzo[c]pyrido[3,4-e]azepin-5-yl)-N-ethylacetamide, ±2-(7-(2,6-difluorophenyl)-9-methoxy-2-methyl-3-oxo-3,5-dihydro-2H-benzo[c]pyrido[3,4-e]azepin-5-yl)-N-ethylacetamide, ±2-(7-(4-chloro, 2-methylphenyl)-9-methoxy-2-methyl-3-oxo-3,5-dihydro-2H-benzo[c]pyrido[3,4-e]azepin-5-yl)-N-ethylacetamide, ±2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide, (S)-2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide, (R)-2-(7-(4-chlorophenyl)-9-methoxy-2-methyl-3-oxo-3,5-dihydro-2H-benzo[c]pyrido[3,4-e]azepin-5-yl)-N-(4-hydroxyphenyl)acetamide, ±7-(4-chlorophenyl)-9-methoxy-2,5-dimethyl-2H-benzo[c]pyrido[3,4-e]azepin-3(5H)-one, (S)-7-(4-chlorophenyl)-9-methoxy-2,5-dimethyl-2H-benzo[c]pyrido[3,4-e]azepin-3(5H)-one, (R)-7-(4-chlorophenyl)-9-methoxy-2,5-dimethyl-2H-benzo[c]pyrido[3,4-e]azepin-3(5H)-one, ±7-(4-chlorophenyl)-9-methoxy-2-methyl-2H-benzo[c]pyrido[3,4-e]azepin-3(5H)-one, ±2-(7-(4-chlorophenyl)-2-methyl-3-oxo-9-(trifluoromethyl)-3,5-dihydro-2H-benzo[c]pyrido[3,4-e]azepin-5-yl)acetic acid, ±2-(7-(4-chlorophenyl)-9-methoxy-2-methyl-3-oxo-3,5-dihydro-2H-benzo[c]pyrido[3,4-]azepin-5-yl)acetic acid, ±tert-butyl ((7-(4-chlorophenyl)-9-methoxy-2-methyl-3-oxo-3,5-dihydro-2H-benzo[c]pyrido[3,4-e]azepin-5-yl)methyl)carbamate, and ±N-((7-(4-chlorophenyl)-9-methoxy-2-methyl-3-oxo-3,5-dihydro-2H-benzo[c]pyrido[3,4-e]azepin-5-yl)methyl)acetamide.

16. The method of claim 2, wherein the leukemia is acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia.

* * * * *